United States Patent
Rubenstein

(10) Patent No.: US 12,414,730 B2
(45) Date of Patent: Sep. 16, 2025

(54) METHODS FOR TRACKING ROTATIONAL ACTIVATION SITES IN ATRIAL FIBRILLATION

(71) Applicants: PRISMA HEALTH—UPSTATE, Greenville, SC (US); HEALTH SCIENCES CENTER, LLC, Greenville, SC (US)

(72) Inventor: Donald S. Rubenstein, Greenville, SC (US)

(73) Assignees: UNIVERSITY OF SOUTH CAROLINA, Columbia, SC (US); PRISMA HEALTH—UPSTATE, Greenville, SC (US)

( * ) Notice: Subject to any disclaimer, the term of this patent is extended or adjusted under 35 U.S.C. 154(b) by 1020 days.

(21) Appl. No.: 16/972,132

(22) PCT Filed: Jun. 6, 2019

(86) PCT No.: PCT/US2019/035688
§ 371 (c)(1),
(2) Date: Dec. 4, 2020

(87) PCT Pub. No.: WO2019/236780
PCT Pub. Date: Dec. 12, 2019

(65) Prior Publication Data
US 2021/0228139 A1    Jul. 29, 2021

Related U.S. Application Data

(60) Provisional application No. 62/751,801, filed on Oct. 29, 2018, provisional application No. 62/681,819, filed on Jun. 7, 2018.

(51) Int. Cl.
*A61B 5/367* (2021.01)
*A61B 5/00* (2006.01)
(Continued)

(52) U.S. Cl.
CPC .............. *A61B 5/367* (2021.01); *A61B 5/287* (2021.01); *A61B 5/333* (2021.01); *A61B 5/361* (2021.01);
(Continued)

(58) Field of Classification Search
CPC ......... A61B 5/367; A61B 5/287; A61B 5/333; A61B 5/361; A61B 5/6857; A61B 5/6858;
(Continued)

(56) References Cited

U.S. PATENT DOCUMENTS 5,637,090 A    6/1997   McGee et al.
10,631,749 B2  4/2020   Rubenstein
(Continued)

FOREIGN PATENT DOCUMENTS

WO    WO 2017/024107        2/2017
WO    WO-2017024107 A1 *    2/2017 ......... A61B 18/1492

OTHER PUBLICATIONS

Allessie, et al. "Intra-atrial reentry as a mechanism for atrial flutter induced by acetylcholine and rapid atrial pacing" *Circulation* 70 (1984) pp. 123-135.
(Continued)

*Primary Examiner* — Adam Z Minchella
(74) *Attorney, Agent, or Firm* — DORITY & MANNING, P.A.

(57) ABSTRACT

Cardiac mapping catheters and methods for using the catheters are described. The catheter can detect the presence, direction and/or source of a depolarization wave front associated with cardiac arrhythmia. A mapping catheter includes a plurality of bipolar electrode pairs in which the members of each pair are opposed to one another across a perimeter, for instance in a circular pattern (compass mode). The spaced arrangement of the electrodes can be utilized to
(Continued)

identify directional paths of moving electric fields or wave fronts in any direction passing across the endocardial surface. Double potential (DP) recordings in compass mode can provide a regional assessment for the existence of rotational activity. Simultaneous DP recordings in compass mode, narrow-adjacent bipolar, and unipolar recording provide an accurate assessment of the time, location, and path that a rotational mechanism breaches a perimeter of electrodes. Accurate time, location, and path of perimeter breaches can be used to electrically track rotational mechanisms during atrial fibrillation.

16 Claims, 43 Drawing Sheets

(51) Int. Cl.
| | |
|---|---|
| A61B 5/287 | (2021.01) |
| A61B 5/333 | (2021.01) |
| A61B 5/361 | (2021.01) |
| A61B 18/14 | (2006.01) |
| G16H 10/60 | (2018.01) |
| G16H 20/40 | (2018.01) |
| G16H 40/63 | (2018.01) |
| G16H 50/50 | (2018.01) |
| G16H 50/70 | (2018.01) |
| A61B 18/00 | (2006.01) |

(52) U.S. Cl.
CPC .......... *A61B 5/6857* (2013.01); *A61B 5/6858* (2013.01); *A61B 18/1492* (2013.01); *G16H 10/60* (2018.01); *G16H 20/40* (2018.01); *G16H 40/63* (2018.01); *G16H 50/50* (2018.01); *G16H 50/70* (2018.01); *A61B 2018/00577* (2013.01); *A61B 2018/00839* (2013.01); *A61B 2562/0209* (2013.01); *A61B 2562/043* (2013.01)

(58) Field of Classification Search
CPC ...... A61B 18/1492; A61B 2018/00577; A61B 2018/00839; A61B 2562/0209; A61B 2562/043; G16H 10/60; G16H 20/40; G16H 40/63; G16H 50/50; G16H 50/70
See application file for complete search history.

(56) References Cited

U.S. PATENT DOCUMENTS

| | | | |
|---|---|---|---|
| 2002/0111618 A1* | 8/2002 | Stewart | A61B 18/1492 606/41 |
| 2006/0122526 A1* | 6/2006 | Berenfeld | A61B 5/361 600/515 |
| 2009/0264778 A1* | 10/2009 | Markowitz | A61B 5/287 600/300 |
| 2011/0054560 A1 | 3/2011 | Rosenberg et al. | |
| 2013/0006238 A1 | 1/2013 | Ditter et al. | |
| 2014/0200575 A1 | 7/2014 | Spector | |
| 2015/0351652 A1 | 12/2015 | Marecki et al. | |

OTHER PUBLICATIONS

Allessie, et al. "Circus movement in rabbit atrial muscle as a mechanism of tachycardia. III. The "leading circle" concept: A new model of circus movement in cardiac tissue without the involvement of an anatomical obstacle" *Circ. Res.* 41 (1977) pp. 9-18.
Atienza, et al. "Mechanisms of fractionated electrograms formation in the posterior left atrium during paroxysmal atrial fibrillation in humans" *J. Am. Coll. Cardio.* 57 (2011) pp. 1081-1092.
Bayer, et al. "Novel radiofrequency ablation strategies for terminating atrial fibrillation in the left atrium: A simulation study" *Front. Physiol.* 7:108 (2016) pp. 1-13.
Benharash, et al. "Quantitative analysis of localized sources identified by local impulse and rotor modulation mapping in atrial fibrillation" *Circ. Arrhythm. Electrophysiol.* 8 (2015) pp. 554-561.
Bray, et al. "Consideration in phase plane analysis for nonstationary reentrant cardiac behavior" *Phys. Rev. E.* 65:051902 (2002) pp. 1-8.
Buch, et al. "Long-term clinical outcomes of focal impulse and rotor modulation for treatment of atrial fibrillation: A multicenter experience" *Heart Rhythm* 13 (2016) pp. 636-641.
Cherry, et al. "Visualization of spiral and scroll waves in simulated and experimental cardiac tissue" *New J. Phys.* 10:125016 (2008) pp. 1-43.
Davidenko, et al. "Stationary and drifting spiral waves of excitation in isolated cardiac muscle" *Nature* 355 (1992) pp. 349-351.
Davidenko, et al. "Sustained vortex-like waves in normal isolated ventricular muscle" *PNAS* 87 (1990) pp. 8785-8789.
Feld, et al. "Mechanism of double potentials recorded during sustained atrial flutter in the canine right atrial crush-injury model" *Circulation* 86 (1992) pp. 628-641.
Ganesan, et al. "Bipolar electrogram shannon entropy at sites of rotational activation: Implications for ablation of atrial fibrillation" *Circ. Arrhythm. Electrophysiol.* 6 (2013) pp. 48-57.
Ghoraani, et al. "Localized rotational activation in the left atrium during human atrial fibrillation: Relationship to complex fractionated atrial electrograms and low-voltage zones" *Heart Rhythm* 10 (2013) pp. 1830-1838.
Gianni, et al. "Acute and early outcomes of focal impulse and rotor modulation (FIRM)-guided rotors-only ablation in patients with nonparoxysmal atrial fibrillation" *Heart Rhythm* 13 (2016) pp. 830-835.
Gray, et al. "Spatial and temporal organization during cardiac fibrillation" *Nature* 392 (1998) pp. 75-78.
Haïssaguerre, et al. "Driver domains in persistent atrial fibrillation" *Circulation* 130 (2014) pp. 530-538.
Haïssaguerre, et al. "Spontaneous Initiation of Atrial Fibrillation by Ectopic Beats Originating in the Pulmonary Veins" *N. Engl. J. Med.* 339 (1998) pp. 659-666.
Holm, et al. "Epicardial right atrial free wall mapping in chronic atrial fibrillation. Documentation of repetitive activation with a focal spread—a hitherto unrecognised phenomenon in man" *Eur. Heart J.* 18 (1997) pp. 290-310.
Jadidi, et al. "Functional nature of electrogram fractionation demonstrated by left atrial high density mapping" *Circ. Arrhythm. Electrophysiol.* 5 (2012) pp. 32-42.
Jalife, et al. "Mother rotors and fibrillatory conduction: a mechanism of atrial fibrillation" *Cardiovasc. Res.* 54 (2002) pp. 204-216.
Konings, et al. "Configuration of unipolar atrial electrograms during electrically induced atrial fibrillation in humans" *Circulation* 95 (1997) pp. 1231-1241.
Konings, et al. "High-density mapping of electrically induced atrial fibrillation in humans" *Circulation* 89 (1994) pp. 1665-1680.
Lee, et al. "Characterization of foci and breakthrough sites during persistent and long-standing persistent atrial fibrillation in patients: Studies using high-density (510-512 electrodes) biatrial epicardial mapping" *J. Am. Heart Assoc.* e005274 (2017) pp. 1-12.
Lee, et al. "Epicardial wave mapping in human long-lasting persistent atrial fibrillation: Transient rotational circuits, complex wavefronts, and disorganized activity" *Eur. Heart J.* 35 (2014) pp. 86-97.
Lin, et al. "Prevalence, characteristics, mapping, and catheter ablation of potential rotors in nonparoxysmal atrial fibrillation" *Circ. Arrhythm. Electrophysiol.* 6 (2013) pp. 851-858.
Lin, et al. "Pulmonary vein antral isolation and nonpulmonary vein trigger ablation without additional substrate modification for treating longstanding persistent atrial fibrillation" *J. Cardiovasc. Electrophysiol.* 8 (2012) pp. 806-813.
Mandapati, et al. "Stable microreentrant sources as a mechanism of atrial fibrillation in the isolated sheep heart" *Circulation* 101 (2000) pp. 194-199.

(56) References Cited

OTHER PUBLICATIONS

Miller, et al. "Initial independent outcomes from focal impulse and rotor modulation ablation for atrial fibrillation: Multicenter FIRM registry" *J. Cardiovasc. Electrophysiol.* 25 (2014) pp. 921-929.
Moe, et al. "A computer model of atrial fibrillation" *Am. Heart J.* 67 (1964) pp. 200-220.
Nademanee, et al. "A new approach for catheter ablation of atrial fibrillation: Mapping of the electrophysiologic substrate" *J. Am. Coll. Cardiol.* 43 (2004) pp. 2044-2053.
Nakagawa, et al. "Pathophysiologic basis of autonomic ganglionated plexus ablation in patients with atrial fibrillation" *Heart Rhythm* 6 (2009) pp. S26-S34.
Narayan, et al. "Panoramic electrophysiological mapping but not electrogram morphology identifies stable sources for human atrial fibrillation: Stable atrial fibrillation rotors and focal sources relate poorly to fractionated electrograms" *Circ. Arrhythm. Electrophysiol.* 6 (2013) pp. 58-67.
Narayan, et al. "Direct or coincidental elimination of stable rotors or focal sources may explain successful atrial fibrillation ablation: On-treatment analysis of the CONFIRM trial (Conventional ablation for AF with or without focal impulse and rotor modulation)" *J. Am. Coll. Cardiol.* 62 (2013) pp. 138-147.
Narayan, et al. "Treatment of atrial fibrillation by the ablation of localized sources: CONFIRM (Conventional Ablation for Atrial Fibrillation with or without Focal Impulse and Rotor Modulation) trial" *J. Am. Coll. Cardiol.* 60 (2012) pp. 628-636.
Olshanksy, et al. "Characterization of double potentials in human atrial flutter: studies during transient entrainment" *J. Am. Coll. Cardiol.* 15 (1990) pp. 833-841.
Pathik, et al. "Absence of rotational activity detected using 2-dimensional phase mapping in the corresponding 3-dimensional phase maps in human persistent atrial fibrillation" *Heart Rhythm* 15 (2018) pp. 182-192. (Abstract only).
Pathik, et al. "Transient rotor activity during prolonged 3-dimensional phase mapping in human persistent atrial fibrillation" *JACC Clin. Electrophysiol.* 4 (2018) pp. 72-83.
Roney, et al. "Spatial resolution requirements for accurate identification of drivers of atrial fibrillation" *Circ. Arrhythm. Electrophysiol.* 10:e004899 (2017) pp. 1-13.
Shivkumar, et al. "Acute termination of human atrial fibrillation and catheter ablation of localized rotors and sources: First multicenter experience of focal impulse and rotor modulation (FIRM) ablation" *J. Cardiovasc. Electrophysiol.* 23 (2012) pp. 1277-1285.
Steinberg, et al. "Focal Impulse and rotor modulation: Acute procedural observations and extended clinical follow-up" *Heart Rhythm* 14 (2017) pp. 192-197.
Swarup, et al. "Stability of rotors and focal sources for human atrial fibrillation: Focal impulse and rotor mapping (FIRM) of AF sources and fibrillatory conduction" *J. Cardiovasc. Electrophysiol.* 25 (2014) pp. 1284-1292.
Umapathy, et al. "Phase mapping of cardiac fibrillation" *Circ. Arrhythm. Electrophysiol.* 3 (2010) pp. 105-114.
Weerasooriya, et al. "Catheter ablation for atrial fibrillation: Are results maintained at 5 years of follow-up?" *J. Am. Coll. Cardiol.* 57 (2011) pp. 160-166.
Yamazaki, et al. "Heterogeneous atrial wall thickness and stretch promote scroll waves anchoring during atrial fibrillation" *Cardiovasc. Res.* 94 (2012) pp. 48-57.
Zlochiver, et al. "Rotor meandering contributes to irregularity in electrograms during atrial fibrillation" *Heart Rhythm* 5 (2008) pp. 846-854.
ISA. "International Search Report" *Int'l Search Auth.* PCT/2019/035688 (Aug. 27, 2019) pp. 1-3.
EPO. "Extended European Search Report" *Euro. Pat. Off.* 19814484.2 (Feb. 3, 2022) pp. 1-8.

\* cited by examiner

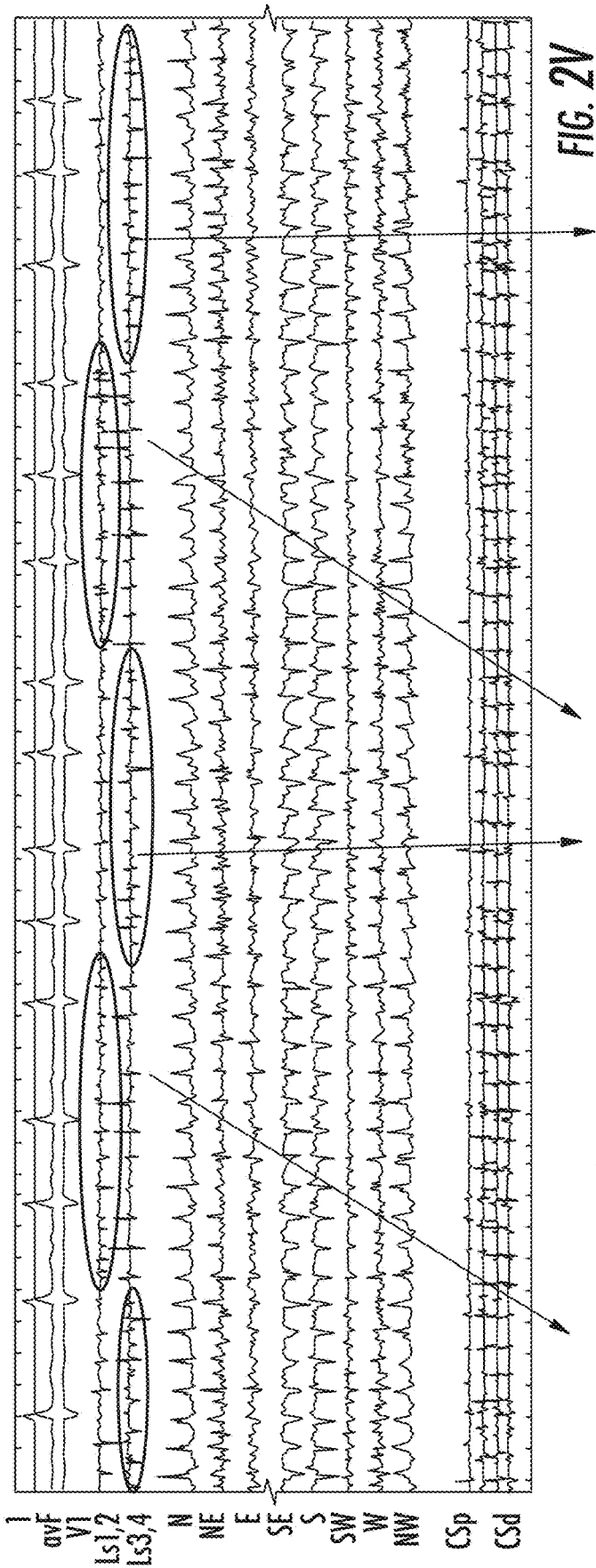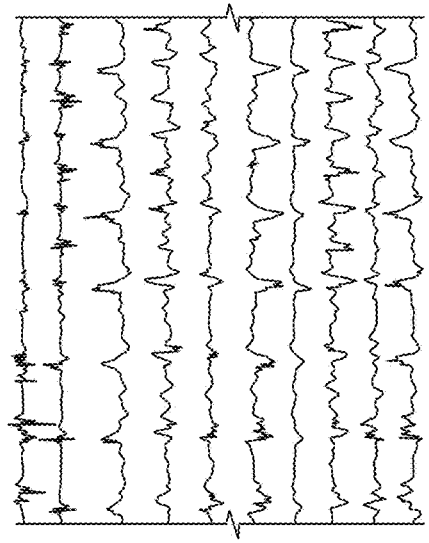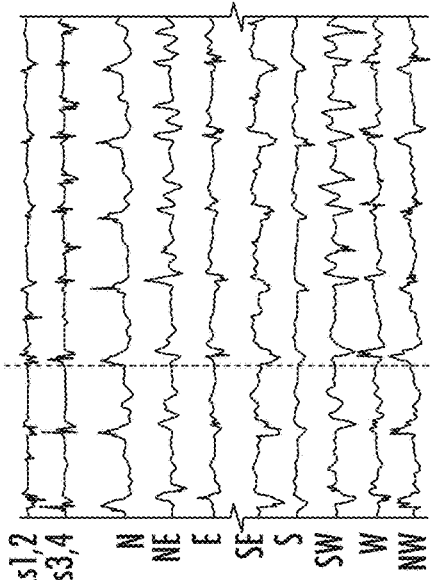

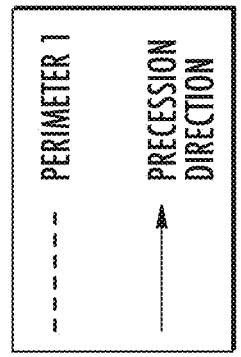
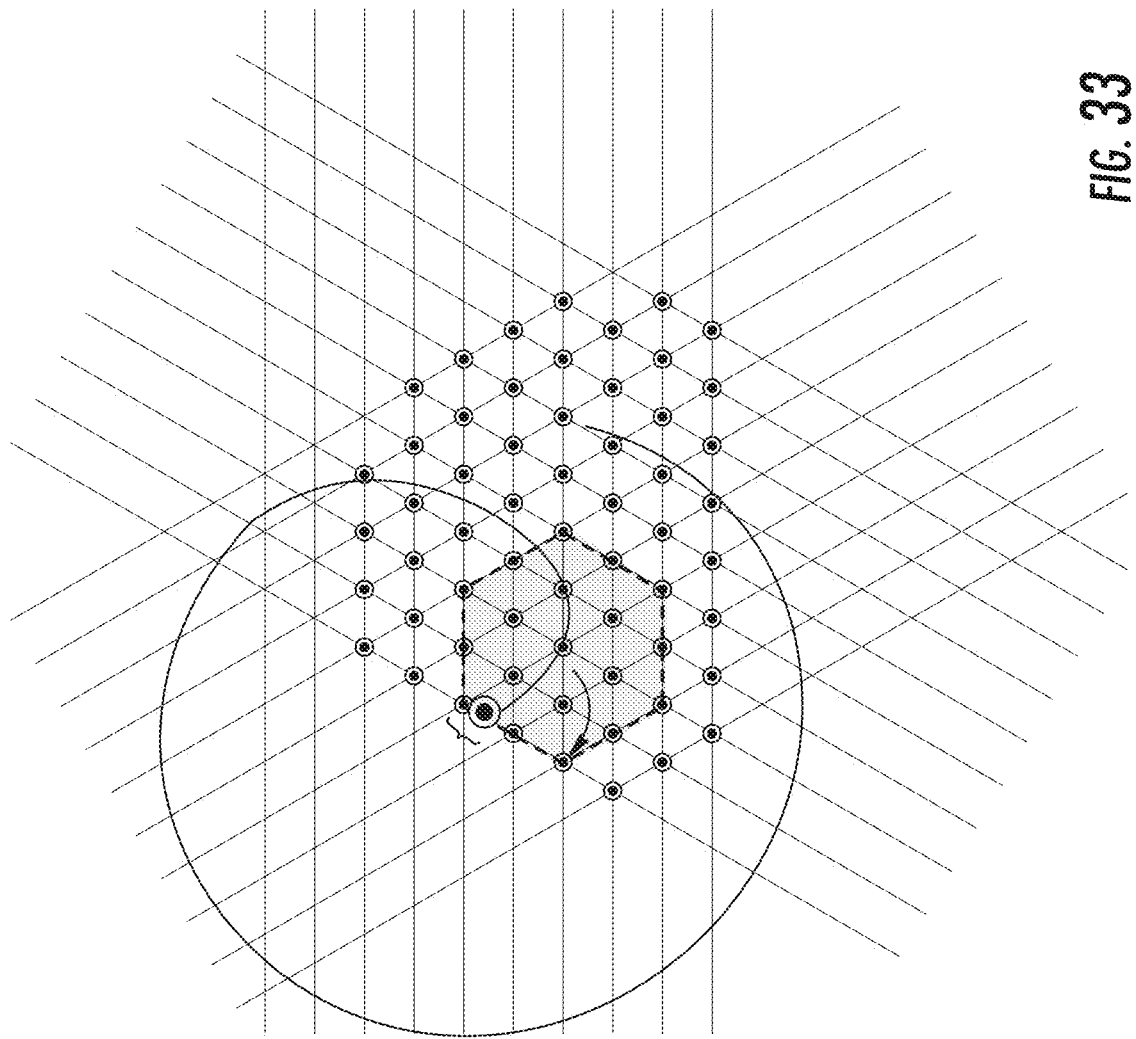
FIG. 33

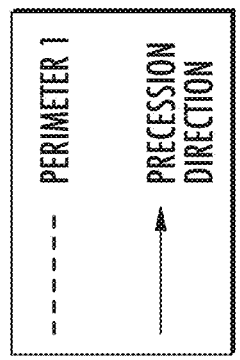
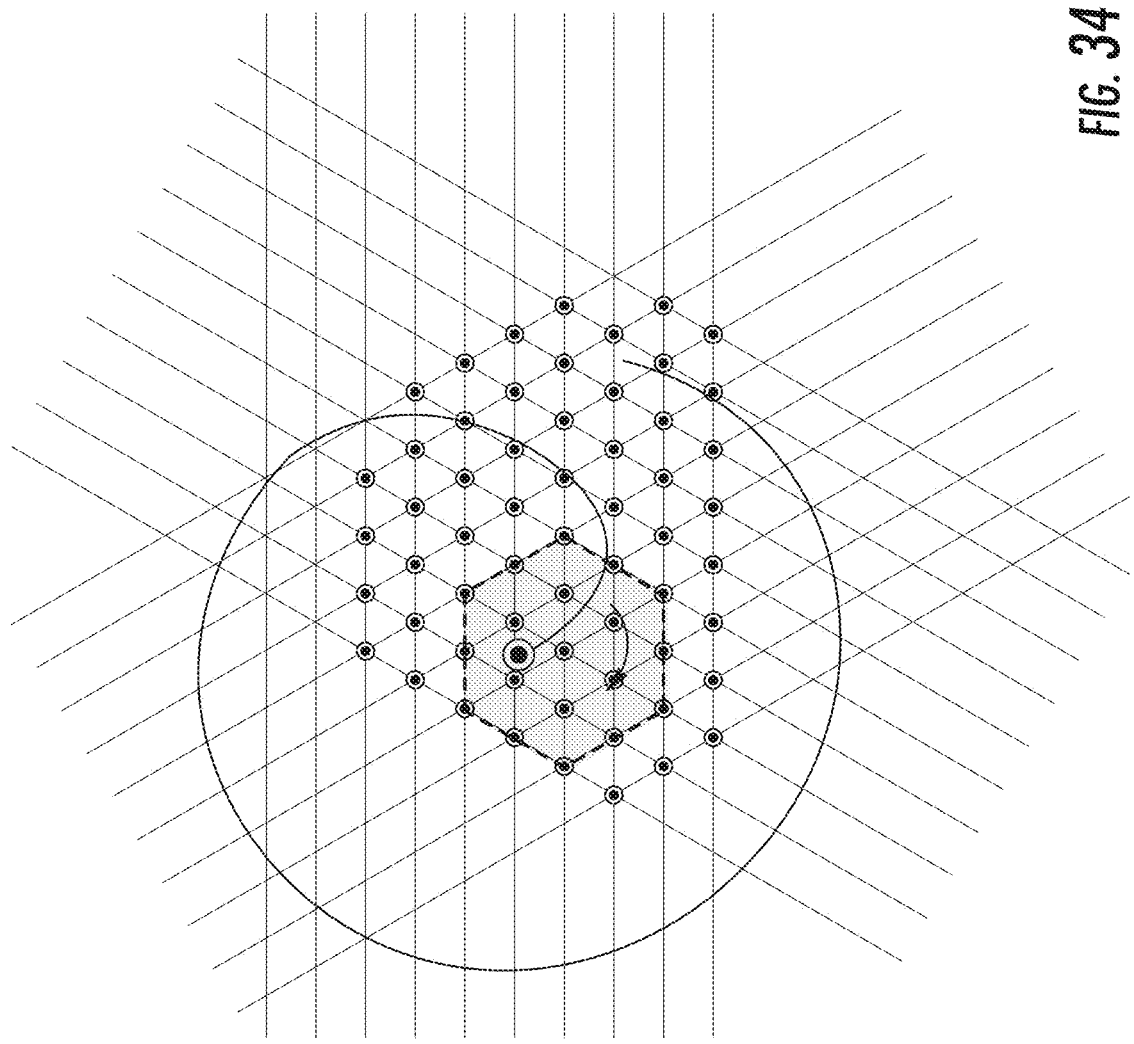
FIG. 34

ENDOCARDIAL SURFACE

EPICARDIAL SURFACE

METHODS FOR TRACKING ROTATIONAL ACTIVATION SITES IN ATRIAL FIBRILLATION

PRIORITY INFORMATION

The present application is the national stage entry of International Patent Application No. PCT/US2019/035688, filed on Jun. 6, 2019, which claims priority to U.S. Provisional Patent Application Ser. No. 62/681,819, titled "Methods for Tracking Rotational Activation Sites In Atrial Fibrillation" by Rubenstein, filed on Jun. 7, 2018, and to U.S. Provisional Patent Application Ser. No. 62/751,801, titled "Methods for Tracking Rotational Activation Sites in Atrial Fibrillation" by Rubenstein, filed on Oct. 29, 2018, the disclosures of which are fully incorporated by reference herein and for all purposes.

BACKGROUND

Atrial fibrillation is the most common cardiac arrhythmia. It creates rapid quivering of the upper chambers of the heart. Acute symptoms can include palpitations, chest pain, shortness of breath and dizziness. Prolonged arrhythmia can result in significant morbidity by potentially causing congestive heart failure and/or stroke.

Theoretical and computational cardiac models have helped to confirm that during arrhythmia the electrical wavefront transmitted through the heart causing contraction or a heartbeat degenerates into one or more rotors. Rotors exhibit a characteristic spiral-shaped wave front of depolarization from a core of affected cells. A rotor's spiral waves present as a repetitive cycle of electrical activation around the central core.

The current understanding of atrial fibrillation in humans requires a coordination of two main events. First, an initiating cardiac electrical impulse or trigger occurs elsewhere than the normal sinus node pacemaker of the heart. This trigger most commonly originates from sleeves of cardiac tissue at the opening of the pulmonary veins within the left atrium but may also emanate from non-pulmonary vein sites or even degenerate from reentrant circuits (sites from which the cause of the arrhythmia is due to the electric signal not moving in a single wave front from the atria to the ventricles as in the normal circuit, but rather as a circuit looping back upon itself). The second event is rotor formation. A rotor develops when the depolarizing electrical impulse that propagates away from a trigger in the form of a wave front undergoes a wave break, turning on an axis. The turning wave front is believed to be a result of regional changes in structure, fibrosis, fiber orientation, autonomic innervation, local conduction velocity characteristics, and/or refractory periods. The curved wave front of the rotor can create a self-sustaining circular trajectory that spins around its rotor core, called a phase singularity. A rotor can spin fairly fast, with any one rotor having a characteristic cycle length. Cycle lengths have been documented in ranges of about 130 to about 210 milliseconds and are stable over time; for instance, up to tens of minutes. It has been postulated that atrial fibrillation is maintained by a small number (1-2) of high frequency rotors that drive the continuation of the atrial fibrillation. In the case of multiple simultaneous rotors, the rotor exhibiting the highest frequency is considered the driving rotor. High frequency rotors occur more frequently in the left atrium, resulting in a gradient of atrial fibrillation drivers from left to right chambers.

Treating atrial fibrillation by ablation of trigger sites and rotors has shown better results in maintaining sinus rhythm and quality of life as compared to medical therapy. Much investigation is ongoing to further improve acute success rates and longevity of being arrhythmia-free, with mapping and ablation of rotor sites being added to accepted methods of atrial fibrillation ablation.

There are currently two commercially available methods for mapping of rotors. Dominant frequency mapping involves time consuming point-by-point recording of the electrical activity within the heart. Each recording is analyzed by spectral analysis to determine each specific site's most stable dominant frequency. A site-specific recording may provide information about that point but does not provide much information about whether a rotor is nearby. Trying to find a rotor or the path along which a rotor precesses is by hunt-and peck without any guidance as to where to try next.

The second method uses a basket catheter to record electrical activity simultaneously from 64 electrodes (8 electrodes over each of 8 splines). The simultaneous local electrical activity of the atrial chamber is displayed panoramically in 2 dimensions. Recording by basket catheters also presents challenges. Stable electrode contact can be problematic but is required to record, compute and display cardiac electrical activity. Unfortunately, many patients with persistent forms of atrial fibrillation have enlarged atria that can be significantly larger than the basket itself. This results in the substantial technical limitation of not having adequate tissue contact for many of the electrodes. In addition, electrode spacing ranges between 4 to 8 mm along splines, depending on basket size, and full expansion of the largest basket catheter to a diameter of 6 cm results in electrode separation between splines of about 2.5 centimeters. Rotor diameters are estimated to be about 1.5 cm to 2 cm. Thus, the basket geometry allows for only one or two at most electrodes on the catheter to record within a rotor site. The consequential wider spline separation of basket catheters in these enlarged atria diminishes the probability to accurately identify a rotor location.

What are needed in the art are devices and methods for mapping cardiac tissue and thereby recognizing locations of interest during cardiac arrhythmia. For instance, improved ability to map, identify and ablate rotors would be of great benefit. Presently, a rotor site cannot be identified by standard recording techniques and requires color activation time maps. A device and method that can provide for immediate rotor detector/locator, an ectopic site detector/locator and a circuit locator would be of great benefit.

SUMMARY

Aspects and advantages of the presently disclosed subject matter will be set forth in part in the following description, or may be apparent from the description, or may be learned through practice of the presently disclosed subject matter.

In general, it is a present object to provide improved methodology for mapping cardiac tissue and associated and/or corresponding apparatus.

One presently disclosed exemplary embodiment relates to a method for mapping cardiac tissue for patients experiencing atrial fibrillation. Such method preferably comprises placing a mapping catheter comprising an array of electrodes in contact with cardiac tissue, the array of electrodes comprising an electrode configuration of a mapping catheter forming a perimeter of such electrodes and wired for wide cross-perimeter electrode pairing for compass mapping, and wired for narrow-adjacent bipolar and unipolar recordings from such electrodes; simultaneously measuring electrical signals from such electrodes and recording compass map readings, narrow-adjacent bipolar readings, and unipolar readings therefrom; and analyzing the measured and recorded electrical signal readings to identify waveforms therein to determine at least one characteristic of a wave front of depolarization passing through the cardiac tissue.

Another presently disclosed exemplary embodiment relates to methodology for locating and targeting electrically migrating rotational mechanisms in cardiac tissue of patients experiencing atrial fibrillation. Such methodology preferably comprises (a) placing a mapping catheter comprising an array of electrodes in contact with cardiac tissue; (b) simultaneously measuring and recording electrical signals from such electrodes; and (c) analyzing the measured and recorded electrical signal readings to identify waveforms therein to (1) determine a site of breach of an identified rotational mechanism through a predetermined section of electrodes, and to (2) then determine a direction of migration of such identified rotational mechanisms based on activations of other of such electrodes.

Yet another presently disclosed exemplary embodiment relates to a method for locating and mapping electrically migrating rotational depolarization wave fronts passing through cardiac tissue of patients experiencing atrial fibrillation, for establishing cardiac tissue target sites for therapeutic treatment based on paths of located wave fronts. Such method preferably comprises providing a mapping catheter comprising an array of electrodes, configured to form a perimeter of such electrodes and wired for wide cross-circle electrode pairing for compass mapping, and wired for adjacent bipolar and unipolar recordings from such electrodes; placing such mapping catheter in contact with cardiac tissue at a plurality of successive sites; measuring and recording electrical signals from such mapping catheter electrodes at each of such successive sites; identifying a breach along a portion of such electrodes by a migrating depolarization wave front; identifying a second breach along another portion of such electrodes by a migrating depolarization wave front; and repeating such identifications to determine a path and life of an identified migrating depolarization wave front.

According to yet another exemplary embodiment, disclosed is a method for mapping cardiac tissue. A method can include placing an array of electrodes in contact with cardiac tissue. The method can also include obtaining electrical signals from a plurality of bipolar electrode pairs of the array (e.g., at least two bipolar electrode pairs), with each bipolar electrode pair including a first electrode and a second electrode. The first and second electrodes of each bipolar electrode pair are at a distance from one another and in electrical communication with one another. The bipolar electrode pairs are located with respect to one another such that the individual electrodes of the bipolar electrode pairs together define a perimeter around an area. The first and second electrodes of each bipolar electrode pair are located on this perimeter such that they are opposed to one another across this area. For instance, in one embodiment, the electrodes of the bipolar electrode pairs together define a circular perimeter. In this embodiment, the first and second electrodes of each bipolar electrode pair can be diametrically opposed to one another across the circular pattern.

A further presently disclosed exemplary method can also include analyzing the electrical signals from each of the bipolar electrode pairs to determine the direction or source of a wave front of depolarization passing through the cardiac tissue. In one particular embodiment, the method can determine the precessing direction and/or core location of a rotor.

In still another exemplary embodiment, a method can include unipolar analysis of the electrical signals of catheter electrodes. Through unipolar analysis of the signals from each electrode sequentially around the perimeter of a catheter area, information regarding the location of a rotor core can be obtained. For instance, through analysis of the electrical signals from bipolar electrode pairs, one can determine the precession direction of the rotor and that a rotor core is within an area defined by the electrodes. Following this determination, unipolar analysis of the signals from the electrodes around the perimeter of the area defined by the catheter can be carried out to provide additional information regarding more specific location of the rotor core within the area defined by the perimeter.

It is to be understood that the presently disclosed subject matter equally relates to associated and/or corresponding device subject matter, as well as the referenced presently disclosed methodologies. Yet another exemplary embodiment of presently disclosed subject matter relates to a cardiac mapping catheter that includes an array of electrodes, the array including a plurality of bipolar electrode pairs. The bipolar electrode pairs can be located with respect to one another such that the electrodes of the bipolar electrode pairs together define a perimeter surrounding an area. The first and second electrodes of each bipolar electrode pair can be opposed to one another across this area. For example, the array can be carried on one or more circular turns of a flexible coil-type catheter with the first and second electrodes of each bipolar electrode pair being diametrically opposed across a circular turn of the coil-type catheter. In other embodiments, the array of electrodes can be carried on a basket-type catheter or on any other sort of a network that includes a grid of electrodes the signals of at least a portion of which can be measured as a plurality of bipolar electrode pairs surrounding an area as described.

Additional objects and advantages of the presently disclosed subject matter are set forth in, or will be apparent to, those of ordinary skill in the art from the detailed description herein. Also, it should be further appreciated that modifications and variations to the specifically illustrated, referred and discussed features, elements, and steps hereof may be practiced in various embodiments, uses, and practices of the presently disclosed subject matter without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the presently disclosed subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the presently disclosed subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification, and will appreciate that the presently disclosed subject matter applies equally to corresponding methodologies as associated with practice of any of the present exemplary devices, and vice versa.

BRIEF DESCRIPTION OF THE DRAWINGS

A full and enabling disclosure of the presently disclosed subject matter, including the best mode thereof, directed to one of ordinary skill in the art, is set forth in the specification, which makes reference to the appended figures, in which:

FIG. 2I represents graphs of activation patterns of areas mapped by an exemplary embodiment of a circular catheter in accordance with presently disclosed subject matter;

FIGS. 2V, 2W, and 2X represent data involved with recorded movement of rotor precession;

FIG. 11 illustrates recordings from electrocardiogram surface leads including recordings from diametrically opposed bipolar electrode pairs as described herein;

FIG. 33 is another illustration of the exemplary embodiment of an alternate geometric array of electrodes of present FIG. 28 providing adjacent and/or overlapping perimeters, and showing results of the recording of a rotor precession at a perimeter resulting from a selected grouping of electrodes, and illustrating such perimeter and the direction of the rotor precession, based on only one narrow pair of electrodes at such perimeter showing a double potential and with all cross perimeter electrode pairs showing a transition from peripheral waves to double potential waves;

FIG. 34 is another illustration of the exemplary embodiment of an alternate geometric array of electrodes of present FIG. 28 providing adjacent and/or overlapping perimeters, and showing results of the recording of a rotor precession within a perimeter resulting from a selected grouping of electrodes, and illustrating such perimeter and the direction of the rotor precession, based on no narrow pairs of electrodes at such perimeter showing a double potential and with all cross-perimeter electrode pairs showing double potential waves;

Figure 1:
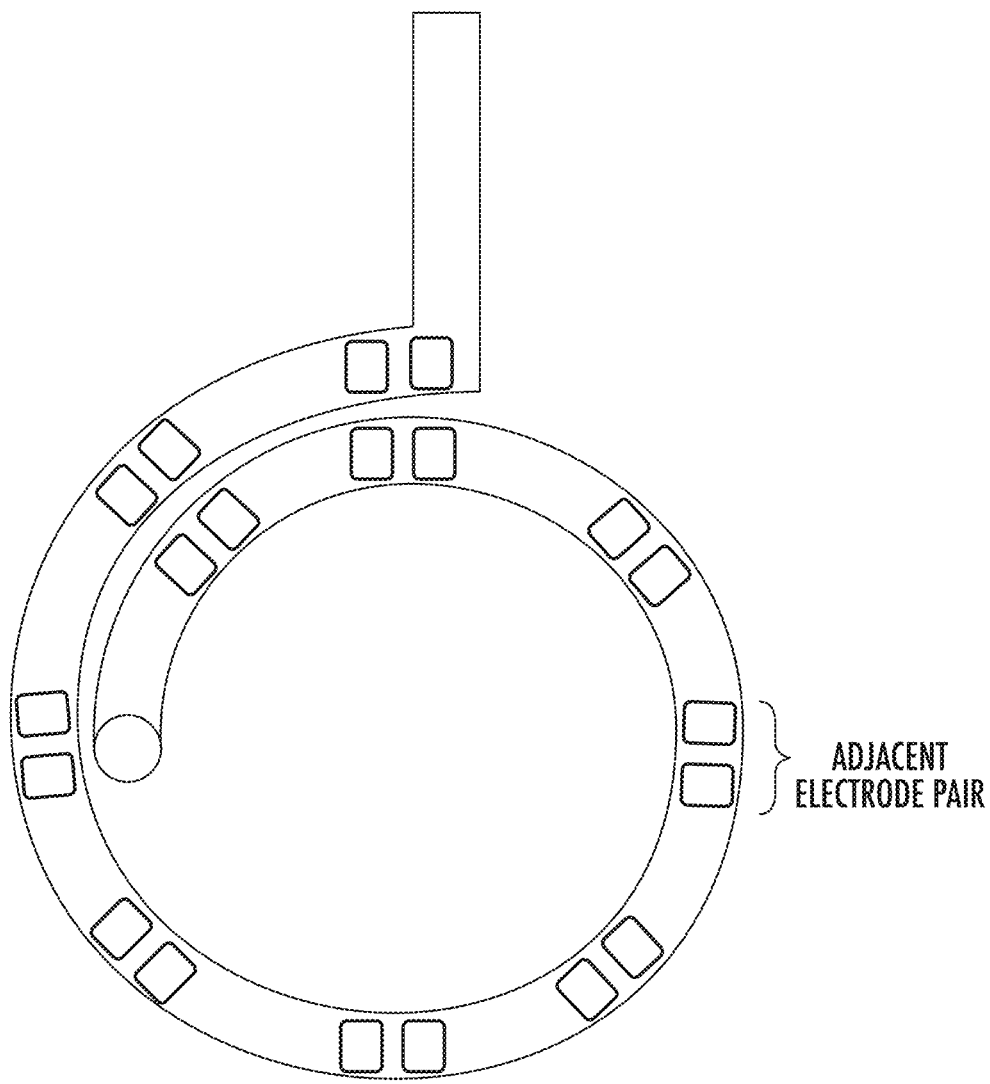
FIG. 1 schematically illustrates a prior art circular mapping electrode catheter.

Repeat use of reference characters in the present specification and drawings is intended to represent the same or analogous features or elements of the presently disclosed subject matter.

DETAILED DESCRIPTION

It is to be understood by one of ordinary skill in the art that the present discussion is a description of exemplary embodiments only and is not intended as limiting the broader aspects of the presently disclosed subject matter. Reference now will be made to the embodiments of the presently disclosed subject matter, one or more examples of which are set forth below. Each example is provided by way of an explanation of the presently disclosed subject matter, not as a limitation of the presently disclosed subject matter. In fact, it will be apparent to those skilled in the art that various modifications and variations can be made in the presently disclosed subject matter without departing from the scope or spirit of the presently disclosed subject matter. For instance, features illustrated or described as one embodiment can be used on another embodiment to yield still a further embodiment. Thus, it is intended that the presently disclosed subject matter cover such modifications and variations as come within the scope of the appended claims and their equivalents. It is to be understood by one of ordinary skill in the art that the present discussion is a description of exemplary embodiments only and is not intended as limiting the broader aspects of the presently disclosed subject matter, which broader aspects are embodied exemplary constructions.

BACKGROUND: Rotational circuits that occur between bipolar electrodes exhibit double potentials (DPs). It had been previously surmised that rotors could not be electrically tracked directly.

As illustrated in FIG. 1, the electrode arrangement of a typical prior art circular mapping catheter includes 10 bipolar electrode pairs (20 electrodes total). Each bipolar electrode pair includes two immediately adjacent electrodes with narrow spacing between the two. For instance, the spacing between the two electrodes of one bipolar electrode pair is generally about 2 millimeters and the spacing between successive bipolar electrode pairs is generally about 5 millimeters. During use, the voltage potential difference between the individual members of a pair is recorded. As known, a rotor exhibits a stable cyclic pattern of a short electrical impulse followed by quiescence. If one of the electrodes of a bipolar electrode pair of a standard catheter as shown in FIG. 1 is within the rotor region, then the regular pattern of electrical activity may be seen but little or no information with regard to the rotor motion (e.g., rotational direction, precession direction) or rotor core location will be obtained.

PURPOSE: The purpose was twofold: First, to show that through the use of compass mapping, one can regionally identify rotational activity; and second, to show that by combining simultaneous compass map recordings, standard narrow-adjacent bipolar, and unipolar recordings, that specific signature recording patterns emerge that allow one to identify the accurate time, location, and path of a rotational mechanism.

METHODS: This was an observational study in 20 patients with persistent atrial fibrillation in which the electrode configuration of a circular mapping catheter was changed to wide cross-circle electrode pairing (compass mapping). DPs were recorded and analyzed from 12 left atrial (LA) sites and identified electrical wavefront patterns and direction. A substudy analyzed transitions patterns with simultaneous narrow-adjacent bipolar and unipolar recordings.

RESULTS: Four wavefront patterns were identified: DPs, peripheral waves (PWs), distal peripheral waves and fibrillatory activity. DP wavefront patterns exhibited significantly shorter cycle lengths than PWs in 8 of 12 LA sites. Patients had 2.9±2.1 regions that exhibited DPs. DPs of varying duration were found, few (25%) were of stable duration and location. Detailed electrical examination at the transition between a PW to a DP identified a highly consistent pattern of simultaneous Doppler compression and expansion of cycle lengths at adjacent electrodes, reversal of activation sequence, and a ½ cycle drop-off of activation signals in the line of electrodes.

CONCLUSIONS: DP recordings in compass mode can provide a regional assessment for the existence of rotational activity. Simultaneous DP recordings in compass mode, narrow-adjacent bipolar, and unipolar recording provide an accurate assessment of the time, location, and path that a rotational mechanism breaches a perimeter of electrodes. Accurate time, location and path of perimeter breaches can be used to electrically track rotational mechanisms during atrial fibrillation.

ABBREVIATIONS: AF=atrial fibrillation; DPs=double potentials; LA=left atrium; PVI=pulmonary vein isolation.

Twenty years have elapsed since the discovery that most atrial fibrillation is triggered by ectopic beats generated within the ostia of the pulmonary veins. Ablation to electrically isolate these regions has provided a meaningful treatment of this arrhythmia, more so for patients with the paroxysmal than the persistent form. Other ectopic sites and mechanisms may trigger or degenerate into atrial fibrillation. Once initiated, additional mechanisms may maintain and prolong fibrillatory activity. Controversy remains if one or multiple simultaneous sustaining factors are at play. Computational and experimental evidence has provided support for multiple rapid ectopic foci, multiple random wavelets, complex fractionated atrial electrograms and rotors.

Reentry and rotors, both have circular paths of electrical wavefronts. However, they differ significantly when analyzing the central region of that circulation. Reentrant wavefronts move centripetally towards a center that has an unexcitable anatomic barrier or it is functionally refractory. This unexcitable region prevents propagation crossing over to the opposite side that might have disrupted the continuous propagation. In contradistinction, rotor wavefronts spiral centrifugally away from a central core, called a phase singularity. There, at the center, the electrical wavefront shape progressively curves inward to a physical limit preventing advancing into the core. However, since the core region is unexcited, this allows drift (precession) to adjacent tissue that may too become briefly excitable, but unexcited. Because of the spiral nature of the rotor wavefront, as well as limitations of conduction properties, the cycle lengths measured nearest the core are shorter than adjacent tissue, thus exhibiting a Doppler effect with an approaching core.

Movies of action potential phase changes by the use of voltage-sensitive dyes on in vitro animal models along with computational algorithms, provided detailed analysis and description of cardiac rotor activity during fibrillatory activity. Direct electrode recordings by traditional methods of mapping in humans were deemed too complex to identify potential target areas for ablation. Rigorous attempts have been made to recreate electrical phase analysis in humans by computational algorithms that interpolate electrical activity between splines of a basket catheter. Ablation within these regions showed initial success for arrhythmia suppression but has been met recently with far less favorable results.

Whether an electrical circuit is reentrant or rotor, direct experimental electrical recordings near the center of rotation, or at its pivot point, consistently exhibit double potentials (DPs). DPs have been identified with intracellular electrodes, unipolar electrodes and bipolar electrodes. The DPs have been confirmed to record activation on opposite sides of the electrical circular path. Closer to the center of rotation or near the site of pivot, the DPs appear evenly split. DPs, termed inverted double split potentials, were consistently identified with bipolar recordings while looking for higher Shannon entropy at rotor core sites. A bipolar electrode (without regard to alignment) that straddles the center of a rotational electrical mechanism will exhibit two activations (DP) recorded with each one revolution. DPs have also been recorded in various other studies and overall can identify activation on either side of a region of conduction block.

We hypothesized that changing the pairing of the narrow adjacent electrodes along a circular mapping catheter to that of cross-circle pairing could provide stable, regional recordings such that the operator could identify the time and place that a rotor entered the perimeter of that region. If a rotor or rotational mechanism moves toward the perimeter of a circular catheter, stable single wavefronts or peripheral waves (PWs) ought to be recorded with each rotation. However, if a rotor that has its plane of rotation parallel to the plane of the recording catheter meanders or precesses across the perimeter of the circular mapping catheter, then the PWs should immediately transition into recording DPs.

In addition, rotor precession in and out of the compass perimeter might provide directional and possibly direct location information as to where the rotor entered and exited. Such a method might utilize direct recognition of alternating double potentials as sites of rotational activation rather than relying on proprietary computation, interpolation, and animated movies.

Study Population

Twenty-two consecutive patients with symptomatic persistent atrial fibrillation (>1 week duration or required cardioversion to regain sinus rhythm) were admitted for ablation. Two patients had a prior ablation with pulmonary vein isolation (PVI). Table 1 provides the patient demographic and clinical characteristics. Each patient signed a written informed consent of the research protocol that was approved by our local institutional review board. All patients underwent a transesophageal echocardiogram one day prior to procedure to exclude a left atrial thrombus. Patients remained on their prescribed oral anticoagulation without cessation. Previously prescribed antiarrhythmic drugs except amiodarone (n=9) were discontinued 5 half-lives prior to their ablation. Patients completed their procedure in the post absorptive state under general anesthesia. Standard access of catheters was performed through femoral and right internal jugular vein access. All research protocol mapping was completed prior to standard pulmonary vein (PV) isolation. PV isolation of all 4 veins was achieved in every patient. AF was terminated in 1 patient during PVI. All other patients underwent additional ablation lines (roof line, mitral isthmus, tricuspid isthmus, and/or appendage) with goal of achieving sinus rhythm. If AF organized to an atrial flutter or tachycardia, then this mechanism was also targeted for ablation. If further mapping and ablation did not terminate into sinus rhythm, then electrical cardioversion was performed. Ablation was performed with a 3.5 mm irrigated tip catheter (THERMOCOOL®, Biosense-Webster, Diamond Bar, CA). Ablation energy used was 25 W along the posterior wall and 30-35 W elsewhere. All electrogram cycles, vector analysis was completed off-line and could not be used to help target ablation.

TABLE 1

| Patient Demographics, n = 22. | |
|---|---|
| Characteristic | Value (%) |
| Age (years) | 65 ± 8 |
| Sex | 15 male, 7 female |
| AF Duration (months) | 7.5 ± 6.2 |
| LA Size (mm) | 4.5 ± 0.6 |
| LVEF (%) | 48 ± 12 |
| BSA ($m^2$) | 2.2 ± 0.3 |
| HTN | 19 (86) |
| DM | 4 (18) |
| Prior Stroke | 1 (5) |
| $CHADS_2VA_2SC$ | 2.3 ± 1.0 |

Compass Mapping Technique

Figure 2A:
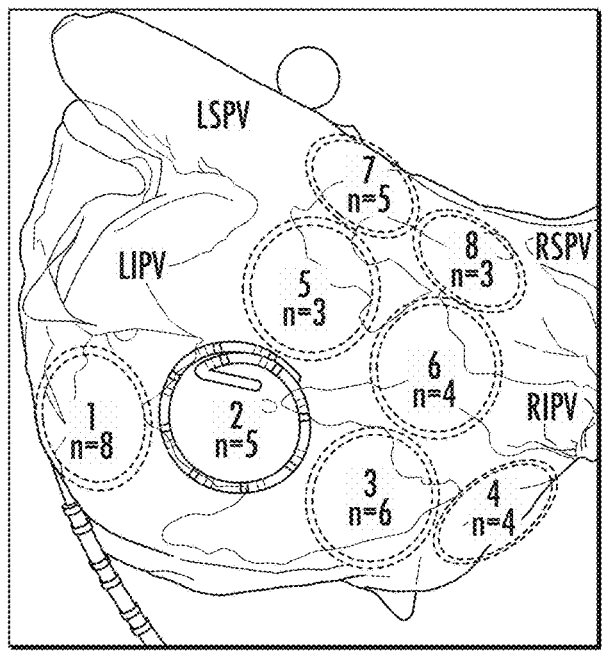
FIG. 2A and FIG. 2B, represent respective left atrial (LA) sites (cardiac sites) of recording per presently disclosed subject matter described herein.
Figure 2B:
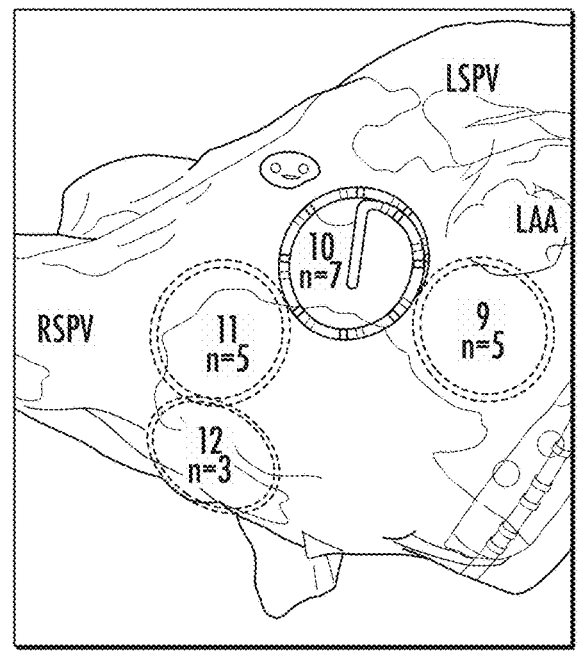
Figure 2C:
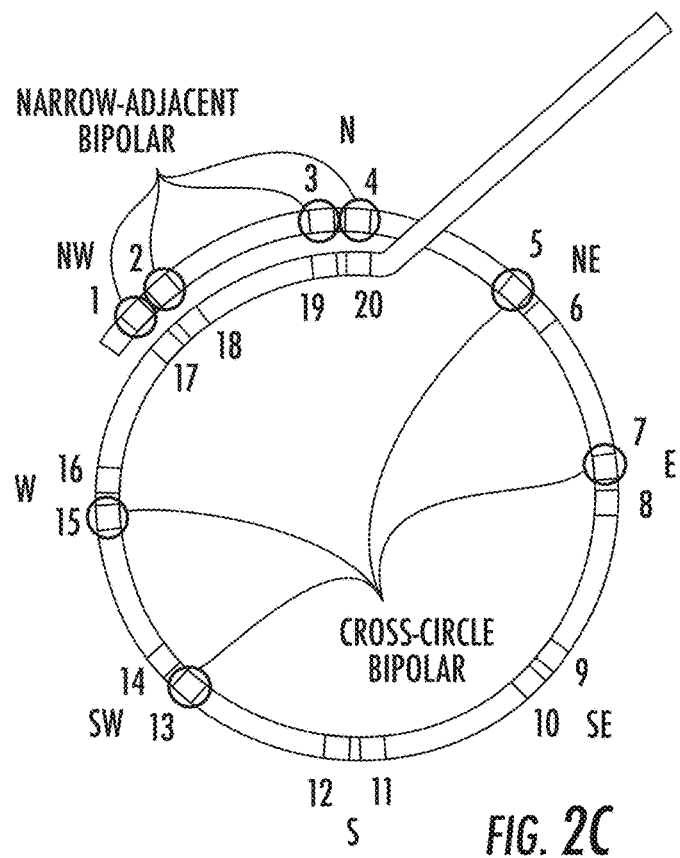
FIG. 2C is a schematic illustration of circular mapping catheter bipolar electrode configurations in accordance with an exemplary embodiment of presently disclosed subject matter.

Experimentally, rotors in animals with atrial fibrillation can control a surrounding tissue area up to 5 $cm^2$. A circular mapping catheter (Lasso™, Biosense Webster, Diamond Bar CA, USA) encircles an area of 3.14 $cm^2$ and was used to systematically map, record, and analyze 12 specific regions of the LA (FIGS. 2A and 2B). To identify and examine rotational activity with the characteristic double potentials, the bipolar electrode input configuration from the standard adjacent narrow pairing of electrodes was changed in the software electrode parameters in the recording workstation (CardioLab™, GE Medical, Milwaukee, WI, USA). An electrode was paired with the electrode directly across the circle, 8 such pairings (using electrodes 5-20) were made moving around the circle (FIG. 2C). Table 2 provides the electrode pair configuration. Electrode pairs (1,2), and (3,4) remained configured as narrow pairs to provide very specific local electrical information while simultaneously recording regional wide cross-circle bipolar recordings. All recordings were made at gain of 500 with low pass and high pass filters set at 30 Hz and 500 Hz respectively. The cross-circle pairing created an electrical compass and were labelled the 8 cardinal points of a compass (N, NE, E SE, S, SW, W, and NW). Looking down the barrel of the shaft where the catheter turns perpendicular to the shaft is designated North. The East direction is designated 90 degrees moving clockwise around the compass. Sliding the thumb lever up moves the catheter downward or to the south. With a 90-degree bend toward the south, rotating the handle clockwise moves the compass to the west.

Figure 2D:
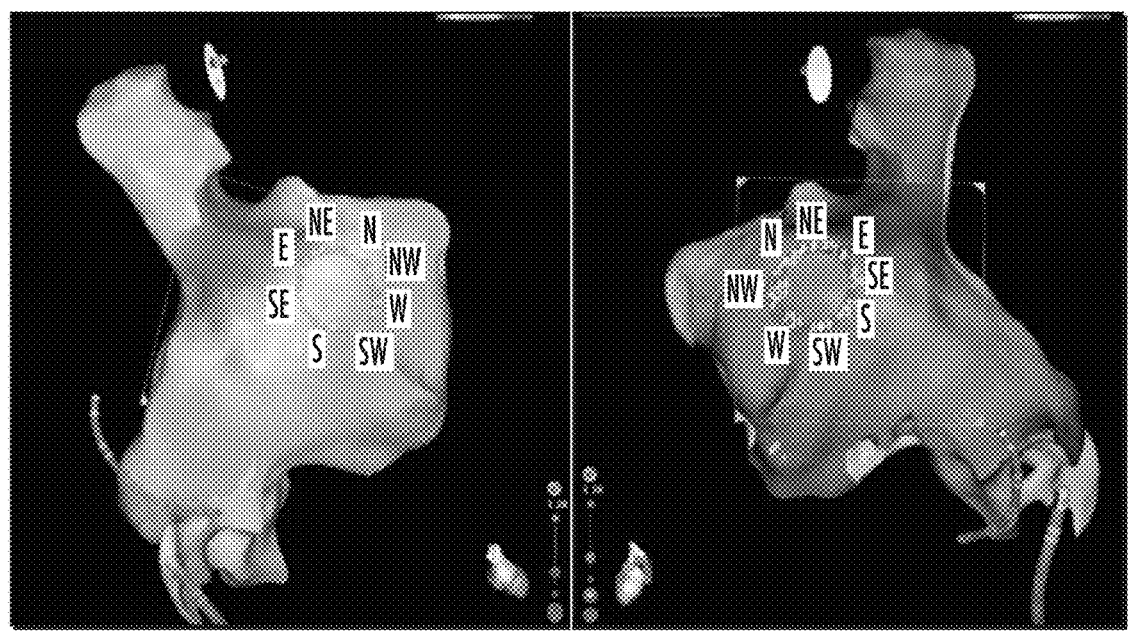
FIGS. 2D and 2E represent exemplary cardiac sites for use with FIG. 2C presently disclosed subject matter.
Figure 2E:
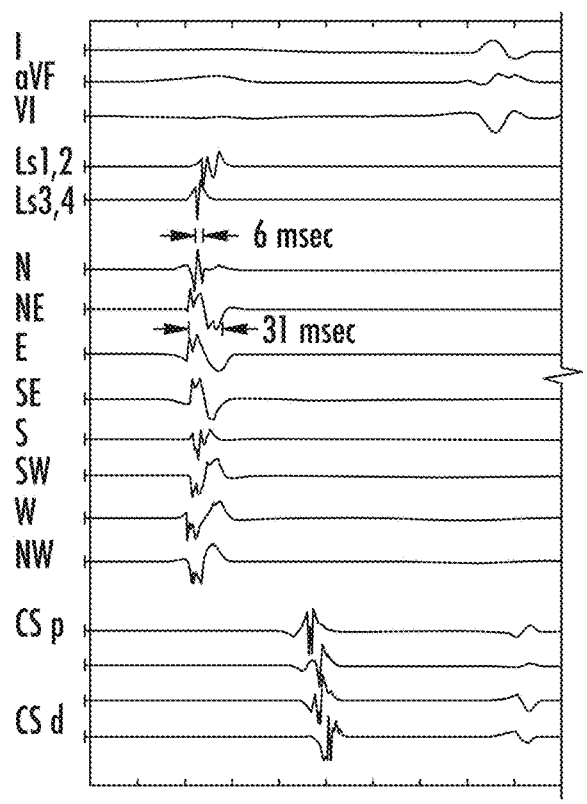

The electrode configuration setup results in a rising slope activation electrogram with an approaching electrical wavefront from that specific cardinal point direction. Compass directional information was confirmed with a 3-dimensional high-density activation map that was created in sinus rhythm of the right atrium (FIG. 2D, 2E). The circular mapping catheter was placed just inferior to the sinus node along the lateral wall with East electrode of the compass closest to the sinus node. Note that a large broad wavefront propagates past electrodes parallel to wavefront direction, whereas activation perpendicular to the wavefront is very short.

FIG. 2A and FIG. 2B. Left atrial sites of recording (LA). FIG. 2A. Posterior view of LA. Recording sites 1-8. Site 1: left lateral atrial wall; site 2: left inferior posterolateral; site 3: left inferior posteromedial; site 4: left posteroseptal; site 5: Left inferior pulmonary vein (LIPV) posterior wall ostia; site 6: Right inferior pulmonary vein (RIPV) posterior wall ostia; site 7: Left superior pulmonary vein (LSPV) posterior wall ostia; site 8: Right superior (LSPV) posterior wall ostia. FIG. 2B. site 9: left anterolateral adjacent to left atrial appendage (LAA); site 10: roof at LSPV; site 11: roof at RSPV; site 12: left antero-septal. At each site, identified by dashed circles, DPs were observed by n number of patients.

TABLE 2

Electrode configuration of cross-circle bipolar pairings to create compass recordings.

| Catheter | Label | Type | Inputs + | − |
|---|---|---|---|---|
| Coronary Sinus | CS 1, 2 | Bipolar | 2 | 1 |
| | CS 3, 4 | Bipolar | 4 | 3 |
| | CS 5, 6 | Bipolar | 6 | 5 |
| | CS 7, 8 | Bipolar | 8 | 7 |
| | CS 9, 10 | Bipolar | 10 | 9 |
| Circular Mapping | Ls 1, 2 | Narrow Bipolar | 12 | 11 |
| | Ls 3, 4 | Narrow Bipolar | 14 | 13 |
| | N 11, 19 | X-Circle Bipolar | 21 | 29 |
| | NW 9, 17 | X-Circle Bipolar | 19 | 27 |
| | W 7,1 5 | X-Circle Bipolar | 17 | 25 |
| | SW 5, 13 | X-Circle Bipolar | 15 | 23 |
| | S 12, 20 | X-Circle Bipolar | 30 | 22 |
| | SE 10, 18 | X-Circle Bipolar | 28 | 20 |
| | E 8, 16 | X-Circle Bipolar | 26 | 18 |
| | NE 6, 14 | X-Circle Bipolar | 24 | 16 |

FIG. 2D and FIG. 2E. Electrode pairing configuration to create compass-mode recording. FIG. 2D. Schematic of circular mapping catheter bipolar electrode configurations.

Narrow-adjacent bipolar electrode pair included (1,2) and (3,4). Cross-circle bipoles are arranged in a compass-mode configuration North or N=bipolar electrode pair (11,19); NW=bipolar electrode pair (9,17); W=bipolar electrode pair (7,15); SW=bipolar electrode pair (5,13); S=bipolar electrode pair (12,20); SE=bipolar electrode pair (10,18); E=bipolar electrode pair (8,16); and NE=bipolar electrode pair (6,14). FIG. 2E. 3-D electroanatomic map identifies sinus node region in red external perspective on left, internal perspective on right. East electrode (E) is closest to sinus node. C. Recording of electrical wavefront with circular catheter placed at lateral wall of right atrium in sinus rhythm. Top 3 recordings are surface leads 1, avF, and V1. The next two traces are recorded from narrow adjacent pairs (1,2) and (3,4). The next 8 traces record form the 8 cross-circle bipolar electrodes as configured in 2A. The last 5 traces record activation from the coronary sinus catheter (CS) from proximal (p) to distal (d). Atrial wavefront originating from sinus node moves across recording region of circular mapping catheter that records in compass mode with the E direction showing the largest, broadest activation. Perpendicular to this direction, N and S directions show smallest and narrowest activation.

Figure 2F:
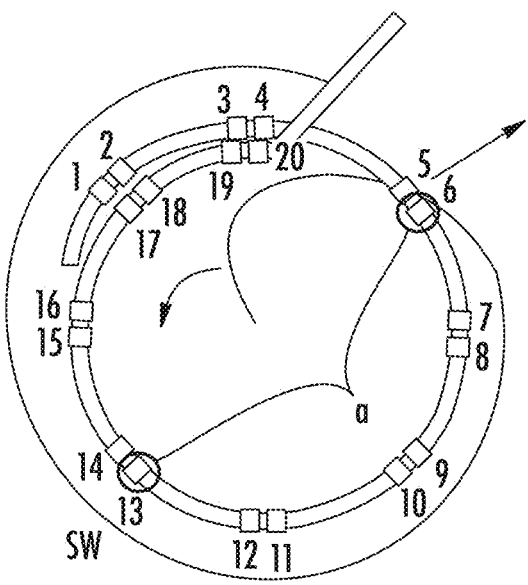
FIG. 2F represents a diagram of a counterclockwise rotor that exhibits DPs of alternating slope in compass-mode mapping.
Figure 2G:
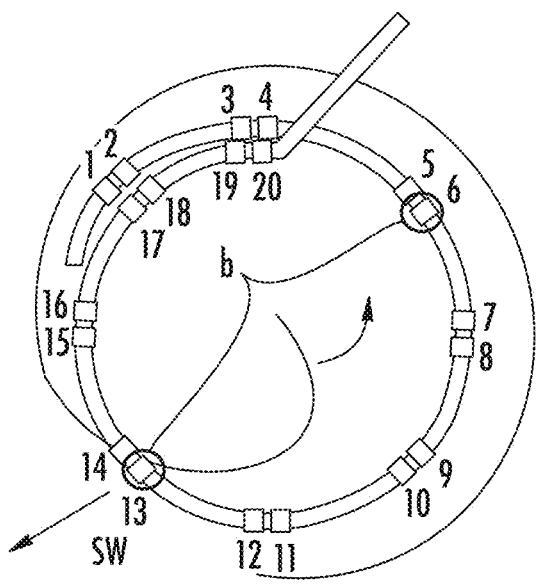
FIG. 2G illustrates the subject matter of FIG. 2F, one half cycle later in time.
Figure 2H:
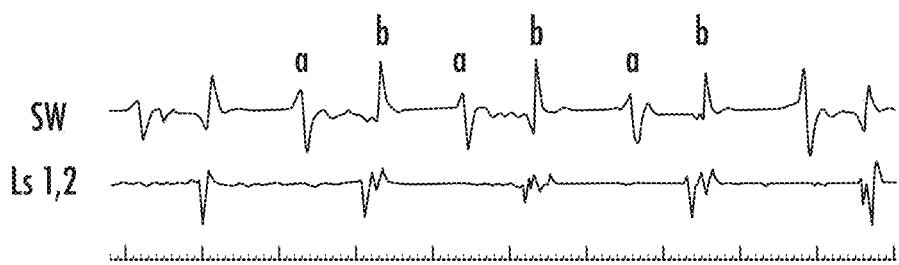
FIG. 2H represents tracings of showing recordings from the SW direction with alternating DPs.
Figure 21:
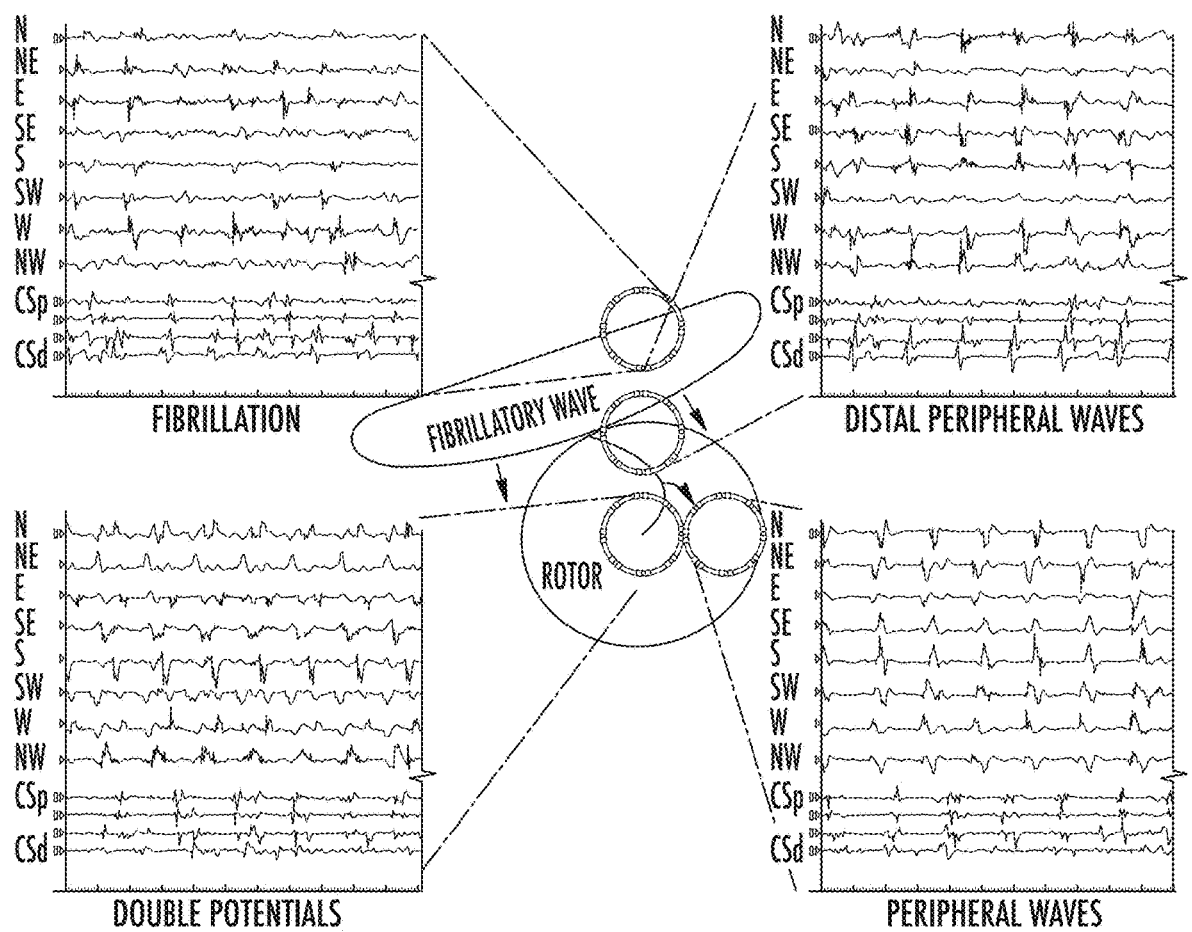
FIG. 21 presents a trace including double potentials for a rotor directly between narrow-adjacent bipolar pair electrodes as schematically illustrated.

A rotational circuit, whether rotor or reentry within the perimeter of the circular mapping catheter would be expected to exhibit double potentials of alternating slope (FIGS. 2F, 2G, 2H). A rotational circuit outside the perimeter should result in a wavefront that passes through the perimeter with a single activation pattern that identifies the wavefront direction as it passes under the circular catheter. FIGS. 2F, 2G, 2H. Diagram of a counterclockwise rotor that exhibits DPs of alternating slope in compass-mode mapping. The gray spiral rotor has its advancing head at darkest gray curve. Arrow showing wavefront spiral direction) with core near the center of circular catheter with wavefront passing opposite sides of the compass. FIG. 2F. The wavefront spiral passes electrode 6 of the cross circle bipolar pair (6,13), SW on compass. The SW tracing shows a positive deflection. FIG. 2G. One half cycle later, the wavefront spiral passes the electrode 13 of the cross-circle bipolar pair (6,13). The SW tracing now shows a negative deflection since the wavefront is in the opposite direction compared to ½ cycle earlier. FIG. 2H. The 2 tracings below show the recordings from the SW direction with alternating DPs, while only single activation wavefront is recorded from the narrow-adjacent bipolar pair (1,2).

All patients were mapped while in atrial fibrillation prior to ablation. In one patient (patient #2), at the time of catheter entry, despite multiple aggressive pacing techniques, AF could not be induced into sustained epochs long enough to adequately map. His mapping data was not included in the analysis. Another patient (patient #20) was in an atypical perimitral flutter at the start of the case. He was mapped while in atypical flutter and this information is being submitted as a case study. His data is not included along with the other 20 patients.

A LA 3-D atriography image (EP Navigator, Philips) was created in each patient just prior to induction of anesthesia. The 3-D map was merged into CARTO® Biosense Workstation. After transseptal puncture the circular mapping catheter was placed into the LA. The catheter was positioned at each of 12 locations of the LA. Just prior to the recording at each LA site, electrode numbers 1,2, were confirmed to be aligned with electrode 17, 18 to maintain consistent circle size. This properly oriented all electrodes as a compass. Sixty-second recordings were completed from each of the LA sites. Simultaneous unipolar and narrow adjacent bipolar electrode recordings were obtained in the last 5 patients with either jpg or mp4 files. These recordings were synchronized to the recordings on the GE workstation by placing 3-5 V-paced beats at the start and end of each one-minute epoch.

Wavefront Activation Pattern Definitions

Activation patterns of the areas mapped by the circular catheter were analyzed off-line, cycle by cycle. In FIG. 2I, and similar to what others describe, but with the addition to DPs, we designated patterns of activation as either DPs, PWs, distal peripheral waves (DSPW), or fibrillatory conduction (Fib). PWs were designated if at least 5 sequential cycles recorded a similar morphology and wavefront direction and separated between cycles with quiescent electrical activity. Cycle measurements continued until there was a sudden change in waveform morphology or direction. Cycle lengths continued to be measured for that epoch pattern if there was as shift to an adjacent compass direction sources, as what might be expected during precession (meandering) of a possible rotor core (i.e., N=>NE). CL measurements ended for this event if the shift was not to an adjacent directional vector (i.e., N=>SW). Similar to PWs, a DSPW identified regions where cyclic wavefronts had similar morphology and direction for at least 5 cycles, but at least one additional wavefront, a secondary wave, that prevented an isoelectric phase between cycles of the primary wavefront. The secondary wavefront(s) could not have a 1:1 association with the cycle lengths of the primary wavefront. Double potentials (DPs) were designated as a wavefront pattern within the region that displayed two distinct wavefront activations. The primary and secondary wavefronts maintained a 1:1 correlation of cycle lengths. To minimize chance of nonrotational causes or competing adjacent cyclic mechanisms of DPs, 5 cycles were required to be categorized as a DP. DPs were described in more detail, having alternating or same slopes, or if cardinal point activations were sequential in time or almost simultaneous. DPs had to be displayed in at ≥2 cardinal directions. Fibrillatory activity was designated for the rest of the disorganized activity recorded that did not fulfill the criteria as discussed above. Cycle lengths, number cycles, total duration, wavefront direct of each pattern were recorded over the minute. Transitions between each type of activation pattern were also tabulated.

To assess inter-observer variability, all double potential sites classified by the primary investigator was reassessed by a second observer (H.Y.). All were confirmed as double potentials, six differed as to the duration of DPs, none more than 2 rotations. Final duration of these patterns was determined by mutual consensus.

FIG. 2I. Diagram of wavefront patterns defined in Methods of compass recordings in different areas over or near a rotor. Each of the 4 recordings show the cardinal compass recordings in the top 8 traces with the next 4 traces recorded from the coronary sinus catheter (CS) from proximal (p) to distal (d). At the top left, fibrillatory (Fib) activity is seen throughout all 8 cardinal directions. At the top right, distal peripheral waves (DSPW) exhibits a cyclic pattern is seen with gradually changing morphology with additional wavefront activation between the primary cyclic activations. The bottom right shows a peripheral wave (PW) that exhibits a cyclic pattern and stable morphology with almost no activation signals between cycles. The bottom left shows the circular catheter that directly overlays a rotor and would show double potentials (DPs) in many, if not all cardinal directions. B. Shows cumulative data wavefront patterns over 20 patients in the 12 different LA sites. LA site #7 (LSPV ostia) and site #10 (roof) showed highest percentage of DPs.

Analysis of Transitions between Double Potentials and Peripheral Waves Simultaneous unipolar, narrow bipolar, and wide cross-circle electrodes were recorded during this transition in 4 patients analyzing a total of 28 rotational events at the transition. The 5th patient had perimitral flutter. The presence of a rotational activation, parallel to the plane of endocardial surface, was defined similar to Ghoraani et al. We utilized the criteria of sequential activation along the 16 electrodes around the perimeter of the circular catheter, where head-meets-tail, and >2 rotations. We added further stipulation that time gap between any 2 adjacent electrodes was ≤50% of the cycle length, as will be discussed below. Two separate recording systems were required to confirm DPs by compass and unipolar recording. Additional data of from the narrow adjacent bipolar recordings allowed simultaneous verification of local activity at the N and NW compass poles (FIG. 2C).

Statistical Analysis

Data were expressed as mean±SEM and were compared between study groups with the use of one-way ANOVA. Probability value of $P<0.05$ were considered statistically significant.

Results

Compass mapping utilizing cross-circle paired electrodes identified rotational activity whether from microreentry or rotor activity in the recognizable form of double potentials. A total of 235 sites utilizing the compass mapping method recorded regional AF out of a possible 240 sites. A stable position with good electrode contact was maintained for the 60 seconds of recording at each of the sites. Anatomic constraints, a thin flat atrial chamber, prevented stable recordings from sites 4,7,8,9 from patient #5, site 8 from patient #8.

Distribution, Prevalence and Cycle Lengths of Wavefront Patterns

Figure 2J:
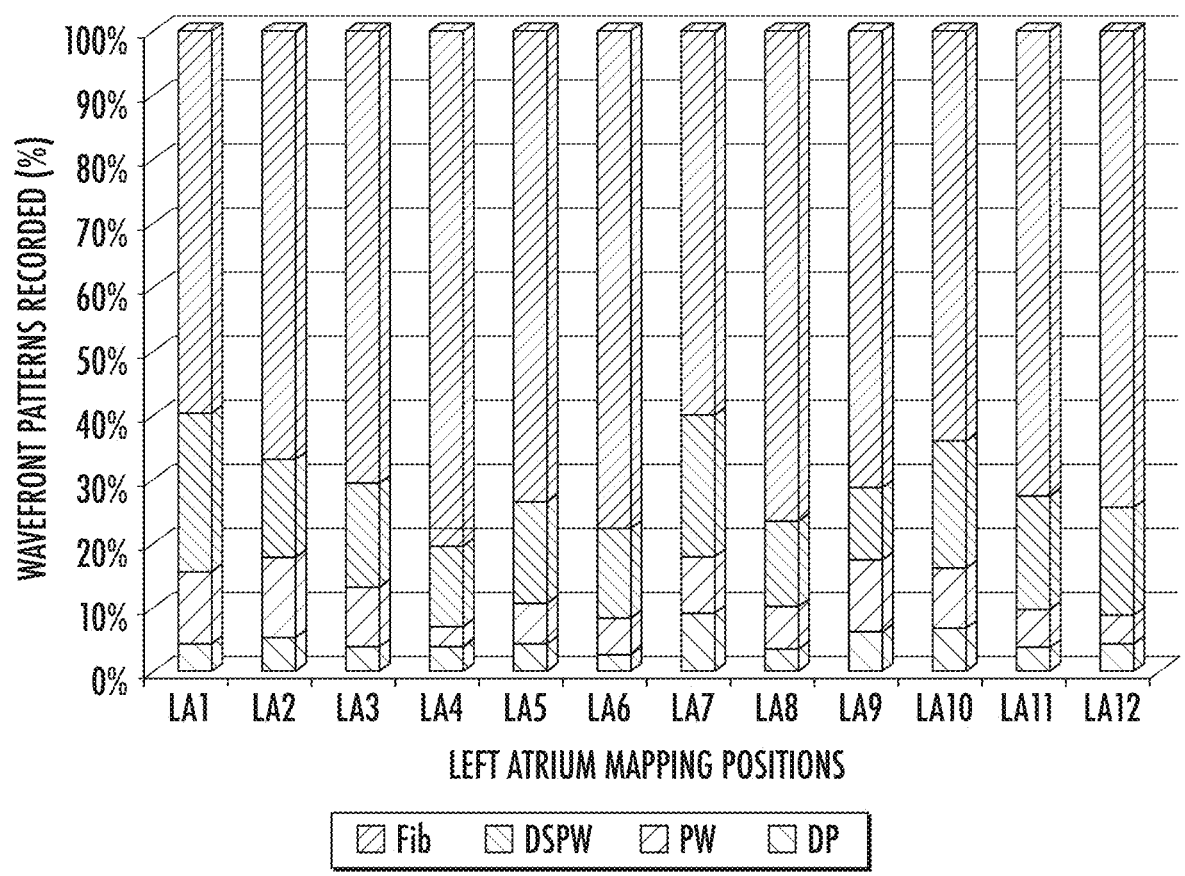
FIG. 2J represents in bar graph form the distribution of wavefront patterns seen at each of 12 locations referenced per the graphs of FIG. 2I.
Figure 2K:
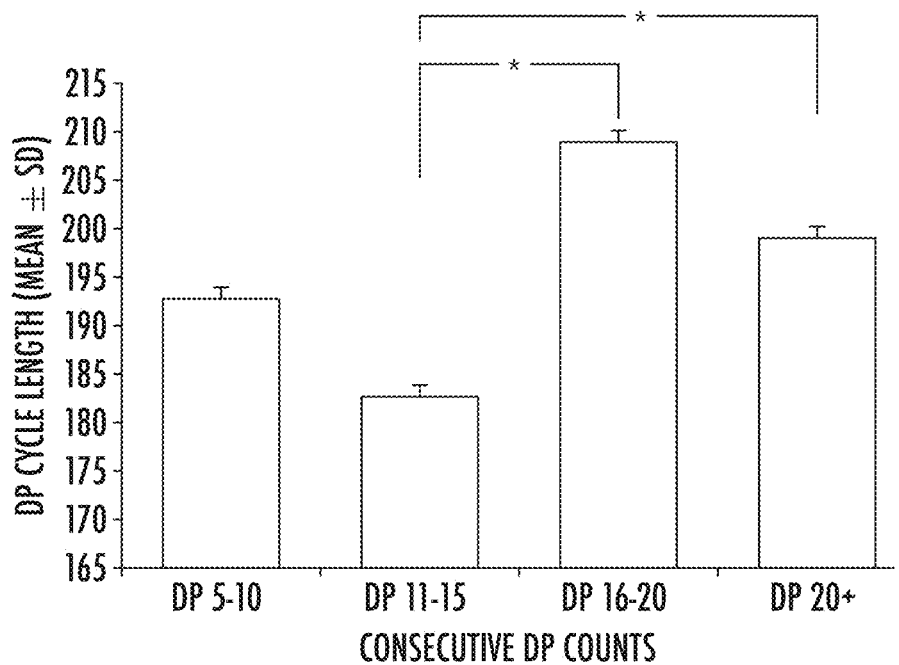
FIG. 2K is a graphical representation of comparison of local stability by consecutive DPs at a single LA site.
Figure 5:
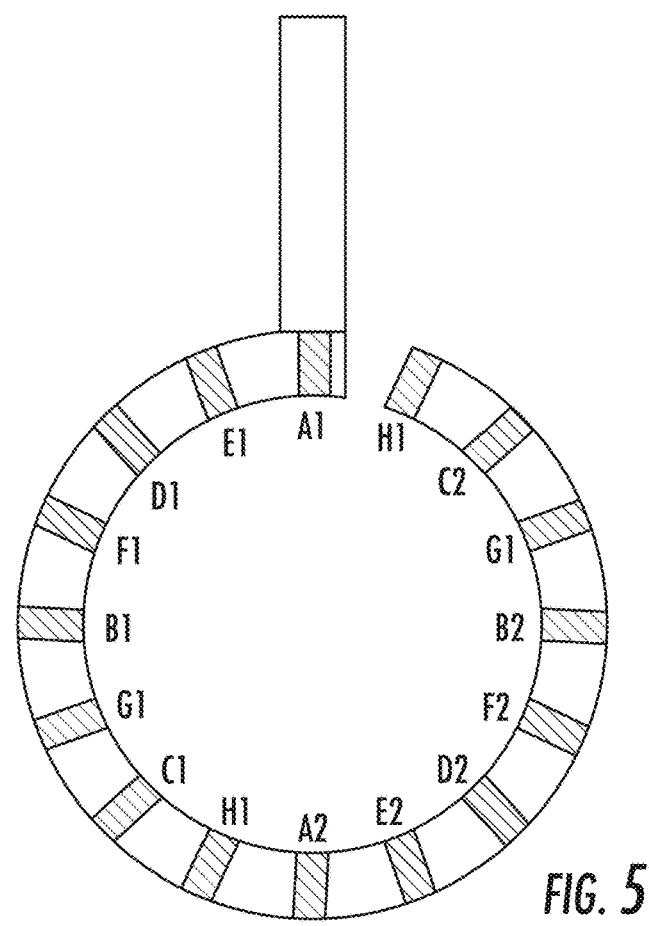
FIG. 5 schematically illustrates another embodiment of a circular mapping electrode catheter as described herein.

FIG. 2J shows distribution of wavefront patterns seen at each of the 12 locations. Highest percentage of DPs were located at Position #7 (9.2%), at the posterior wall just outside the left superior PV. FIGS. 2A and 2B shows how many patients (n) exhibited DPs at a recorded LA site. Most frequent sites exhibiting DPs included left lateral wall, roof, LSPV and RIPV (n=8,7,5,5 respectively). Duration of epochs for continuous DPs prior to transitioning to a different wavefront pattern was separated into bins (FIG. 2K). Most abundant were DP #5-10 cycles (n=82), then >20 cycles (n−38), followed by 11-15 cycles (n=37), and 16-20 cycles (n−16). Long continuous DP epochs were rare to be recorded (n=11 for 10-20 sec; n=3 for 20-30 sec; n=1 for 30-40 seconds, n=1 for >60 seconds). Only 2 patients (Pt #19 and Pt #22) showed 2 LA sites with DPs recorded for >30 seconds. Marked variation is seen between patients in the site location, number of locations and stability. The average number of LA sites that exhibited DPs ion a single patient was 2.9±2.1 with a large range (0-10, FIG. 5B). Patient #14 showed no DPs at any of the 12 LA positions. Only highly disorganized activity with only 1.8 seconds of PWs were recorded from position 1, with all other measurements showed either a DSPW pattern or Fib. At the other extreme, patient #16 had 10 of 12 LA sites exhibit DPs, with the longest total duration identified at LA site #1 for 17.8 seconds.

Figure 2L:
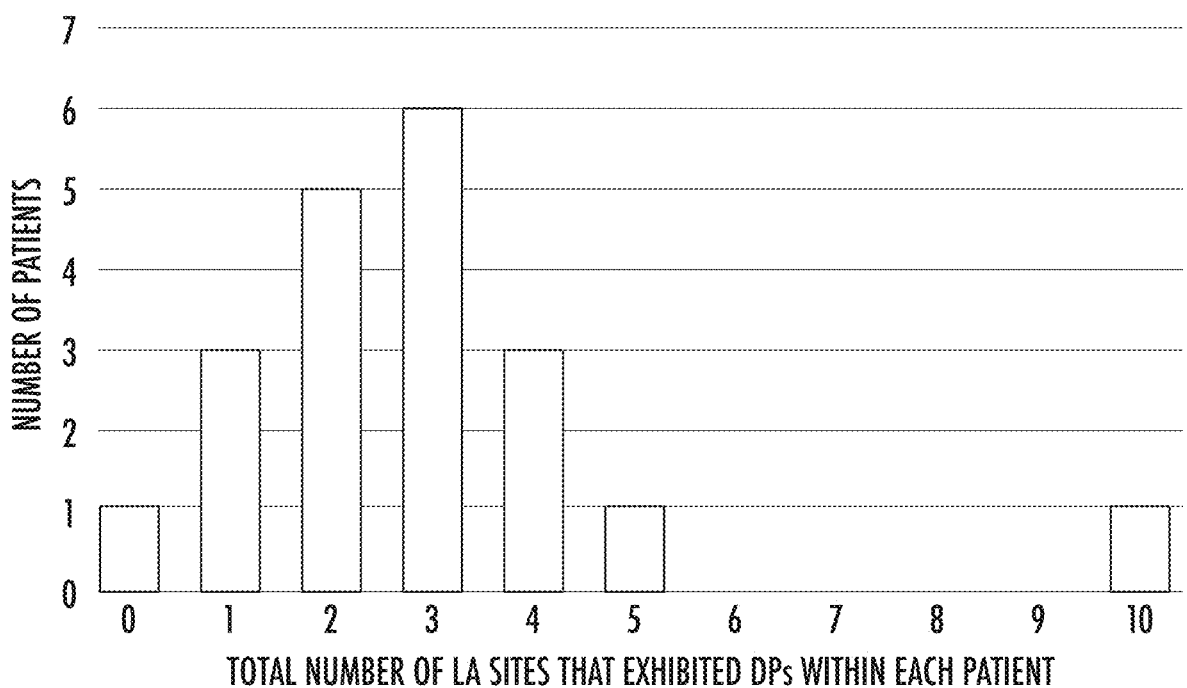
FIG. 2L is a graphical representation of the number of LA sites that exhibited DPs within each test patient (subject)

FIGS. 2K and 2L. FIG. 2K. Comparison of local stability by consecutive DPs at a single LA site. DPs with short cycle count 5-10 were more numerous than cycle counts 11-15, 16-20, and >20 (n=82,37,16, and 38 respectively). Average cycle lengths (CLs) of consecutive DPs were compared between bins of 5-10 cycles (CL=192.9±34.5 msec), 11-16 cycles (CL=182.8±31.4 msec), 16-20 cycles (208.9±36.7 msec), and >20 cycles (199.3±46.2 msec). Epochs exhibiting consecutive DPs of 11-15 cycles had significantly shorter CLs from epochs lasting 16-20 cycles (p=0.02) and epochs lasting longer than 20 cycles (p=0.04). FIG. 2L. Number of LA sites that exhibited DPs within each patient. One patient showed no DPs at any of the 12 LA sites recorded. At the other extreme, one patient had 10 of 12 LA sites exhibit DPs. The average number of LA sites that exhibited in a patient DPs was 2.9±2.1.

Cycle Lengths of Waveform Patterns and Evidence for Rotor Doppler Effect.

Figure 2M:
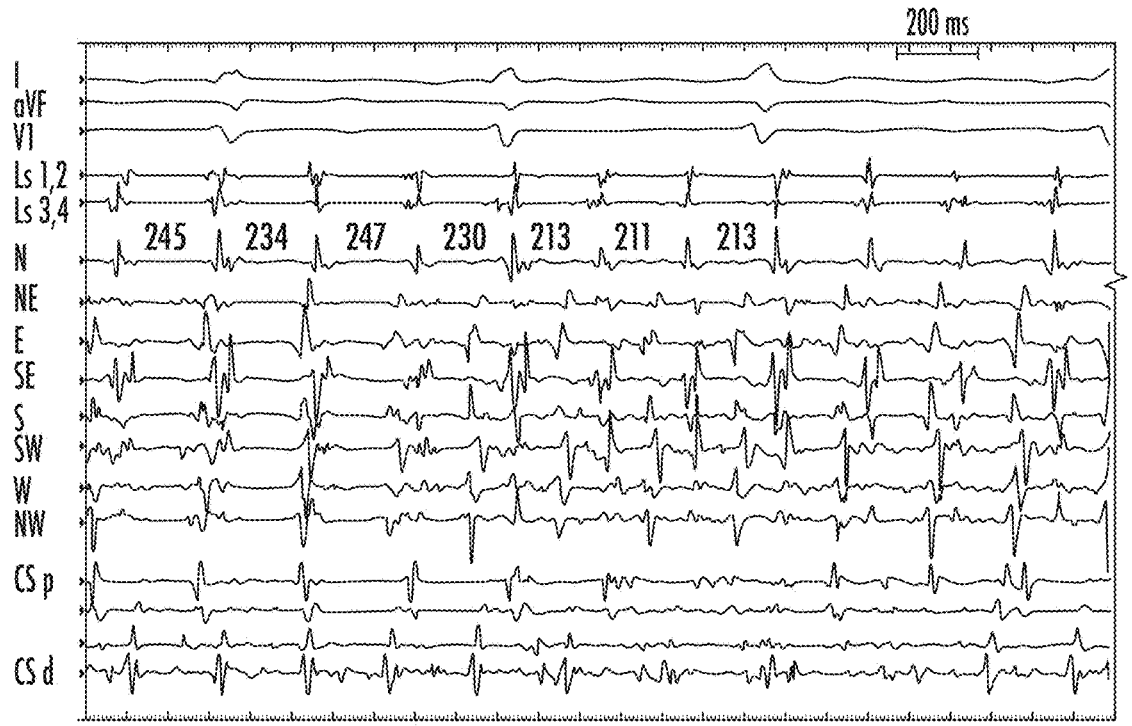
FIG. 2M is a graphical representation illustrating compass mode mapping and reflecting DPs and their association with Doppler Effect.
Figure 2N:
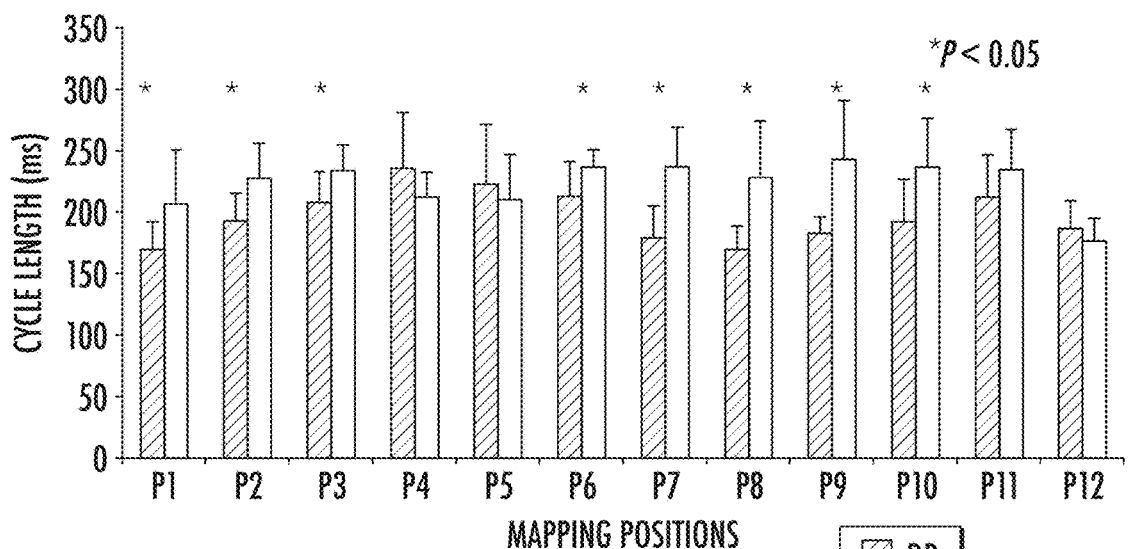
FIG. 2N is a bar graph representation of mapping position-based data.

Many DPs were preceded and or followed by a short period of a PW pattern. Measuring CL at this transition commonly exhibited a shortening of CLs, or Doppler effect on the compass recordings until DPs were manifest. The opposite was noted moving from DPs to PW. FIG. 2M shows an example of CL shortening by about 30 msec as DPs were exhibited. The CL of DP wavefront patterns were evaluated in a matched pair comparison to the CL of PWs from the same LA site (FIG. 2N). Eight of 12 LA sites showed a significantly shorter CL for DPs compared to PWs. DP cycle lengths did not show a significant difference at any of the 12 LA sites when compared to DSPW. Even though an overall Doppler compression of CLs was observed during regional assessment by compass-mode, this was seen to be more complex when observing localized compression of CLs recorded by an electrode on one side of a rotor compared to an adjacent electrode recording expansion of CLs on the other side of the rotor. Further explanation below.

FIGS. 2M and 2N. DPs and association with Doppler Effect. FIG. 2M. Compass mode mapping exhibits a PW across the region of recording, the CL shortens as a rotational mechanisms precess into that region. Top 3 traces show surface ECG leads I, avF, and V1. Next 2 traces show narrow-adjacent bipolar recordings from bipolar pairs (1,2) and (3,4). Next 8 tracings show recordings from the 8 cardinal compass directions using cross-circle bipolar pairs. Last 4 tracings show coronary sinus (CS) recordings proximal (p) to distal (d). Note the marked reduction in CL (msec) with the simultaneous development of DPs in all directions. Also, the single activation in narrow-adjacent pair (1,2) and (3,4), simultaneous to alternating DPs in compass mode, confirm single activation at that side of the compass, and that DPs were secondary to rotation activation to reach the other side of the circle, with alternating and opposite wavefront direction. FIG. 2N. Each LA site was matched paired with PW to DPs. DPs showed significantly shorter CL compared to PWs at LA sites 1,2,3,6,7,8,9, and 10.

Transitions

Recording the transitions between DPs and PWs were most instructive. It might be expected that an approaching rotor prepares or clears the tissue ahead of it by organizing it into PWs prior to precessing into that region. In the 173 recordings of DPs, there was a transition from a PW pattern (n=26, 15.0%), DSPW (n=88, 50.9%) and Fib (n=59, 34.1%). Once in DP, there was a transition to PW (n=27, 15.6%), DSPW (n=69, 39.9%) and Fib (n=77, 44.5%).

In Depth Analysis of DP Transitions and Criteria Development of Rotor Location Perimeter Breech, Activation Sequence Reversal Compression and Expansion Doppler Effects Transitions to and from DPs and PWs were analyzed with simultaneous recordings in compass mode, narrow-adjacent bipolar and unipolar recordings. A diagram is presented first to demonstrate hypothetical geometric and time dependent changes of electrode recordings as a rotor passes between a pair of electrodes (FIG. 2O). A rotor, represented as a clock hand moving clockwise, lies just outside the perimeter of the circular catheter. The wavefront generated from the rotor crosses the two electrodes (e2 and then e1) at times 5 and 7 o'clock respectively as the rotor moves along a path that bisects e1 and e2. The timing of activation at these electrodes moves in opposite direction. The e2 activation signal occurs progressively earlier in the rotation cycle, while the e1 activation signal occurs progressively later. The time lapse between activation signals from e2 and e1 lengthens. If the rotor were to sit at the midpoint between the 2 electrodes, then the time separation between the 2 electrodes would be ½ of a full rotation. If e1 and e2 are electrodes of a bipolar recording, then the activation recordings would result in alternating double potentials (movie1, and FIG. 2P). This leads to an important finding that the narrow-adjacent bipolar recordings can detect crossing the perimeter by a transient DP in that pair just as the cross-circle pairing detects that a rotor has moved within the perimeter. Importantly, once the rotor has moved within the perimeter of the circle, the time gap between the e1 and e2 electrodes would be less than ½ the CL.

Figure 2P:
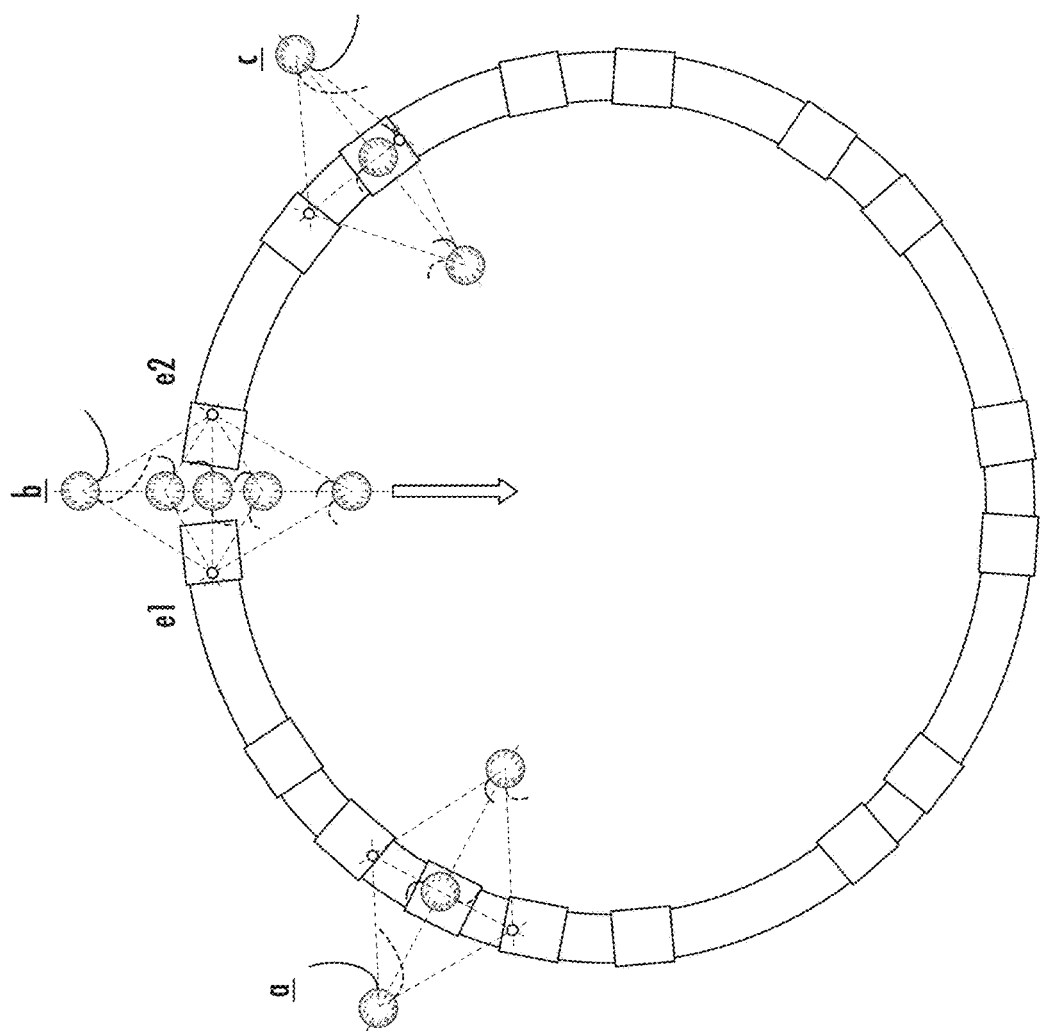
FIG. 2P is a representation of exemplary bipolar electrode arrangements used in providing particular data examples as otherwise discussed herein, and representing three different paths by which a rotor can breach the perimeter of the circular catheter.
Figure 2O:
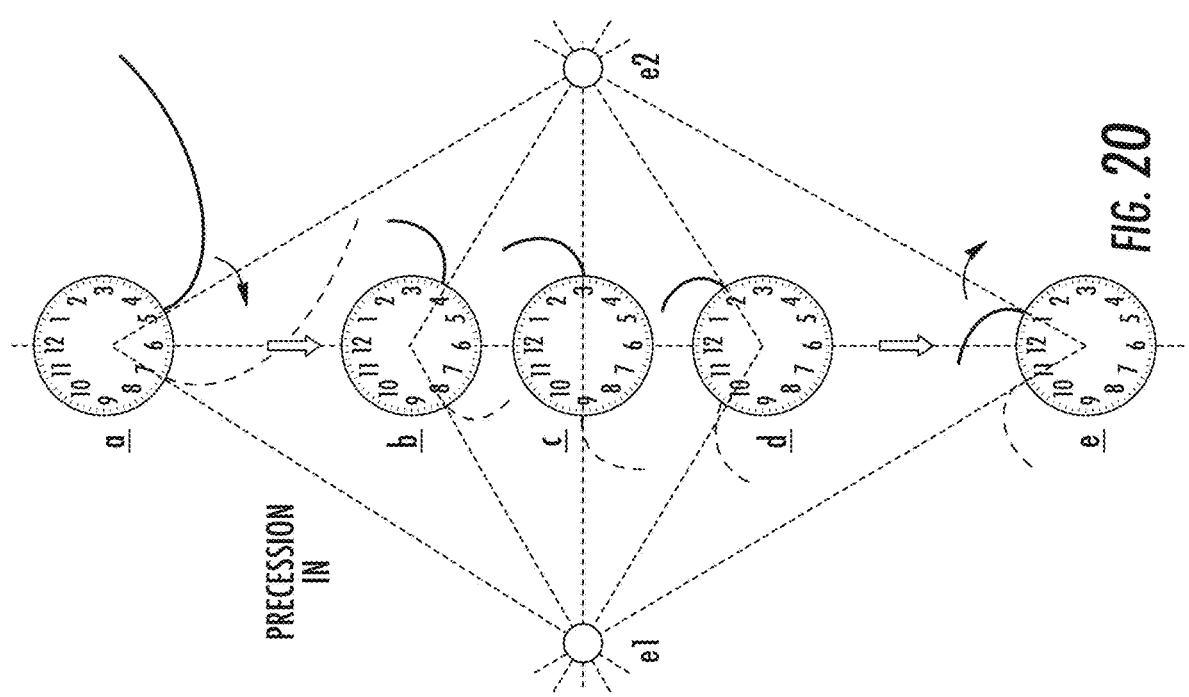
FIG. 2O is a diagrammatical representation of geometric and time dependent changes of electrode recordings as a rotor passes between a pair of electrodes.

FIGS. 2O and 2P. Diagram of differential Doppler effects on electrodes with precession past electrodes. FIG. 2O. A rotor diagrammed as a clock hand circulating clockwise moves on a path that bisects electrode 1 and 2. Electrode 2 is on the side of the rotor which the wavefronts are moving forward, parallel to the precession path. Electrode 1 is on the other side of the rotor which the wavefronts are also parallel to the path of precession but in the opposite, or backward direction. Initially (position a), a spiral wave will transmit a wavefront signal at electrode 2 at 5 o'clock followed shortly by the wavefront signal reaching electrode 1 at 7 o'clock. A moment later (position b), with the rotor closer to the electrodes, the wavefront reaches electrode 2, earlier in time, at 4 o'clock (Doppler compression with a shorter CL), while reaching electrode 1, later in time, at 8 o'clock (Doppler expansion with a longer CL). When the rotor reaches a point directly between electrodes 1 and 2, the wavefront reaches electrode 2 at 3 o'clock and then electrode 1, a full ½ cycle later, at 9 o'clock. If the rotor were to stay at this position, DPs that are fairly equally separated in time would be expected, (see Movie 1). The process continues as the rotor reaches position d and e. When reaching these positions, there is a reversal of sequence, activation at electrode 1 followed shortly by activation at electrode 2. FIG. 2P. Diagram of three paths that a rotor can breach the perimeter of the circular catheter, between 2 pairs of narrow-adjacent bipolar electrodes (a), between 2 electrodes of a narrow-adjacent pair (b), or directly under an electrode (c).

Figure 2Q:
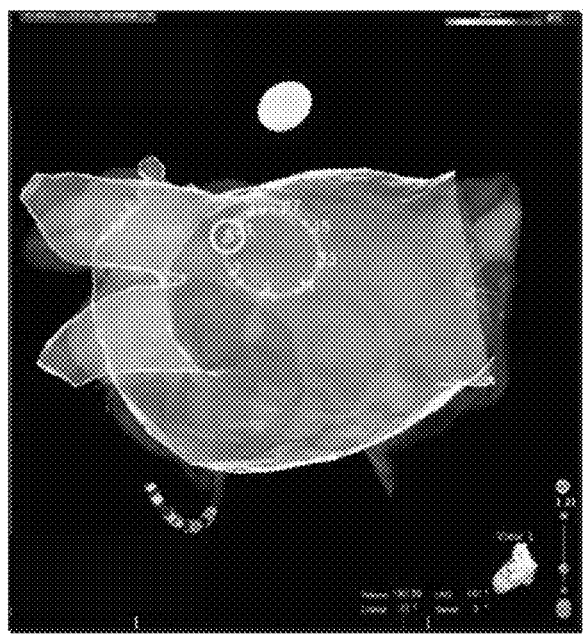
FIGS. 2Q, 2R, 2S, and 2T, variously relate to representations concerning exemplary rotational mechanisms at the perimeter of a circular catheter.
Figure 2T:
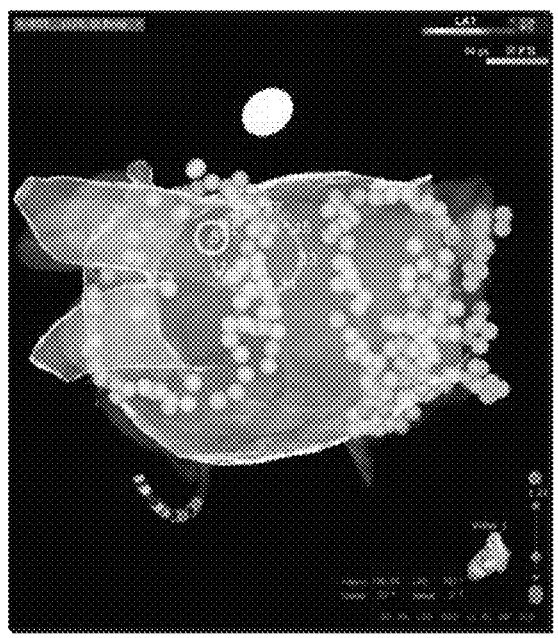
Figure 2R:
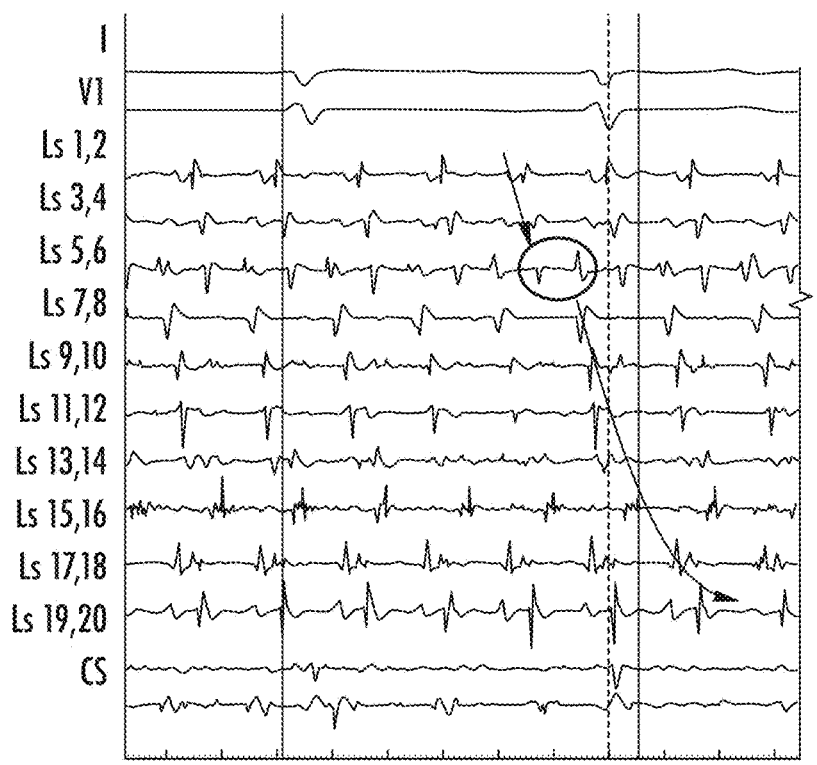
Figure 2S:
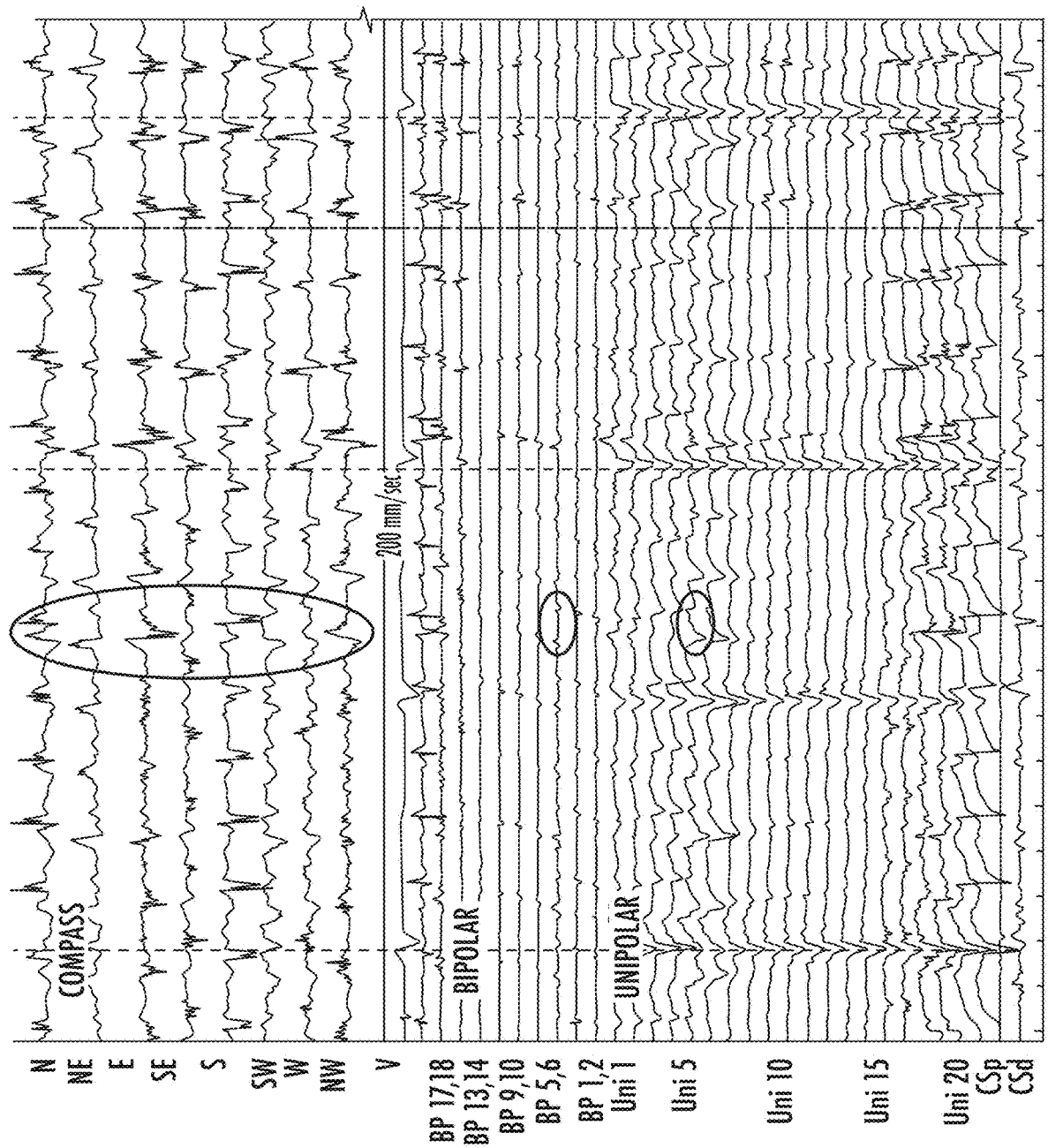

In patient #18, at LA position #7, rotational activity was noted to be slowly transitioning from the perimeter with DPs on all 3 forms of recordings (compass, narrow-adjacent bipolar, and unipolar, FIGS. 2Q, 2R, 2S, and 2T) to a position outside of the compass, generating a PW (FIG. 2S). The PW, identified by the yellow dashed line on the right, shows a wavefront that has earliest activation at electrodes 5,6 at the NE compass point. Two cycles earlier than the yellow line, the largest gap in time is seen on unipolar 6. Note the drop of ½ of the signals from electrodes 6 through 20. This position site as seen in FIGS. 2Q and 2T, was incorporated within the ablation line that circumnavigated the left PVs. Isolation was achieved, Afib persisted. Just prior to completion of the right PV isolation line, AF terminated. This patient has remained arrhythmia free for 22 months.

FIGS. 2Q, 2R, 2S, and 2T. Rotational mechanism at perimeter of circular catheter. FIG. 2Q. 3-D anatomical map with transparent position of circular catheter placed at LA site 7 in patient #18. FIG. 2R. Top 2 tracings show surface leads I and V1. Next 10 tracings show narrow-adjacent bipolar electrode recordings around circular catheter, then unipolar electrodes followed by coronary sinus (CS) proximal (p) and distal (d). The last trace shows recording from CS catheter. Yellow circle shows position of electrode 5 at site of DPs as seen throughout recording of bipolar pair (5,6).

FIG. 2S. Simultaneous recordings at LA site #7 from top: compass map (top 8 recordings), V1 surface recording used to synchronize all recordings with grey-white dashed lines, middle: narrow-adjacent bipolar (middle BP pair 10 recordings), unipolar (bottom Uni 20 recordings) around catheter, and then coronary sinus (CS) proximal (p) and distal (d). The yellow circles show simultaneous DPs in unipolar 5, narrow-adjacent bipolar 5,6, and throughout compass recordings. The yellow dashed line shows the rotational mechanism precessing out away from perimeter of circular catheter as DP pattern switched to PW on compass, bipolar, and unipolar recordings, while the sequential activation gives way to a more vertical alignment. Note that location is corroborated by the largest amplitude, earliest positive deflection occurs at NE-E direction, which is exactly where electrode pairs (5,6) reside. FIG. 2T. Superimposed ablation lesions compared to location of relatively stationary rotational mechanism. Electrode 5 is well within the lesion set to isolate the left PVs.

Our simulation of the activation sequence of a rotor is taken further and breaches a line of electrodes or a perimeter of electrodes around a circular catheter (Movie 2 and Movie 3). This slow-motion identifies an expected pattern of activity that would be specific to a rotor or any rotational mechanisms that moves completely to the other side of the recording line. If a rotor close to the line of electrodes moves along a path towards the midpoint of 2 electrodes, then relative Doppler compression of wavefronts are expected on the electrode receiving the forward moving waves that are parallel to this path. A relative Doppler expansion of wavefronts are expected on the second electrode that is on the opposite side of the rotor. This second electrode receives the backward moving wavefronts relative to the precession direction. At this moment of transition a PW with mostly vertical alignment of activation signals becomes slanted or sequential in alignment where head-meets-tail. That transition, that breach, occurs at the site between the 2 electrodes that exhibit maximal Doppler compression and maximal expansion of wavefronts. This occurs at the moment that activation sequence reverses in direction (movie2 and movie3). Whether precession occurs past a line of electrodes, or along the perimeter of a circle, that transition pattern of Doppler compression and expansion is the same. The progressive delay in activation at the 2nd electrode along with the simultaneous changes in all the other electrodes along the line, results in a unique pattern of activation change that we label as the ½ cycle drop-off. This position and moment in time of sequence reversal, puts a very specific location of the center of rotation. The ½ cycle drop-off would be unique to a rotor or a microreentrant mechanism since it requires the entire circular path to have crossed the line between the 2 electrodes.

Recordings from patient #21 at position 9 (FIG. 2U) shows simultaneous compass, narrow-adjacent bipolar and unipolar recordings of a transition from a PW to DP, and then back to PW. At the moment of wavefront pattern transition occurs in compass mode, the unipolar activation pattern shows the Doppler compression and expansion at poles 12 and 11 respectively, while the same bipolar pair (11,12) exhibit DPs. The ½ cycle drop-off occurs above electrode 10. The opposite transition occurs with precession out from the circle. This pattern repeated a total of 5 times during the 1 minute of recording.

Figure 2U:
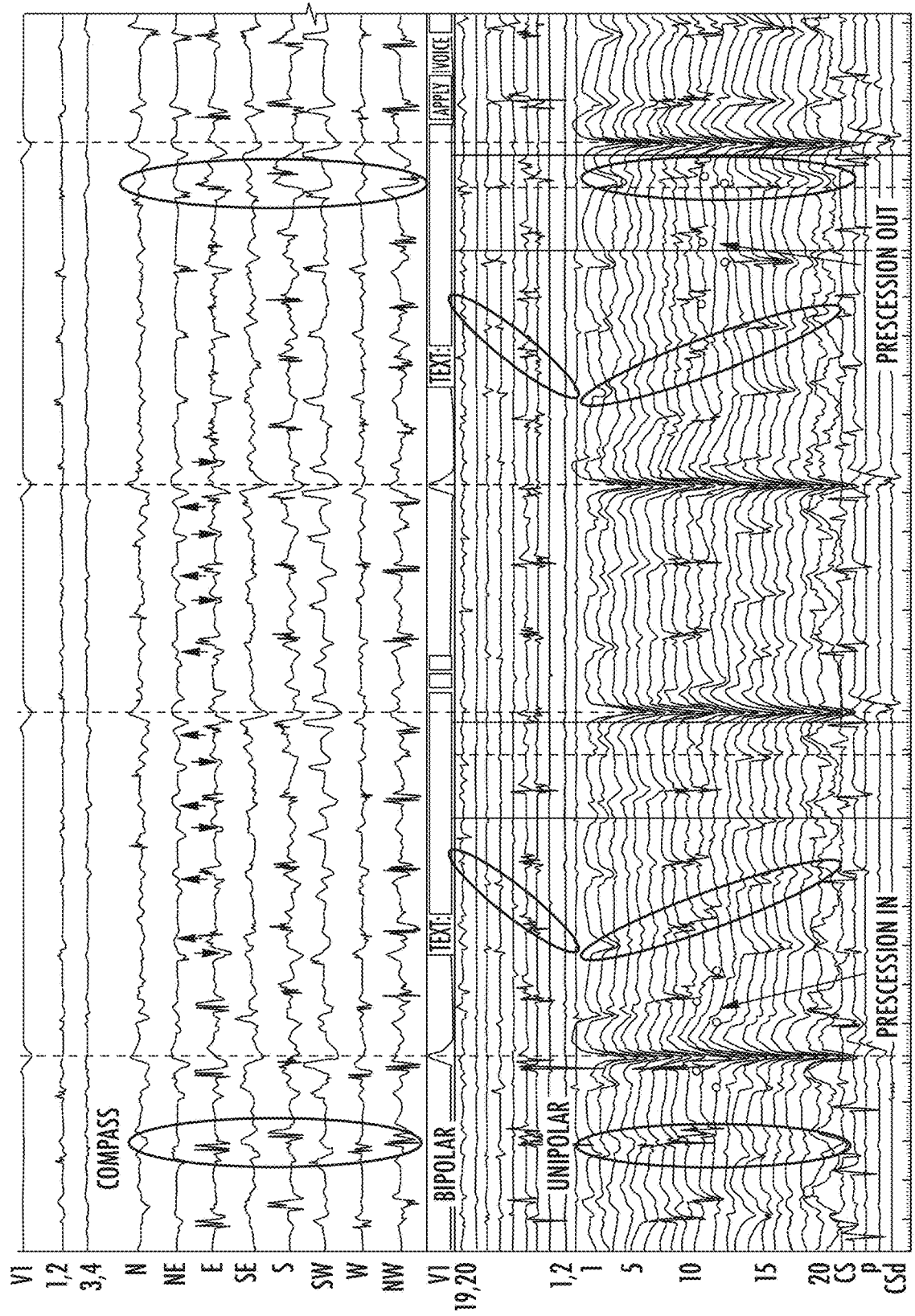
FIG. 2U illustrates representative recordings from a sample subject, showing simultaneous compass, narrow-adjacent bipolar and unipolar recordings involving an event involving a rotor precessing in and out of a circular perimeter of electrodes.

FIG. 2U. A rotor precessing in and out of a circular perimeter of electrodes. Simultaneous methods of recordings were performed at LA site #9 from patient #21. From top: Surface lead V1, narrow-adjacent bipolar pair 1,2 and 3,4, compass recordings (next 8 recordings), narrow-adjacent bipolar pairing 1-20 electrodes, unipolar recordings 1-20, and coronary sinus (CS) tracings proximal (p) to distal (d). Initial wavefront pattern is a PW on compass recordings (black vertical oval) with fairly vertical alignment of bipolar and unipolar recordings. As rotor precesses passed the perimeter, alternating DPs (gold arrows) develop throughout compass recordings while a sequential alignment (slanted white circles), head-meets-tail of narrow-adjacent bipolar and unipolar recordings. A ½ cycle drop off occurs between electrodes 11 and 12. A Doppler compression of wavefronts occur at electrode 12, while there is a Doppler expansion at electrode 11. White dots show the moment that the ½ cycle drop off occurs when the vertical alignment switches to sequential alignment and reversal of activation sequence. The narrow-adjacent bipolar recording shows a DP as the rotor passes between the 2 electrodes. The right-hand portion of the FIG. shows the opposite movement of the rotor passing between electrode 11 and 12. The rotor continues to spin with the same direction. Sequential activation with a slanted head-meets-tail alignment are identified by white slanted circles. As expected, the rotor precessing in the opposite direction of between the same electrode pair exhibits a Doppler compression of wavefronts at electrode number 11, while electrode 12 receives a Doppler expansion of wavefronts (white dots). A DP appears at the narrow adjacent bipolar recording of 11,12 at the moment of ½ cycle drop off occurs and when the PW pattern appears on the compass recordings (black vertical oval). Grey to white dashed lines synchronize unipolars to compass recordings.

Even though we did not have simultaneous unipolar recording of patient #16, the simultaneous narrow-adjacent bipolar recordings from the free end of the circular catheter (Ls1,2) and (Ls3,4) were available to observe. A special transition occurred to and from PW and DP on the compass and ultimately provided a rare look at rotor precession (FIGS. 2V, 2W, and 2X). The simultaneous DPs at the narrow-adjacent pair Ls3,4 coincided with the DPs on the compass in the wider cross-circle (N-NE direction) which is orthogonal to Ls3,4. When the DPs move (presumably the site of the rotor core) to narrow-adjacent pair Ls1,2, the DPs in the compass mode record a transition of the wavefront pattern to PWs. The rotor moved along the line of the catheter, back and forth between narrow-adjacent pairs Ls1,2 and Ls3,4 and exhibited twelve transitions in the first twenty-three seconds of recording, each time coinciding with simultaneous transitions in the compass. The repetitive electrical activation pattern was confirmatory that a rotor precessed back and forth at this location. Bipolar pair Ls1,2 must lie just exterior to the perimeter since when DPs occurred here at this narrow-adjacent pair, only PWs were being recorded on the compass. The equally separated DPs recorded from Ls1,2 are consistent with a rotor just outside the perimeter of the compass. The compass mode recording provides location verification that the rotor exists very close to the perimeter (maximal and earliest positive deflection at the N direction) exactly where these narrow-adjacent pairs of electrodes are located. As soon as the DPs move to bipolar pair Ls3,4, there is a simultaneous switch to DPs within the compass and loss of DPs at bipolar pair Ls1,2. Each transition showed a gain of DPs at one bipolar pair with a simultaneous loss of DPs at the other bipolar pair. This provided a critical form of proof of rotor activity without need to annihilate the rotor. In addition to the remarkable repetitive recording patterns, this recording allowed a unique opportunity to analyze the behavior, morphology and patterns of a rotor (FIGS. 2W and 2X). The electrogram recordings exhibited discreet DPs while at other times, there was a transition to one component of the DP being more uniform while the other became highly fractionated as in complex fractionated atrial electrograms (CFAE). Since the complexity appeared to be asymmetric, far more complex on one of the double potential components, it suggested that the rotor core might be directly beneath just one of the electrodes. If the rotor is in fact moving down the line of electrodes, then the core would be recorded passing beneath. The multicomponent complex fractionated electrogram exists throughout this recording and meets criteria to be considered as a CFAE. CFAEs may be nonspecific but no one knows if that specificity increases when the CFAE is one component of a DP.

FIGS. 2V, 2W, and 2X. Precession of a rotor along a line of electrodes passing back and forth at perimeter at LA site #7 from patient #16. FIG. 2V. Recordings from the top are surface leads I, avF and V1, narrow adjacent bipolar electrode pairs Ls1,2 and Ls 3,4, Compass recordings, and coronary sinus (CS) proximal (p) to distal (d). Simultaneous narrow-adjacent pair of electrodes record DPs between electrode pair Ls1,2 with immediate shift to pair Ls3,4. Each time that DPs appears (top ovals) at bipolar pair Ls1,2, a PW is observed on the compass. As the rotor precesses to the bipolar electrode pair Ls3,4 as seen at the bottom ovals, a DP wavefront pattern is seen throughout compass recordings consistent with rotor within the perimeter. FIGS. 2W and 2X. Expanded version of two of these transitions are seen below. Electrode pairs Ls1,2 and Ls3,4 are the free end of the circular catheter. Wavefront pattern transitions between DP and PW occurred 12 times in 23 seconds. At each moment of transition, there was a simultaneous transition in which the local DP recorded, switched back and forth between narrow-adjacent pair Ls1,2 and Ls3,4. This observation can be explained by electrode pair Ls3,4 at a position just within the perimeter of the cross-circle pairs, while the electrode pair Ls1,2 lies just outside the perimeter. Further evidence of rotor at this site is the simultaneous PW pattern which exhibits largest amplitude, broadest span and earliest positive deflection at the North cardinal point where bipolar electrode pair Ls3,4 resides.

Of the 28 rotational events (56 transitions) identified by sequential activation around the 16 electrodes, 26 had both precession into and out of a PW pattern. Each of the other 2 events had sequential activation preceded by fibrillatory wavefront patterns. Once in a sequential activation, the wavefront pattern transitioned to a PW. 54 out of 56 transitions (96%) each showed the ½ cycle drop off pattern. Seven of these epochs were less than the 5 cycles to be considered by our definition of a DP pattern on compass mapping. An additional 2 events had sequential activation but were at the perimeter with sequential activation (i.e., FIGS. 8B and D), with 50% of CL between 2 adjacent electrodes with DPs noted at that electrode location (both unipolar and narrow-adjacent bipolar). 16 of the 42 DP epochs (either sequential or vertically aligned) recorded in compass mode had either a sequential unipolar activation or a perimeter activation pattern for a positive predictive value of 38%. Sequential activation of DPs in compass-mode (less than a 50% time-gap between all cardinal directions) was seen in 22 of the compass-mode recordings resulting in a positive predictive value of 73% of sequential unipolar activation.

Ablation Results

Ablation data is presented anecdotally. This was a pilot observational study to determine usefulness of DPs in compass mode and in typical narrow adjacent electrode separation to determine regions of rotational activity and to identify electrical patterns of activation directly that will be useful in newer mapping systems. DP data was evaluated retrospectively and assessed off-line. Ablation at sites of rotor activity was only due to it being discovered that that site was incorporated into ablation lines. Patient 18 had the stable rotor at the posterior wall adjacent to the ostia of the LSPV as discussed above. Eight of 20 patients had AF terminate during ablation of PVs with or without additional lines. Fifteen patients are arrhythmia free, five of whom required a 2nd procedure, and one while on additional flecainide. The other five patients with recurrence opted for AVNode ablation with permanent pacemaker implantation.

Discussion

Long term successful treatment of persistent AF by ablation remains elusive. If ablation is to be effective, then improved mapping methods, identification of maintenance mechanisms, and ablation site strategies must all become more accurate. It has been previously suggested that direct electrically mapping of rotors would be nearly impossible due to meandering of the rotating core along with constant changing of electrical waveforms. It has long been known that a rotational mechanism that has a pivot point or its center of rotation between 2 electrodes will exhibit DPs. Therefore, we used the premise that by setting up a perimeter of electrodes, that specific patterned activation wavefronts could detect a breach of that perimeter. Important detailed analysis along the perimeter can specifically locate the core at the time of the breach. The shape of the catheter allows further refinement as to the directional path. Time, location, and path are essentials to proper targeting.

The fastest electrical driving mechanism has remained the goal of ablation and rotor activity has become a primary focus of attention. Potentiometric fluorescent dye used in animal studies of AF created visually appealing color movies of rotor activity. This highly detailed method had a spatial resolution of <0.5 mm to detect local voltage phase differences and therefore provided meticulous descriptions of rotor location, formation and behavior. The inability to use potentiometric dye clinically, along with the preconception that it would be too difficult to record and track rotor activity electrically, basket catheters with complex proprietary computer programs were then devised. Lack of direct recording between splines of electrodes required interpolating algorithms to simulate the animal phase maps and then create movie images. The early success and optimism of ablation with this strategy has been met lately with much less efficacious results. Computational mapping using basket catheters has come under increased scrutiny realizing that large regions of atrial tissue have either poor electrode contact or inadequate electrode spatial resolution or both.

A basket catheter has 8 splines with 8 electrodes along each spline. Ideally, equally spaced splines deployed within a 4 cm diameter LA, would result in electrodes 15 mm apart at the equator. A 5-cm diameter LA is worse with electrode separation between splines at 19 mm. Importantly, a calculation of spatial resolution to reliably detect rotor activity and movement is <14.2 mm. Typically, there is marked variability in the separation between splines, and only 63% of the electrodes met this spatial requirement. Compounding matters, manipulation of the basket to obtain better electrode contact on one side is met with worse electrode contact on the opposite side of the basket. Adequate contact was achieved in 52% of electrodes. Inadequate spatial resolution has led to false detection of rotors. Thus, the initial description of persistent AF having 2-3 stable rotors per patient that meander within a 2-3 cm region of atrial tissue may require modification.

Assessing techniques with other standard mapping catheters, it was surmised that only non-meandering rotors could be localized in the mere happenstance that the catheter lay directly over the rotor. A rotational wavefront, with its center of rotation between a bipolar electrode pair, will record DPs whether the mechanism is reentry or rotor. DPs would be expected to be recorded at a pivot point or surrounding the center of rotation in any 3-dimensional plane. Some rotors can electrically control local tissue with stable centrifugal spiral waves having diameters as great as 6 cm. Modification of bipolar electrode pairing to a cross-circle arrangement provides an immediate compass-like assessment of a 3 $cm^2$ region. A rotational mechanism with its center within the perimeter would be expected to exhibit DPs around the compass and potentially be used as a signal to the operator to look more closely at this region for precession breach sites. We set out to prove that one could identify not only regionally locations of rotational activity, but that specific patterns of perimeter breach could be identified that unlocks the puzzle to localize and track rotor precession.

When DPs were observed in sequence around the cardinal directions during compass-mode mapping, simultaneous narrow adjacent bipolar pairs and unipolar recordings showed sequential activation around the circular catheter in 73% of epochs. The main difference in comparing unipolar sequential activation and DP assessment for rotational activity is the definition for rotational sequential activation around the circular catheter only applies to a rotational mechanism that is parallel to the plane of the circular recording catheter, while recording DPs are not 3-dimensional plane specific. Thus, the 38% positive predictive value of compass mapping DPs of any type (sequential or not) to exhibit unipolar sequential activation is not surprising. In 8 recordings in which unipolar sequential activation was observed, compass mapping did not identify DPs but were identified as DSPW or Fib. This may suggest that the radius of an uninterrupted spiral wavefront was smaller than the circular catheter and that smaller radii electrode catheters might have demonstrated a DP wavefront pattern. If a rotational mechanism exists with its plane of rotation parallel to the endocardial surface and the circular recording catheter, then there are 3 pathways that the rotational mechanism may enter the perimeter of the compass: between 2 electrodes of a narrow-adjacent bipolar pair; between 2 pairs of adjacent pairs (pattern similar to unipolar recordings of all electrodes around circle); or directly under an electrode. We showed examples in actual humans recording of all 3 transitions across the perimeter.

As we showed in simulation and in actual multiple human recordings, a rotor that passes a line of electrodes will exhibit a Doppler compression and expansion with a ½ cycle drop off at the point of breach. This pattern identifies the moment of activation sequence reversal. In the prior study using a circular catheter, the authors attention was focused on the sequential activation. However, it should be noted at the transitions, that the ½ cycle drop-off described here, can also be observed in their FIGS. 3, 4, and 5. Perimeter breach, time, and location are important, but this doesn't answer the question as to its direction. The same result of electrical activation sequence pattern could be obtained with a mirror image of a rotor. For example, a clockwise rotor above a line of electrodes will have the same electrode activation sequence as a counterclockwise rotor beneath the line of electrodes. Both could cross the line at the same point in opposite directions and the same sequence reversal would be noted. Therefore, a second line of reference is needed in the orthogonal direction to determine the path of the rotor. A circular catheter provides a line of electrodes along its perimeter. A narrow-adjacent pair of electrodes provides directional information along one line of axis. The simultaneous wide cross-circle pairs of electrodes provided a second orthogonal line of reference, at all directions around the compass setup. The use of a perimeter of electrodes results in PWs to be exhibited if a rotor or any rotational mechanism exists just outside the perimeter. On the other hand, one will observe DPs in compass mode, if the rotor exists within the perimeter. During precession of a rotational mechanism from outside the perimeter to inside, PWs transition to DPs, while there is a simultaneous switch in the unipolar and narrow-adjacent bipolar electrical recordings from a mostly vertical alignment of activation to a head-meets-tail sequential activation. The circular shape of the catheter provides the important path direction parameter to the specific time and location of the rotor breach. With all 3 tracking requirements met, new targeting and tracking strategies can now be devised.

To distinguish rotor vs reentry, both would show DPs and sequential activation if the rotor was within the circular perimeter or if one of the pivot points of reentry was within the perimeter. However, in the reentrant mechanism, the maximal time gap between adjacent electrodes would never be expected to be less than 50% of the cycle since the last half of the cycle would occur in the region of the 2nd pivot point outside the circular perimeter. If the rotational mechanism was a microreentrant mechanism that was encircled completely by the circular catheter, then this might be indistinguishable from a rotor. Importantly, Doppler effects are expected with rotor activity but not reentry. Thus, regions that exhibit DPs that were caused by rotors would be expected to have shorter CLs compared to PWs. The significantly shorter CLs that we observed in most LA sites compared to PWs suggest that DPs were secondary to rotor activity. It might not be clinically important to distinguish rotor from microreentrant if both are a driving force of arrhythmia and the focus is more towards its location to target for ablation.

We summarized the transition from PW to DP in all 3 recording methods in Table 3. Based upon our findings, we suggest the following required criteria of locating and targeting electrically a migrating rotational mechanism:

1. Identify the site of breach along on a line of electrodes, or a breach in its perimeter.
   a) Determining the spot along the line of electrodes where there is the maximal time gap (50%) between adjacent electrodes in unipolar, or equally split double potentials in narrow-adjacent bipolar recording. The site will be between maximal Doppler compression and Doppler expansion.
   b) A transition is seen when a reversal of activation sequence occurs.
2. A ½ cycle drop-off pattern helps to recognize that the rotational mechanism is completely on the other side of the perimeter at the moment of activation sequence reversal.
3. A second line of reference is required to determine direction of migration, a circular catheter shows which side by a transition from a mostly vertical alignment to a slanted sequential, head-meets-tail alignment of activation, or as a PW transitions to DP in compass mode.
4. These criteria can be repeated through a family of electrodes to then accurately track a path and life of a rotor.
5. Expansion of a family of electrodes either epicardially or on the body surface would be expected to help identify rotational mechanisms not parallel to the endocardial surface.

TABLE 3

| Location | Cross-Circle Bipolar COMPASS | Adjacent Bipolar | Unipolar |
| --- | --- | --- | --- |
| Outside Perimeter | Mostly vertical activation sequence alignment (PW) Sweep across compass has largest amplitude parallel to wavefront | Mostly vertical activation sequence alignment (PW) Sweep sequence across electrodes according to rotational direction (clockwise or counterwise) | Mostly vertical activation sequence alignment (PW) Sweep sequence across electrodes according to rotational direction (clockwise or counterwise) |
|  | Earliest, largest amplitude (+)ve slope provides wavefront origin direction | Earliest activation site provides wavefront origin direction | Earliest activation site provides wavefront origin direction |
| Perimeter/Transition | Activation sequence is a double slant 50% gap between double slants Doppler shortening if approaching DPS in most of cardinal directions | Activation sequence is slanted alignment 50% gap in activiation sequence at breach site Doppler compression/ expansion DPs w/wo CFAE at breach site a) Between 1 pair, or b) Between 2 pairs, or c) Over one electrode | Activation sequence is slanted alignment 50% gap in activiation sequence at breach site Doppler compression/ expansion DPs w/wo CFAEs at breach site between 2 electrodes |
|  |  | Transition ½ cycle drop-off* | Transition ½ cycle drop-off* |

TABLE 3-continued

| Location | Cross-Circle Bipolar COMPASS | Adjacent Bipolar | Unipolar |
|---|---|---|---|
| Inside Perimeter | Sequential DPs Many forms | Sequential Activation around perimeter with <50% CL between any pair of electrodes Reversed activation sequence from other side of breach | Sequential activation around perimeter with <50% CL between any 2 electrodes Reversed activation sequence from other side of breach |

Table 3. Summary of waveform patterns compass, bipolar and unipolar electrodes record an approaching rotor that breaches the perimeter of electrodes and identifies the location of the core.* The ½ cycle drop-off pattern is the key observation that distinguishes a rotor, or microreentrant mechanism from a reentrant mechanism with a line of block traversing a perimeter of electrodes with one pivot point within the perimeter. Although DPs would be expected in both situations, only the complete rotations of the rotor or microreentrant would complete the reversal of activation sequence and create ½ cycle drop-off.

We studied LA sites to specifically detect DPs within 12 specific locations. The circular catheter provided consistency in electrode contact stability, reliable electrode separation distances (regardless of LA size), and ability to record from nearly all areas of the LA. Clearly, we were disadvantaged, by the inability to record from all regions of the LA simultaneously. Analyzing the 1-minute epochs, cycle by cycle, allowed us to observe patterns of activation and precession that were consistent with other investigator descriptions. Presence or absence of DPs provided statistical information regarding that specific region. However, patient #6 provided some important insight into the duration of recordings. In the minute that we recorded from LA position #8, the entire minute exhibited only fibrillatory activity. Just prior to moving the catheter to the next LA position, DPs emerged and a full second minute was recorded, but not included in the statistical analysis. In that 2nd minute, seven epochs of DPs were recorded ranging from 866 msec to 9152 msec (5 to 49 rotations). DPs, PWs, DSPWs and Fib were recorded representing 38.4%, 5.6%, 5.5%, and 50.5% respectively. This begs the question then, how much time is adequate to record? Studies using different methods, different catheter types, utilized different epochs of analysis. Only 2.5 seconds were recorded from sites in a circular catheter study of activation sequence, 4 seconds by basket catheter use in CFAE, 5 seconds in a point by point catheter tip measurement for dominant frequency, 8 seconds in a Pentaray study of Shannon entropy, 10 seconds in an epicardial high density electrode plaque, 1 minute in basket catheter phase map, and 5 minutes using a spiral catheter to measure CFAE. We clearly have an incomplete and inconsistent picture of persistent Afib.

We did not statistically study CFAE sites, but we repeatedly observed their appearance in our study. CFAEs have been recorded at pivot points but may also occur in regions of slow conduction. CFAEs were studied with Shannon entropy, during phase mapping, and epicardial mapping, none of which showed close correlation with sites thought to be important to target for ablation. As was observed in several patients, CFAE was often seen as one of the components of DPs in the narrow-adjacent bipolar electrode pair at the precession breach site, with a rare continuous recording at a breach site in patient #16 (FIG. 2U). The fact that the CFAE migrated as a component of the DP is especially interesting. CFAEs also appeared in other electrode recordings at a significant distance from the breach site. A future study might assess whether CFAE as a component of a DP to be a more specific signature of a rotor core.

The time perspective of direct electrical rotational epochs however should not be lost when comparing these results to indirect interpolated phase mapping. Narayan et al. has described rotors as being stable lasting at least tens of minutes and precessing within regions of 2-3 cm$^2$. The circular catheter used in our study has a 3 cm$^2$ area of coverage. Detailed off-line compass recordings, cycle by cycle, and more refined narrow-adjacent bipolar and unipolar recordings found long running epochs, but these were quite rare. Only 5 patients (25%) showed epochs lasting 20 seconds or greater. Yet, similar to their study, we found between 2-3 LA (2.9%) sites per patient that showed evidence of rotational activity. However only 2 patients (10%) had DPs recorded for >30 seconds, and only 1 patient exhibited DPs for the entire minute. Our findings of very frequent short rotational epochs are consistent with more recent investigations.

Conclusions

Our methods of studying DPs provided the ability to have stable local contact, high electrode resolution, and consistent shape, that allowed us to recognize electrical patterns of rotational mechanisms during atrial fibrillation. These recordings, we believe, are the first to identify specific electrical patterns of rotor activity and behavior as it breaches a line or perimeter of electrodes. By our findings, we also believe that now have the fundamental tools to electrically map and track rotor activity directly without need for interpolation. This study was conducted using standard recording methods, but it required very time-consuming off-line analysis. Technological improvements with better high dense electrode resolution will be needed to create higher quality, efficient mapping techniques. Since stable rotors of long duration, limited precession appears to be rare (5-25%), then at the current state of technology, the compass map method might be used to quickly survey the atrium. Compass mapping might allow for time and cost-efficient targeting of the rarer low-hanging fruit without need of proprietary software and basket catheters.

The frequent short duration epochs of rotational activity with precession requires a paradigm shift in thought, investigation, and ablation strategies. Without more detailed mapping, our current methods used for ablation in patients with persistent AF is more a "Whac-A-Mole®" technique on a KLINKO™ game. Now with the building blocks to electrically record directly rotor location and path by using the electrodes as sensors of a perimeter breach, specific customized maps could be created. More importantly, the life cycle of a rotor could now be assessed from the time of spawning of vortex shedding to migration, to anchoring, to its final demise. In 2 patients of detailed unipolar and narrow-adjacent bipolar recordings, sequential activation was not preceded by precession from a PW and appeared to emerge from fibrillation. If this was a site of vortex shedding, then a preceding Fib recording directly into sequential activation, head-meets-tail, might identify common sites of rotor births. Ablation sites of regions of vortex shedding might be as important as the ablation lines used to isolate sites of ectopic impulses, or sites of rotor anchoring. In addition, studies are needed desperately to evaluate directly different ablation patterns on atrial tissue substrate and its effect on rotor precession. The goal of ablation should be to optimize highest recovery of normal propagation with least loss of tissue and conduction velocity.

Limitations

DPs were examined from cross-circle compass mode, narrow-adjacent bipolar, and unipolar recordings focusing on rotational mechanisms and transition pattern of activation. We only recorded from the LA; therefore, we do not know if longer duration rotor activity from the right atrium would have impacted the prevalence of rotor sites. We did not analyze for possible ectopic sites of activation and this would have been recorded as PWs. Whether PW was a result of an ectopic focus or from a nearby rotor will be a subject of future investigations. We utilized a circular catheter that we purposely kept the same dimensions to provide consistent cardinal directions of a compass. A rotor with a smaller radius of wavefronts that morphed into fibrillatory activity would have been detected as a DSPW. A smaller size catheter may have improved detection, but we would have lost tissue coverage. We did not record simultaneously from all left atrial sites, so it is not known if this would result in under or overestimation of rotor activity. Finally, our recording figures, as in all publications, were selected with the least noise, best amplitudes. There is a selection bias on these figures by all authors to convey their clear thoughts and results to the reader. Therefore, in real-time, the recording of short epochs, pattern recognition, perimeter breaches, all would be present and gone, literally in the blink of an eye. Reliance on current computer interpolating algorithms may be premature. Mapping and targeting AF remains at its infancy.

Movie 1. Slow motion activation patterns as a rotor is positioned directly on the perimeter between a narrow-adjacent pair of electrodes. Two activations occur with each rotation, creating double potentials.

Movie 2. Slow motion activation patterns of a rotor precessing passed a line of electrodes. Doppler compression, expansion, reversal of activation and the ½ cycle drop off.

Movie 3. Slow motion activation patterns of a rotor precessing passed a perimeter of electrodes. Doppler compression, expansion, reversal of activation and the ½ cycle drop off.

With reference to FIGS. 31 through 37, as a rotor approaches a perimeter of electrodes on a path that will cross between 2 adjacent electrodes, then the time gap of recording the electrical depolarization wavefront increases between those 2 adjacent electrodes while recording as 2 unipolar electrodes. As the rotor approaches those same 2 electrodes, and recording as a single bipolar recording, the recording shows a split into double potentials. The double potentials become near equally split when the rotor is directly between them. At this rotor position with the two electrodes straddling either side of the rotor, then in a unipolar recoding, once one unipolar electrode records a wavefront activation, the rotor must spin a full 180 degrees before the 2nd electrode records the wavefront. This is the maximal time gap between the 2 electrodes. All other electrodes along that perimeter line will not have that level of time gap between any 2 adjacent electrodes. Also, with a rotor at the perimeter, only one bipolar pair will show the DPs. Once inside the perimeter, the cross-perimeter bipolar recordings become DPs.

The present disclosure is generally directed to devices and methods for mapping cardiac tissue. More specifically, disclosed methods and devices can be utilized to detect the direction and/or source of a depolarization wave front associated with cardiac arrhythmia. For instance, by use of the disclosed methods and devices, a rotor source location can be identified. Following identification and mapping, the rotor source can be ablated, leading to decrease in arrhythmic episodes and longevity for arrhythmia-free periods.

A mapping catheter as disclosed herein includes a plurality of bipolar electrode pairs (at least two bipolar electrode pairs) in an electrode array. Each bipolar electrode pair includes a first and second electrode. The bipolar electrode pairs of the array are located with respect to one another such that the individual electrodes of the pairs together define a perimeter, e.g., a circle, an oval, or any other perimeter. In addition, the first and second electrodes of each bipolar electrode pair can be located such that they are opposed to one another across the area that is surrounded by the perimeter (also referred to herein as the central area). For instance, in one embodiment, the electrodes of the bipolar electrode pairs can together define a circular pattern. In this embodiment, each member of each bipolar electrode pair can be diametrically opposed to one another across the area that is surrounded by the circular perimeter.

It should be understood that while much of the following discussion is directed to a circular perimeter defined by the electrodes of the bipolar electrode pairs, the disclosed methods and devices are in no way limited to circular perimeters, and the electrodes of the bipolar electrode pairs can together define any perimeter shape including circular, elliptical, ovoid, a perimeter with no clearly defined shape, or any other shape. The perimeter can define an enclosed area and this area can include a center that is equidistant from opposing points on the perimeter. For instance, with regard to a circle or an ellipse, the central area can include the center point of the area surrounded by the perimeter.

The opposing arrangement of the bipolar electrodes can be utilized during vector analysis of the electrical signals to identify directional paths of moving electric fields or wave fronts in any direction passing across the endocardial surface.

Bipolar and/or unipolar analysis of the signals from electrodes arranged as disclosed herein can be utilized to provide data concerning a depolarization source. For instance, a combination of both bipolar and unipolar signal analysis can provide a method to track a rotor and to not only identify the specific location at a point in time but also to track local movement (precession) of the rotor through heart tissue in real time. The bipolar data can identify the direction by which a rotor may approach and/or leave a catheter perimeter area. The bipolar data can identify the time at which the rotor has crossed into the area circumscribed by the catheter (or electrode perimeter shape) according to a change in the pattern of signals as described further herein. Upon determination that the rotor is within the circumscribed recording area, unipolar data can then be used to confirm this relative position, and by geometric analysis, the position of the rotor core within the area can be pinpointed with each subsequent revolution.

In one particular embodiment, multiple simultaneous adjacent areas can be examined, and a rotor can be tracked as it passes from one recording area into the next, providing a continuous tracking of rotor motion. Such information may be useful to eliminate potential paths that a rotor can utilize to maintain its existence.

Beneficially, through analysis of the wave front vector, the catheters can be used to identify source locations, as well as types of triggers and/or drivers of cardiac arrhythmia. In one particular embodiment, the catheters can be utilized to identify rotors, but it should be understood that the catheters are not limited to rotor identification/description. A catheter can be utilized to identify location and type of ectopic trigger foci and/or to delineate reentrant pathways that frequently complicate atrial fibrillation ablation.

A catheter can be utilized to differentiate types of arrhythmia triggers and drivers. For instance, by use of a catheter as disclosed herein, different types of rotors can be categorized. In addition, the general location tendencies or rotors and rotor types can be determined. With regard to examination of individual rotors, a variety of characteristics including but not limited to rotational speed, rotational direction (clockwise or counterclockwise), precess direction and precess velocity can be examined. The individual characteristics of a rotor once determined can be compared and contrasted with those of other rotors in the individual, as well as with chronicity of atrial fibrillation, information that can be used to better identify preferred treatment options for a patient.

A catheter including a circular pattern of electrodes as described herein can be relatively small, and thus, less invasive as compared to previously known heart catheters. This can also provide ease in mobility and position adjustment during use, which can reduce mapping time of the cardiac tissue. Reduced mapping time can reduce radiation exposure to patients, as well as require less processing time and memory of the catheter system, both of which provide great benefit.

In one embodiment, the catheter can also be utilized as an ablation catheter. In any case, following identification and classification of the components of complex atrial arrhythmia in a patient a protocol can include targeted ablation of the identified locations, e.g., rotors, ectopic foci and/or reentrant circuits. For instance, following use of a catheter to map the cardiac tissue and identify ectopic triggers, rotor core sources, etc., the catheter can be adjusted as necessary and the targeted tissue can be ablated via, e.g., radio frequency energization of electrodes of the array.

Figure 3A:
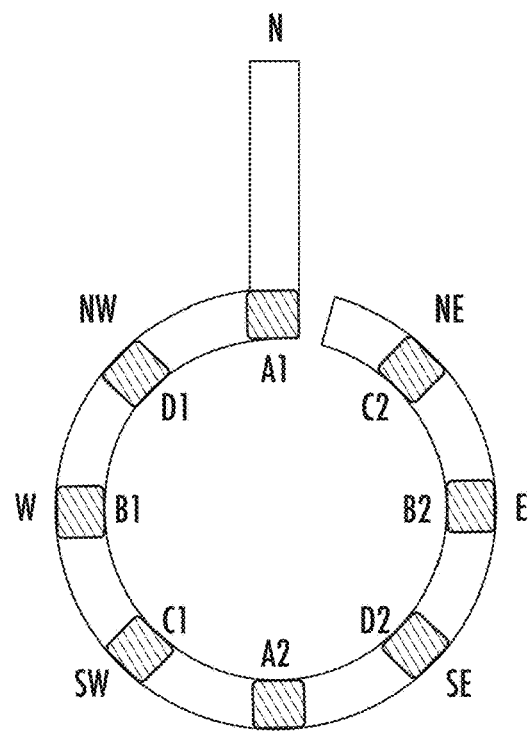
FIG. 3A schematically illustrates one embodiment of a circular mapping electrode catheter as described herein.

FIG. 3A illustrates one embodiment of a circular mapping catheter utilizing an array of bipolar electrode pairs as disclosed herein. In this embodiment, the array of the catheter includes four bipolar electrode pairs (eight electrodes), but it should be understood that an array can include two, three, or more bipolar electrode pairs. In addition, and as described further herein, all or only a portion of the electrodes of an array can be utilized at any one time as the plurality of bipolar electrode pairs that together define a perimeter.

The electrodes of each bipolar electrode pair are in electrical communication with one another and also with processing equipment according to standard practice to form leads that can detect and record the voltage potential difference between members of each pair. In accord with known signal processing techniques, one electrode of the pair is designated as the positive input and the voltage potential of the other member of the pair (the negative input) is subtracted from the voltage potential of the positive input to yield the bipolar potential of the pair. Electrical signal processing equipment, e.g., operational amplifiers, resistors, capacitors, etc. can be utilized according to standard practice to obtain the bipolar potential of each pair with the desired polarity.

Referring again to FIG. 3A, the electrode array includes 8 electrodes in electrical connection with one another so as to form 4 bipolar electrode pairs. The 8 electrodes together define a perimeter (in this case a circle), with the members of each pair opposed to one another across the center of the perimeter. As shown in FIG. 3A, the electrode array includes a first bipolar electrode pair (A1, A2), a second bipolar electrode pair (B1, B2), a third bipolar electrode pair (C1, C2), and a fourth bipolar electrode pair (D1, D2). Note on FIG. 3A that the electrodes of each pair are separated around the circle, with a first electrode of a pair (e.g., A1) across the circle from the second electrode of that pair (A2), and thus, diametrically opposed from its mate. For ease of reference, the pairs can be configured to cardinal positions around the circle like a compass. Therefore, upon location of electrodes and an array in contact with cardiac tissue, vector analysis of an electrical wave front recorded by the four bipolar electrode pairs can provide directional information regarding approaching wave fronts from a north (N), south(S), east (E), west (W), northeast (NE), northwest (NW), southeast (SE), and southwest (SW) direction, as shown.

In the illustrated embodiment, the north electrode A1 of the north/south electrode pair A1, A2 is designated as the electrode position at the top of the circular mapping catheter where the stem shaft of the catheter turns to form the circle portion of the catheter. The cardinal direction positions of a set of bipolar electrode pairs carried on a catheter can then be located around the circle by viewing the circle from the position of the shaft. These cardinal points can be utilized to refer to electrode positions for ease of use for mapping and movement of the catheter. Of course, the compass references are for geometric descriptive purposes only and are not related in any fashion to geographic compass points.

The opposed electrodes of a bipolar electrode pair can be separated from one another by a distance of about 1.5 centimeters or more (e.g., from about 2 cm to about 4 cm, in some embodiments), which can be equivalent to the diameter of a circular pattern of the electrodes. For instance, if 8-10 pairs of diametrically opposed bipolar electrodes surround the perimeter a circle with a 2 cm diameter, then this provides about a 10-fold improvement of the electrode density over the same size region of tissue as compared to previously known basket catheters.

Figure 3B:
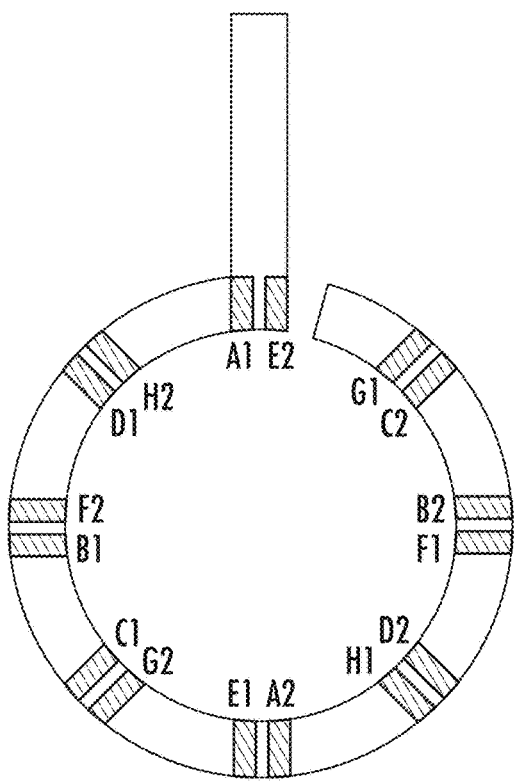
FIG. 3B schematically illustrates another embodiment of a circular mapping electrode catheter as described herein.

The electrodes to be utilized at any one time are not limited to 4 bipolar electrode pairs and a system can incorporate additional bipolar electrode pairs. For instance, FIG. 3B illustrates one embodiment of an electrode array including 8 bipolar electrode pairs (16 electrodes). The electrodes of the catheter of FIG. 3B are mated in bipolar electrode pairs as described above, i.e., A1, A2; B1, B2; C1, C2; . . . H1, H2. In this embodiment, each bipolar electrode pair is associated with another bipolar electrode pair to form an inverse input pair of bipolar electrodes. An inverse input pair includes two bipolar electrodes, and thus, four individual electrodes. Two bipolar electrode pairs that are associated with one another to form an inverse input pair have positive and negative inputs on opposite sides of the perimeter. As such, the signals obtained from the two bipolar electrode pairs will have an opposite initial slope, i.e., one of the bipolar electrode pairs will register a passing wave front with a first slope (e.g., positive) and the other bipolar electrode pair of the inverse input pair will register the same wave front with a second slope that is the inverse of the first slope (e.g., negative). Each electrode of an inverse input pair of bipolar electrodes is located adjacent to and at a relatively short distance from an electrode of the associated bipolar electrode pair, with the positive input electrode of the first bipolar electrode pair adjacent to the negative input electrode the second bipolar electrode pair. Thus, the positive input electrode and the negative input electrode of one of the bipolar electrodes is reversed across the perimeter as compared to the positive input electrode and negative input electrode of the associated bipolar electrode.

By way of example and with reference to FIG. 3B, a bipolar electrode pair A1, A2 is associated with another bipolar electrode pair E1, E2 to form an inverse input pair of bipolar electrodes. As shown, the electrode A1 is adjacent to and at a relatively short distance from the electrode E2 of the inverse input pair. For instance, the distance between the two can be about 5 millimeters or less, or about 3 millimeters or less in some embodiments. In some embodiments, the distance between the two can be from about 0.5 millimeters to about 2 millimeters. In the pair of electrodes A1, A2, the positive input electrode of the pair can be the A1 electrode (at the north position of the array) and the negative input electrode of the pair can be the A2 electrode (at the diametrically opposite south position of the array). In the associated bipolar electrode pair E1, E2 of the inverse input pair, the input electrode is reversed on the perimeter as compared to its associated pair. In other words, for the associated bipolar electrode pair E1, E2, the positive input electrode of the bipolar electrode pair can be the E1 electrode (at the south position of the array) and the negative input electrode of the bipolar electrode pair can be the E2 electrode (at the north position of the array). In this embodiment, the A1, A2 electrode pair can be referred to as the north electrode pair (i.e., the positive input electrode of the two at the north position) and the E1, E2 electrode pair can be referred to as the south electrode pair (i.e., the positive input electrode of the two at the south position).

The other bipolar electrode pairs around the circle pattern can be likewise associated with one another in an inverse input pair relationship. For instance, the B1 electrode can be the positive input electrode for the west B1, B2 electrode pair. The B1 electrode can be adjacent to and relatively close to the F2 electrode, which is the negative input electrode of the east F1, F2 electrode pair. Likewise, the B2 electrode (the negative input electrode of the B1, B2 pair) can be adjacent to and relatively close to the F1 electrode, which is the positive input electrode of the F1, F2 pair. The B1, B2 electrode pair is thus associated with the F1, F2 electrode pair in an inverse input pair relationship. The other electrode pairs around the circular pattern are likewise associated with one another in inverse input pair relationships.

A depolarizing wave front can be detected by an inverse input pair of electrodes with opposite sloping potentials. For instance, the approaching wave front can be recorded with an initial negative sloping potential by the electrode pair for which the wave front passes the positive input electrode first and the negative input electrode second. For the associated inverse input pair, however, the same wave front will pass the negative input electrode first and the positive input electrode second. Thus, the wave front will be recorded with an initial positive sloping potential for this associated inverse input pair. While the two pairs can exhibit opposite direction in the initial sloping potential, they can exhibit essentially the same voltage potential difference magnitude.

The use of inverse input pairs of bipolar electrode pairs and the equal but opposite responses to a depolarizing wave front by the bipolar electrodes can provide high confidence in the wave front characteristics determined by use of the device.

Figure 4:
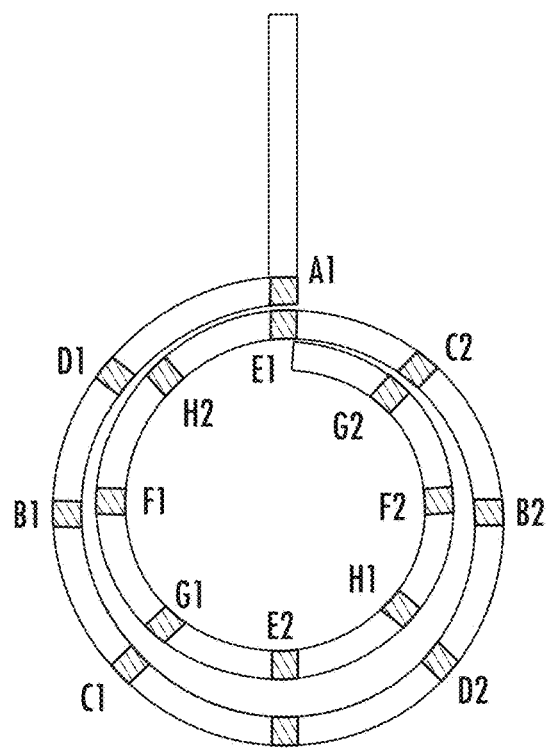
FIG. 4 schematically illustrates another embodiment of a circular mapping electrode catheter as described herein.

A circular mapping catheter can include multiple rings of bipolar electrodes as illustrated in the embodiment of FIG. 4. In this embodiment, the circular mapping catheter can include a first set of bipolar electrode pairs A1, A2; B1, B2; C1, C2; D1, D2 on an outer ring; and a second set of bipolar electrode pairs E1, E2; F1, F2; G1, G2; H1, H2 on an inner ring. As shown, the inner ring can have a smaller diameter than the outer ring, and as such, the diametrically opposed bipolar electrodes of each pair of the inner ring can be closer to one another as compared to those of the outer ring. The use of the different sized rings can be used to improve targeting of the catheter to a particular site, e.g., a rotor core. For instance, the bipolar electrode pair of the outer ring can be initially utilized to encircle a rotor core (details of such a process are described further herein). Following location of the rotor core within the outer circle, the inner ring of electrodes can then be utilized to further narrow the location of the rotor core.

The bipolar electrodes of an electrode array can all be utilized simultaneously during a procedure. Alternatively, a portion of all available electrodes can be utilized during one portion of a procedure and optionally a second portion of all available electrodes can be utilized during a subsequent portion of a procedure. For instance, and with reference to the circular mapping electrode of FIG. 4, all of the electrodes of the inner ring and the outer ring can be utilized simultaneously during a procedure or alternatively, signals from bipolar electrodes of only the inner ring or only the outer ring can be analyzed during one portion of a procedure, with bipolar electrodes of the other ring examined during a second portion of a procedure. Of course, any combination of the multiple electrodes can be utilized during a procedure, provided that the electrodes utilized at any one time together can define a perimeter, with the individual electrodes of each bipolar electrode pair being opposed to one another across the area defined by the perimeter.

An electrode array can include any number of electrodes. For instance, the circular mapping catheter of FIG. 5 includes a single ring that carries 16 equally spaced electrodes in electrical communication with one another that can form 8 diametrically opposed bipolar electrode pairs. Additional bipolar electrodes included in a single ring of an electrode array can increase the detail of information obtained from the catheter during use and the mapping speed of the system. Of course, any number of bipolar electrodes can be included an electrode array and all or only a portion of the electrodes can be utilized at any one time. Moreover, an electrode array can include electrodes in addition to those that are opposed to one another to form the bipolar electrode pairs. For example, an electrode array can include one or more closely spaced pairs as found on a prior art type device, as illustrated in FIG. 1. In one embodiment, an electrode array can include one or more ablation electrodes that are not members of a bipolar electrode pair. Alternatively, one or more of the electrodes of the bipolar electrode pairs can be utilized as ablation electrodes following mapping of a targeted site.

Figure 6:
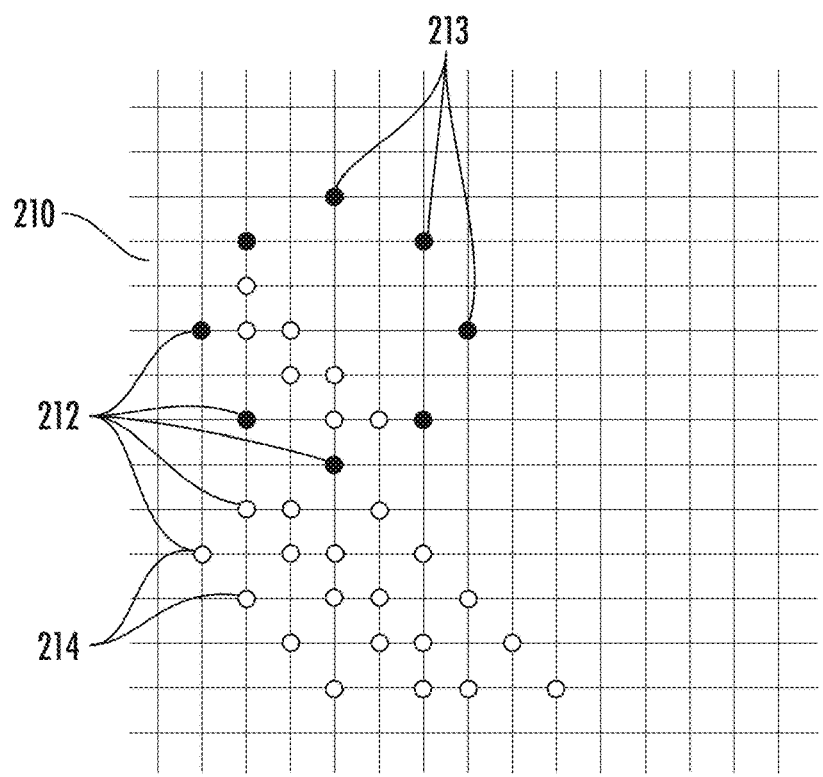
FIG. 6 schematically illustrates one embodiment of an electrode grid for use as described herein.

Any electrode array that can be utilized with a plurality of predefined bipolar electrode pairs as described is encompassed herein, and it should be understood that an electrode array is in no way to be considered to be limited to a circular mapping catheter. For instance, FIG. 6 illustrates a flexible sheet 210 that can include an array of electrodes 212, for instance in the pattern of a grid across the sheet 210. A sheet 210 including an array of electrodes 212 can include a conventional metal, for example gold, for electrical communication between individual electrodes 212. A metal electrode grid can be fabricated using known processes such as standard lithographic techniques, shadow masking, and gold deposition techniques. A sheet 210 can be of any suitable construction and material, provided the material can be utilized in a heart catheterization process. For instance, a sheet can be porous or non-porous formed of any suitable biocompatible material and can include only the electrodes 212 of the grid or can include the electrodes 212 adhered to an underlying substrate.

During use, the signals from a portion of all of the electrodes 212 of the electrode array across the sheet 210 can be measured in a mapping protocol. For instance, in the illustrated embodiment signals from the electrodes 213 marked with solid black designations can be measures while the electrodes 214 marked with open white markings are not utilized. As shown, the electrodes 213 that are utilized simultaneously in a mapping protocol define a generally circular perimeter. The electrodes 213 can be in electrical communication with one another such that there are 4 diametrically opposed bipolar electrode pairs across the circular perimeter. In one embodiment, following a period of time of mapping during which the electrodes 213 are utilized, a different set 215 of the available electrodes 212 can be utilized in a protocol. For instance, the signals from a different set of the available electrodes 215 can be measured so as to map at a different location on the sheet 210 (and thereby, a different location of the contacted cardiac tissue) or so as to form a perimeter of a different size than that of the electrodes 213. Alternatively, the two sets of electrodes 213, 215 can be examined at the same time to provide for simultaneous mapping of two different areas of the tissue. In addition, the two sets of electrodes 213, 215 can overlap with one another, as shown in FIG. 6, or can be in completely different areas of the total array, as desired.

Figure 7:
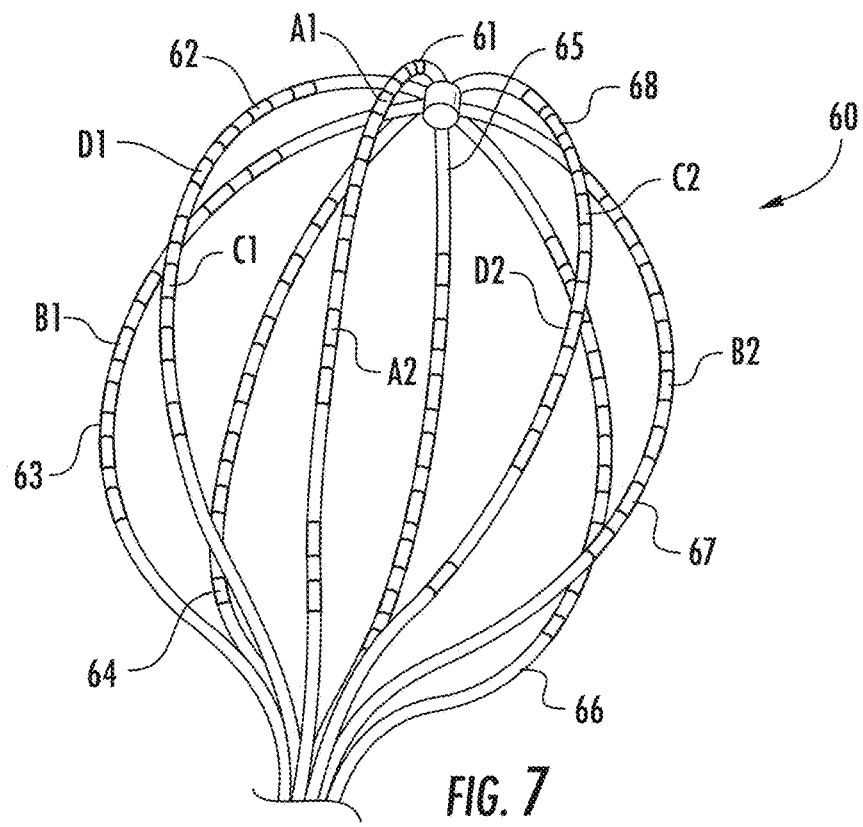
FIG. 7 schematically illustrates one embodiment of a basket-type mapping electrode catheter as described herein.

The electrode array can be of any suitable shape or design. FIG. 7 illustrates a basket-type catheter 60 that can be designed and utilized as described herein. The basket-type catheter 60 includes 8 splines 61, 62, 63, 64, 65, 66, 67, 68, each of which include 8 ring-type electrodes spaced apart along the splines. During use, a plurality of the available electrodes can be utilized that can define the multiple bipolar electrode pairs located around the desired perimeter. For instance, in the illustrated embodiment, the bipolar electrode pair A1, A2 are both located on spline 61. The bipolar electrode pair B1, B2 includes the B1 electrode on spline 63 and the B2 electrode on spline 67. The bipolar electrode pair C1, C2 and the bipolar electrode pair D1, D2 each include one electrode on spline 62 (D1 electrode and C1 electrode) and one electrode on spline 68 (D2 electrode and C2 electrode). Thus, the electrodes selected for utilization in a mapping protocol define a perimeter (A1, D1, B1, C1, A2, D2, B2, C2 around the perimeter) using electrodes on five of the available splines (61, 62, 63, 67, and 68) with the members of each bipolar electrode pair opposed to one another across the perimeter formed by the selected electrodes.

Figure 8:
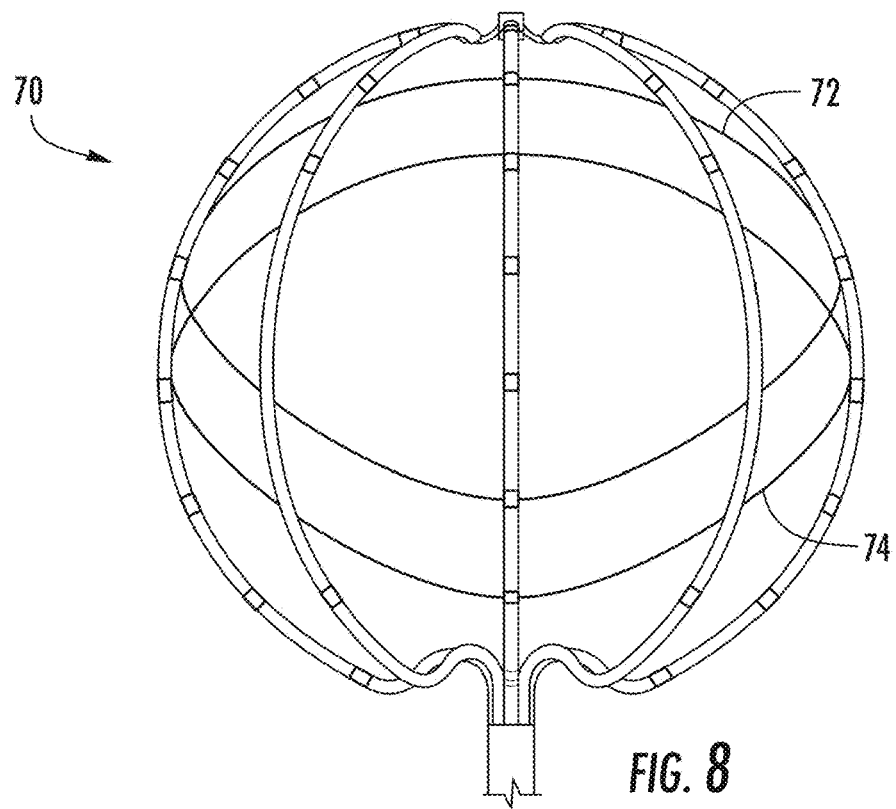
FIG. 8 schematically illustrates a method of use of a basket-type mapping electrode catheter as described herein.

Of course, any of the electrodes of a basket-type catheter can be utilized at one time. In addition, multiple different portions of all of the available electrodes can be utilized sequentially to better examine the cardiac tissue. For instance, FIG. 8 illustrates a basket-type catheter 70 that includes a plurality of splines, similar to the basket-type catheter of FIG. 7. According to one embodiment, a first set of electrodes on the five illustrated splines can together define a perimeter 72, the signals of which can be measured to map all or a portion of a heart chamber. Following this procedure, signals from a second set of all of the available electrodes on the five illustrated splines can together define a perimeter 74, and the signals from these electrodes can be analyzed to map a different portion of the heart chamber. Any combination of the available electrodes can be utilized at any time, provided the selected electrodes analyzed together can define a perimeter, with the members of each bipolar electrode of the set opposed to one another across an area defined by the perimeter. Through selection and measurement/analysis of the signals of defined sets of all of the available electrodes of a larger array, highly detailed information can be obtained with regard to arrhythmia triggers and/or drivers.

In yet another embodiment, the electrodes can be designed for external use, with each of the electrodes of the array attached to predetermined location on a patient's skin. The electrodes can be located on the patient's skin so as to define a perimeter with the electrodes of each bipolar electrode pair opposed to one another across the central area of the perimeter as described above for internal use heart catheters. The external body mapping can similarly provide information with regard to location and/or direction of arrhythmia triggers and/or drivers.

There are specific physiologic characteristics of arrhythmia triggers and drivers for which the disclosed catheters can have marked advantages over previously known types of catheters. By way of example, vector analysis of the signals from bipolar electrode pairs caused by peripheral spiral wave fronts moving away from a rotor core can provide important directional information, as a signal will vary depending upon the alignment of that bipolar electrode pair with the incoming electrical activation wave front. For instance, a bipolar electrode pair that is aligned parallel to the direction of the depolarizing wave front can have a broad electrogram recording of large amplitude. In comparison, a bipolar electrode pair that is aligned perpendicular to the incoming wave front can have a narrow electrogram recording of small amplitude. In such a manner, vector analysis of the signals of the bipolar electrode pairs as described can provide specific directionality of an incoming wave front. Moreover, as the electrode array can include multiple electrode pairs and each pair can provide different data concerning the characteristics of the wave front, the combined data can be more comprehensive as compared to previously known cardiac mapping systems.

During use, a catheter can be located on tissue (e.g., cardiac tissue or skin) such that the selected electrodes of the array are in electrical communication with the tissue. Upon analysis of the electrical signals at that location, if no trigger or driver characteristic recording is seen at that particular site, then a different location can be examined. For instance, and depending upon the particular nature of the catheter, the catheter can be moved to another location or alternatively the signals from a different set of electrodes of the larger array can be examined, so as to examine a different area of tissue. The process can be continued until a characteristic electrogram recording is recognized. Upon recognition of a characteristic recording, for instance an electrogram that designates a rotor core nearby, the area of tissue that is examined can be moved in the direction of the source of the wave front based upon the directional information provided by the vector analysis of the electrogram recording. For instance, the catheter can be moved or the signals of a different set of electrodes can be examined. Once the perimeter defined by the electrodes is positioned such that the core of the rotor is within the perimeter, a very specific diagnostic signal pattern can emerge. Specifically, upon location of a rotor core within the perimeter defined by the bipolar electrodes, a single wave front activation electrogram recording can exhibit alternating slopes of double potentials that can be recorded in all of the bipolar electrode pairs simultaneously (further detailed explanation below).

If a focal ectopic trigger focus is within the perimeter of the bipolar electrodes rather than a rotor core, then a different specific diagnostic electrogram can be recorded. For instance, an ectopic focal trigger site within the perimeter of the bipolar electrodes of a catheter can present electrical wave fronts in a circular centrifugal pattern. In this case, the bipolar electrode pairs around the perimeter can present similar sloping electrograms. Triggers and drivers of arrhythmia identified by use of the bipolar electrode pairs can then be sites targeted for ablation.

Figure 9A:
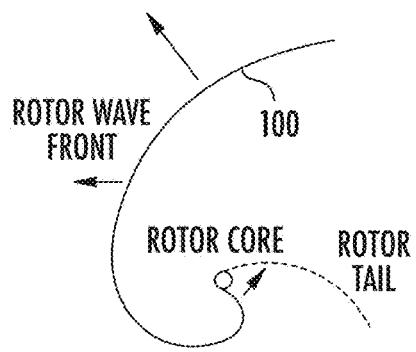
FIG. 9A-FIG. 9D schematically illustrate rotor activity in cardiac tissue and include an image of a propagating electrical wave circling around a rotor core (FIG. 9A), the rotor core outside the boundary of a circular mapping catheter (FIG. 9B), the wave front in the process of passing the circular mapping catheter (FIG. 9C), the wave front having passed the circular mapping catheter and again outside the boundary of the catheter (FIG. 9D)

FIG. 9A schematically illustrates the wave front 100 of a rotor. As shown, the rotor has a convex wave front 100 with a circular trajectory. At the core, the curvature of the wave front is highest, but the wave front cannot penetrate the core during the refractory period of the cells. Thus, the wave front activation pattern has a spiral shape.

Figure 9B:
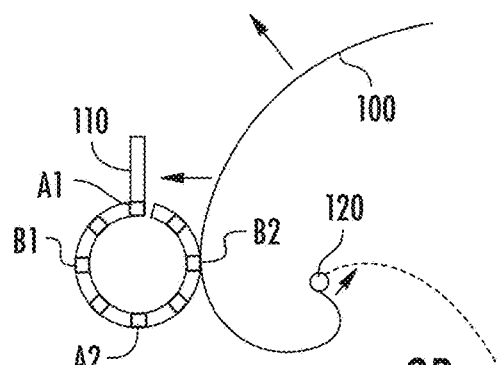
Figure 9C:
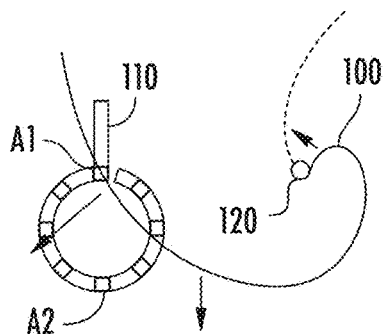
Figure 9D:
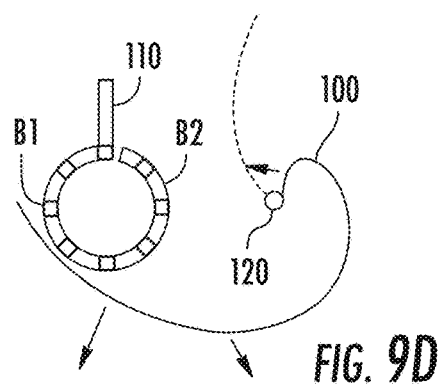

FIG. 9B, FIG. 9C, and FIG. 9D illustrate a circular mapping catheter 110, as described herein, held in various relationships to a rotor wave front 100. At FIG. 9B, the rotor core 120 is outside of the diameter of the circular catheter 110. The diametrically opposed configuration of the bipolar electrode pairs provides immediate information with regard to direction of the wave front 100. For instance, in the illustrated embodiment, the earliest activated pair of the array during a rotation will be the B1, B2 pair. This pair will be essentially parallel with the incoming activation direction and will therefore have the earliest activation and largest electrogram potential amplitude. On the other hand, the A1, A2 electrodes are perpendicular to the wave front and will be the last activated of the bipolar electrode pairs of the catheter via activation of the A1 electrode as shown at FIG. 9C. The activation of the A1, A2 pair will have the narrowest smallest amplitude electrogram of all of the pairs of the catheter 110. As rotation continues, the wave front 100 passes the B1 pole of the B1, B2 pair initially encountered (FIG. 9D).

After the wave front passes, the tissue just activated is refractory from another stimulus for the duration of its refractory period. In a rotor or reentrant circuit, the wave front appears to chase its tail of refractoriness. Limiting the activation of tissue as it circles around results in very steady activation cycle lengths. The tissue near a rotor (e.g., within 1 or 2 centimeters) is driven in a 1:1 fashion with each complete rotation of the rotor, not allowing fibrillatory or more chaotic activity in that specific region. Therefore, a single discreet electrogram can be recorded only with each passing wave front and with each rotation of the rotor.

Figure 10A:
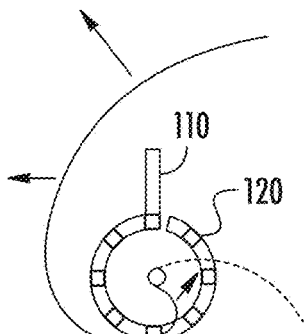
FIG. 10A-FIG. 10C illustrate a circular mapping catheter directly overlying a rotor and include an image as the wave front passes the bottom-most (or south) electrode (FIG. 10A), as the wave front passes the farthest right (or east) electrode (FIG. 10B) and as the wave front passes the top-most (or north) electrode (FIG. 10C)
Figure 10B:
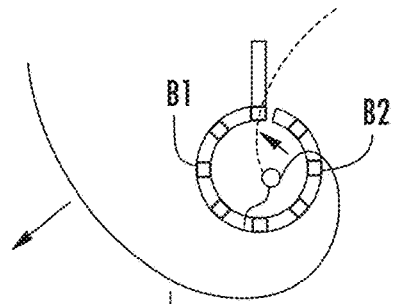
Figure 10C:
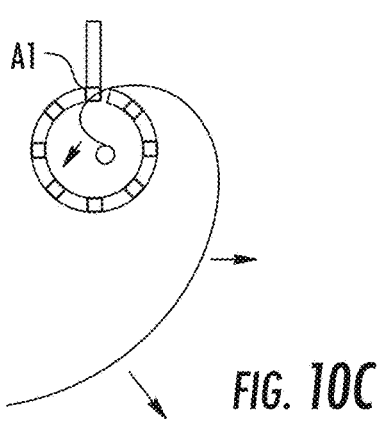
Figure 77:
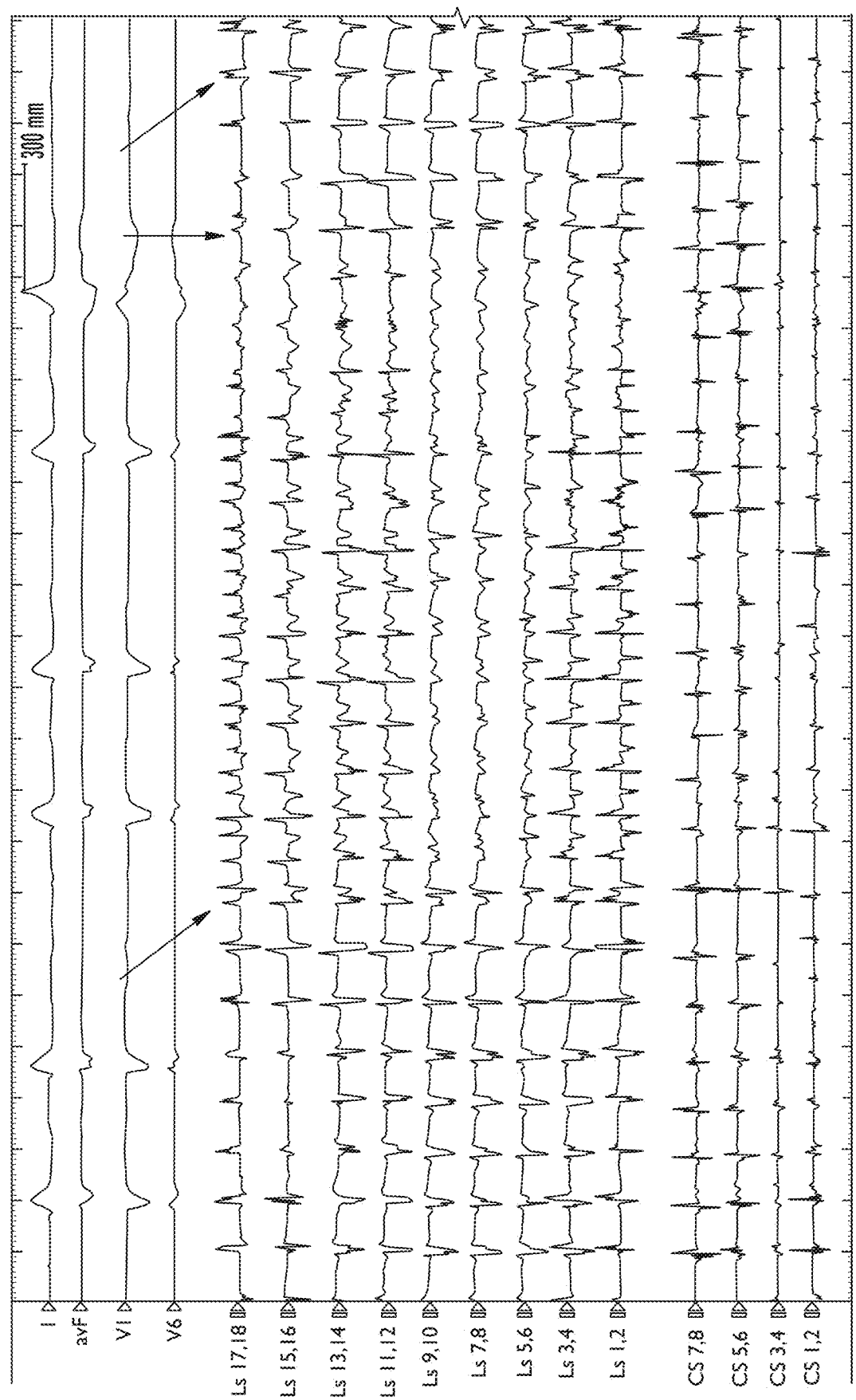

In the example illustrated in FIG. 10A-FIG. 10C, the catheter 110 is directly over a rotor core 120. Bipolar electrode recordings directly over the rotor core 120 can show secondary inverted split potentials on an electrogram. This is explained by the rotor wave front passing under one pole of a bipolar electrode pair while moving in a first direction, which results in a discreet directional slope electrogram signal, and then passing under the opposite pole, which results in an opposite slope electrogram. For instance, as the wave front passes under the A2 electrode as shown in FIG. 10A, the electrogram can exhibit a discreet upward directional slope. As shown in FIG. 10C, after the rotor turns halfway through its rotation it will pass under the A1 electrode, which is the other electrode of the A1, A2 bipolar electrode pair. During this portion of the electrogram recording, the wave front activation underneath the second A1 pole will be moving in the opposite direction as compared to when the wave front passed the A2 electrode. This will result in an inverted slope of the second electrogram potential recording as compared to the first. For instance, if the A1, A2 lead electrogram exhibited a discreet upward directional slope at the FIG. 10A orientation, the A1, A2 lead electrogram will exhibit a discreet downward directional slope at the FIG. 10C orientation. Significantly, the same inverted split potential electrogram will be recorded for all of the bipolar electrode pairs when the rotor core is within perimeter defined by the electrodes. For instance, a similar pattern will be exhibited as the wave front passes under the B1, B2 pair, the B2 pole passage being illustrated in FIG. 10B. With each single rotation of a rotor underneath a bipolar electrode pair, two distinct but opposite sloping waveforms can be recorded.

Identifying the presence of a rotor by specific rotor core characteristics with 2- to 4-millimeter electrode spacing along a linear catheter or a spline as has been previously attempted is difficult at best. Using activation wave fronts simultaneously over the entire left atrium can provide overall results but requires computational off-line assessment. Through expansion of the distance between recording bipoles and addition of more bipoles to define a perimeter in the disclosed catheters, a much larger tissue area can be examined at one time to assess for rotor activity.

In addition to the ability to map and identify triggers and drivers of atrial fibrillation, a catheter as disclosed herein can track a rotor as it precesses across cardiac tissue. FIG. 11 illustrates electrogram recordings of surface leads including diametrically opposed bipolar electrode pairs and illustrates the characteristics of a precessing rotor moving from outside the recording circle to within the circular pattern of the electrode pairs. The top 4 recordings of FIG. 11 are from electrocardiogram surface leads I, avF, V1, and V6. The next 9 recordings are from electrode pairs diametrically opposed from each other in a circular pattern. At the left-most arrow above these 9 recordings, all of these 9 tracings show a sudden transition to alternating slopes of double potential as the rotor core precesses into the circular pattern. This continues for 15 rotations. The vertical arrow marks when the rotor core precesses out of the boundary of the circular pattern and the single potential slopes resume. At the right-most arrow on FIG. 11, the rotor core has reentered the circle of diametrically opposed electrodes. The final 4 recordings at the bottom of FIG. 11 are from electrodes along a catheter located in the coronary sinus vein.

Figure 12:
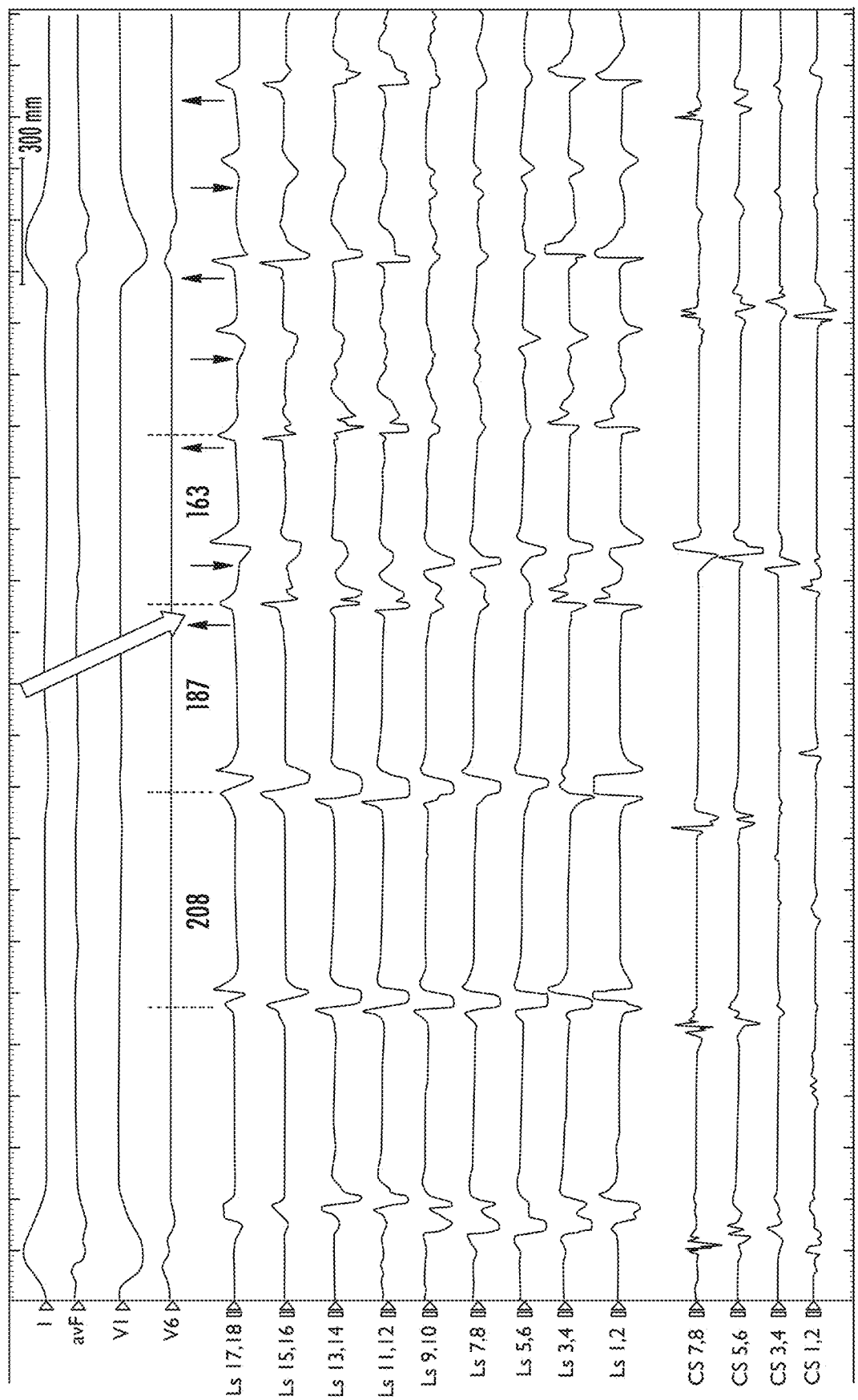
FIG. 12 illustrates recordings from electrocardiogram surface leads including recordings from diametrically opposed bipolar electrode pairs as described herein.

FIG. 12 presents another set of electrogram recordings including the top 4 from surface leads I, avF, V1, and V6; the next 9 from electrode pairs diametrically opposed from each other in a circular pattern, and the bottom 4 from electrodes along a catheter located in the coronary sinus vein. FIG. 12 illustrates how the cycle length recorded by the electrogram can be altered due to the Doppler Effect as the rotor core precesses across the cardiac tissue. As illustrated in FIG. 12, as the distance between the rotor and the bipolar electrode circle decreases, there is a decrease in cycle length. As the rotor core moves within the boundaries of the circular pattern (marked by the arrow) there is a sudden doubling of electrical potentials that alternate in slope. This is seen in all nine of the directional recordings. The rotor stays within the circular pattern for 15 rotations and then precesses back out.

The pattern repeats as the rotor core precesses back and forth, in and out of the perimeter of the catheter electrodes. When the rotor is outside the circular boundary of the electrodes, the cycle length is 202 milliseconds or greater. Cycle lengths between upsloping potentials decreases to an average of 173 milliseconds when the rotor is inside the circular pattern. When the rotor migrates back out of the electrode array, the cycle length again increases (not shown on FIG. 12).

Significantly, the cycle frequency can be seen to vary by a factor of 2 (or more due to the Doppler Effect) as the rotor core precesses in and out of the perimeter defined by the bipolar electrodes. As shown in FIG. 12, when the rotor core is within the perimeter defined by the bipolar electrodes, the cycle frequency can be double or more, e.g., between 2 and 3 times, that of the cycle frequency when the rotor core is outside of the perimeter. Moreover, this effect is seen in all of the bipolar electrode signals. Thus, analysis of the signals of bipolar electrodes arranged as described can be used to quickly and definitively identify the location and direction of a rotor core, as well as other features of arrhythmia.

In one embodiment, unipolar analysis of the activation signals from the electrodes defining the area perimeter can be carried out to provide information about a source of a depolarization wave front. For instance, in one embodiment, the electrode activations can be analyzed sequentially around the perimeter to provide additional information. In one embodiment, a unipolar signal analysis can be carried out following a bipolar electrode analysis as discussed above so as to provide additional information about a depolarization source. This is not a requirement of an analysis methodology, however, and in some embodiments, a unipolar signal analysis can be carried out independent of a bipolar electrode analysis.

A unipolar analysis of the electrode activation signals can be used to confirm location of a depolarization source within a predetermined area and/or to more specifically identify the location of a depolarization source (e.g., a rotor core) within the area defined by the electrodes. For instance, analysis of the bipolar electrode pair signals can initially be utilized to map from which direction a rotor approaches an area (e.g., a recording area as defined by the catheter electrodes), as well as the time and position at which the rotor crosses the perimeter into the area defined by electrodes A unipolar analysis of the electrode signals can then be carried out to locate the rotor core with higher precision. Following this analysis, the tissue at the rotor core and the paths of abnormal tissue that allow the rotor to be sustained can be treated, e.g., ablated, to decrease arrhythmic episodes. The precision mapping provided by the two-pronged analysis can prevent excessive tissue ablation and effectively treat a depolarization source with minimum tissue disruption.

Figure 13:
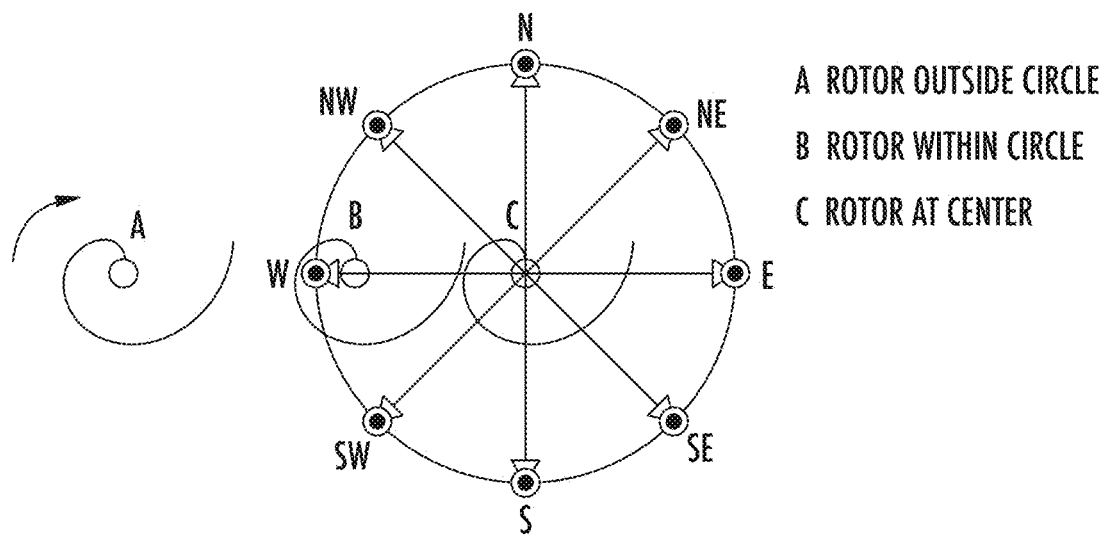
FIG. 13 illustrates three potential locations of a rotor core within a perimeter defined by a series of electrodes.

FIG. 13 schematically illustrates different possible positions of a rotor core in relation to a catheter. At position A, the rotor core is outside of the perimeter defined by the electrodes (in this particular case a circle). At position B, the rotor core is within the perimeter, and at position C, the rotor core is at the center of the circle defined by the electrodes. As the depolarizing wave front sweeps around the core as indicated by the directional arrow at rotor core position A in FIG. 13, the electrodes of the catheter will be activated in a recognizable pattern, with the pattern depending upon the relative location of the rotor core with regard to each of the electrodes of the catheter.

When a rotor core is outside of the area defined by a circular catheter, e.g., at position A of FIG. 13, the electrodes will be activated in a pattern that may not proceed sequentially around the circle. For instance, the W electrode may be activated first and followed in sequence by the NE electrode and then the E electrode, depending on the exact relationship between the rotor core and the catheter. In contrast, when the rotor core is within the perimeter, as at positions B or C of FIG. 13, the electrodes will be sequentially activated by the depolarizing wave front as is sweeps around the core. Thus, a relatively simple analysis of the order of activation of the electrodes around the perimeter of the catheter can provide information with regard to the location of the depolarization source.

Temporal unipolar electrode analysis of the activations can provide additional information with regard to the location of the depolarization source. For instance, analysis of the time gap between activation of adjacent electrodes around the perimeter can be utilized to identify the location of the rotor core as not only within or exterior to the area defined by the electrodes of the catheter, but can also provide a more precise location of the source within the area.

When a rotor core is within the area defined by the catheter perimeter, the precise location of the rotor core within the area can be determined from the time between activation of adjacent electrodes around the perimeter and the cycle length (i.e., revolution frequency) of the rotor. The cycle length of a depolarization wave front can be obtained through analysis of the repeating electrode activations at one or more of the catheter electrodes over a period of time. As discussed above, as a rotor precesses across the cardiac tissue, the cycle length at individual electrodes (either bipolar or unipolar electrodes) can exhibit a Doppler effect. However, this effect will present itself as a readily apparent variation in cycle length as the rotor precesses. Accordingly, when the cycle length as determined at a single electrode does not vary excessively over several cycles (e.g., about 10 or more cycles, for instance from about 10 to about 15 cycles), it can be assumed with high confidence that this time period corresponds closely to the cycle length of the rotor. This cycle length can be confirmed through comparison of the cycle length obtained at several different electrodes, and in one embodiment through comparison of the cycle length obtained at electrodes on opposite sides of the perimeter. When the cycle length at each catheter is stable and in correspondence with one another, this value can be assumed to be the rotor cycle length.

Figure 14:
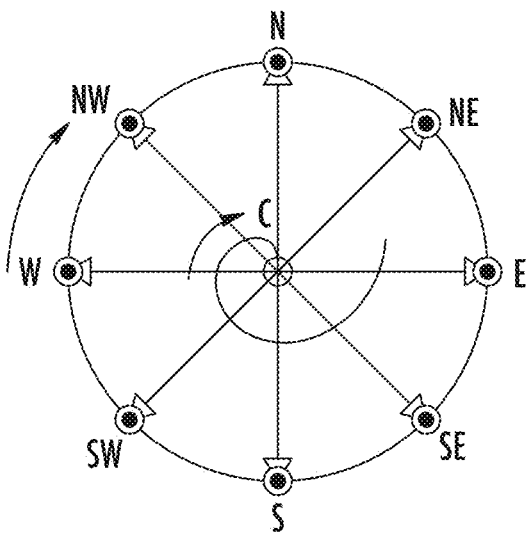
FIG. 14 illustrates a catheter and a rotor core in the center of an area defined by electrodes at the perimeter of the catheter.

FIG. 14 illustrates the special case of a rotor core located the center C of a catheter area. In this situation, the depolarizing wave front of the rotor will activate each electrode successively around the perimeter. Assuming isotropic conditions exist, and the electrodes are spaced equally around the perimeter, the time period between activations of each successive electrode will be equal to one another. For example, in the illustrated embodiment of FIG. 14, in which there are 8 electrodes equally spaced around a circular catheter area, the time gap ($t_g$) between sequential electrodes will be the rotor cycle length ($CL_{Rt}$) divided by the number of electrodes (n), or in this case, 8. If, upon analysis of the unipolar electrode activations, the time gaps are substantially equal to one another and to $CL_{Rt}/n$, then the rotor core is located at the center of the area defined by the electrodes.

Adjustments to an analysis for recognition of a rotor core under a central or other particular point of a catheter area can be carried out on a case by case basis, but are well within the capabilities of one of ordinary skill in the art. For instance, adjustments depending upon the shape of the perimeter, a differential spacing between adjacent electrodes, the particular point of the area under analysis, etc. can be carried out through geometric modeling.

Figure 15:
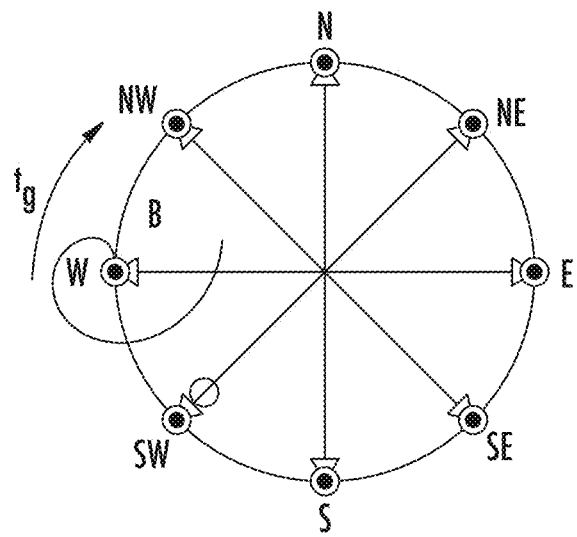
FIG. 15 illustrates a catheter and a rotor core at the periphery of an area defined by electrodes at the perimeter of the catheter.

A more general analysis can also be carried out to determine a more precise location of a rotor core within a catheter area. For instance, as illustrated in FIG. 15, a rotor core can be located on the perimeter of a catheter area and still be recognized via a bipolar analysis to be within the general catheter area. However, in this case, the rotor core can also be relatively far from the center, and ablation of the central area under the catheter may leave the rotor core area untreated.

If one assumes that a rotor spins with its lateral rotation in the same plane as the tissue surface, a general solution for determination of rotor core location within a catheter area can be determined by initial determination of the maximum possible time gap ($t_{gmax}$) between activation of adjacent electrodes, which in turn depends upon the number of electrodes located around the perimeter and the rotor cycle length $CL_{Rt}$. When a rotor is within the catheter area, the time gap between activation of adjacent electrodes around the perimeter will occur within certain time constraints. In particular, and with reference to FIG. 15, as the rotor makes one complete revolution within the area defined by the catheter perimeter, the electrodes closest to the rotor core will exhibit the longest gap time between activations (i.e., the tangential velocity of the wave front is lower closer to the rotor core). Accordingly, the maximum gap time possible for activation between adjacent electrodes will be in those instances in which the rotor core is on the perimeter and under one of the electrodes as illustrated at FIG. 15. Geometric analysis of this situation can provide a general solution for this maximum gap time in terms of the number of electrodes located around the periphery of the catheter and the cycle length of the rotor, e.g., in the case of a circular catheter:

$$t_{gmax}=CL_{Rt}(0.25+1/(2n))$$

in which $t_{gmax}$, $CL_{Rt}$ and n are as defined above.

The value obtained for $t_{gmax}$ can be utilized to confirm that the rotor core is within the catheter area. In particular, if the time gap observed between any two adjacent electrode activations is longer than the maximum time gap for the given catheter and cycle length, then the activation must be coming from a source outside of the catheter area, and the rotor core is not within the area. Conversely, if the longest observed time gap is equal to or less than the maximum possible time gap, then the rotor core is within the area that is defined by the electrodes.

Once the maximum possible time gap for a particular catheter and cycle length is determined, analysis of the actual observed time gaps between the adjacent electrodes sequentially around the perimeter of the catheter can be used to triangulate the location of the rotor core within the catheter area. For instance, the largest observed time gap between two sequential electrodes can inform the observer that the rotor is located in an angle of the tissue area defined by these two electrodes and the center of recording area. Moreover, the closer this largest observed time gap is to the maximum possible time gap as discussed above, the closer the rotor core will be to the perimeter of the catheter area.

Figure 16:
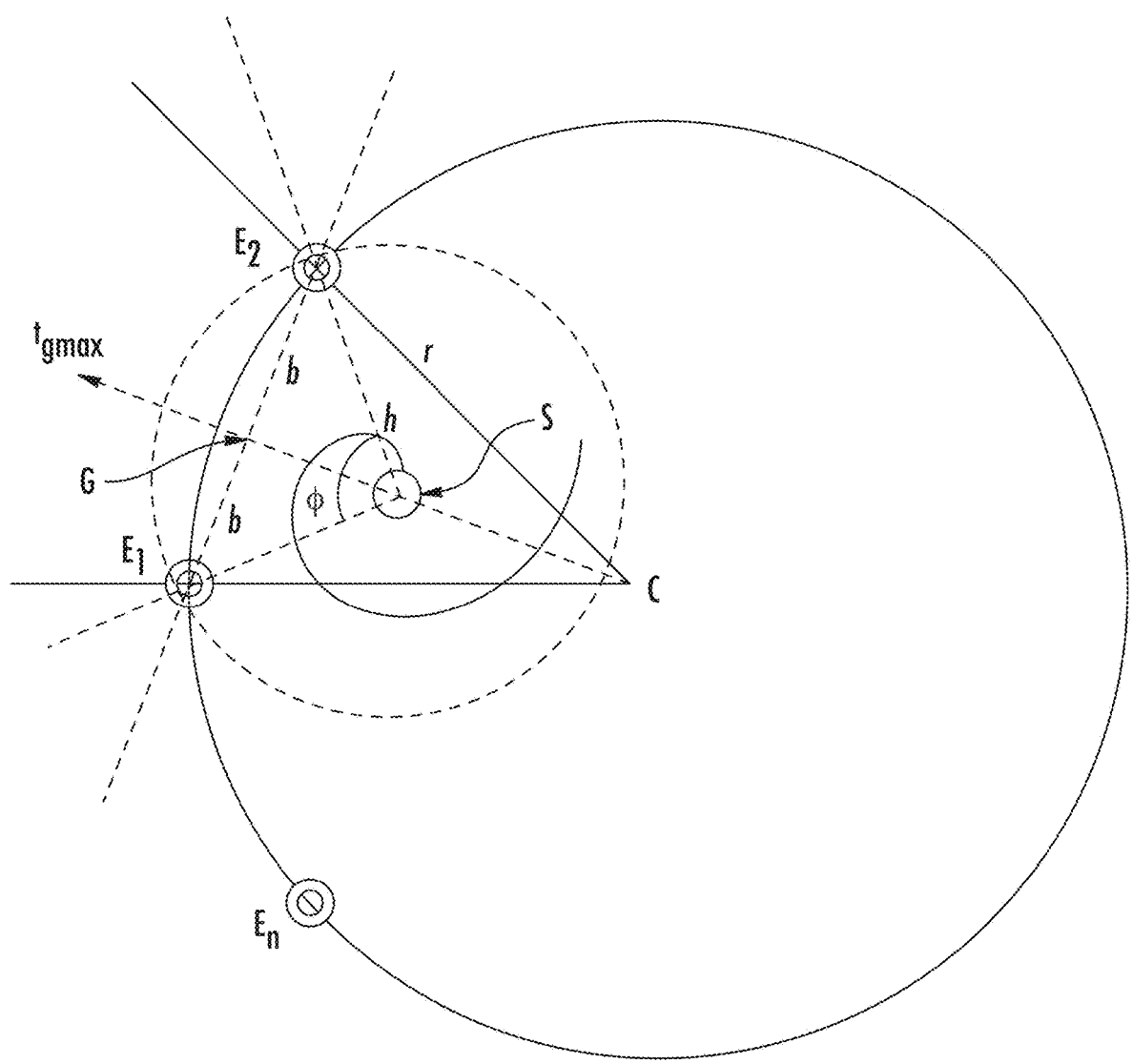
FIG. 16 illustrates one embodiment of a rotor core location within a defined perimeter and a triangulation method for determining the specific location of the rotor core by use of unipolar analysis.

FIG. 16 illustrates an example in which the rotor core (at position S) is on a radius (G) that bisects an angle formed between two electrodes located ($E_1$, $E_2$) within the area of the perimeter of a circular catheter and the center (C) of the circle (i.e., the angle $E_1$, C, $E_2$ on FIG. 16). The radius length (r) of the circular catheter perimeter can be known by the catheter specifications. The maximum observed time gap would be determined as being between electrodes $E_1$ and $E_2$ upon examination of the electrode signals. The rotor core could therefore be determined to be within that angle of the circle and the rotor core can be estimated to be along or near the C-G radius. A circle (dotted circle) formed with the rotor core S at the center will have a radius h, as shown. Assuming constant rotational speed around this circle having the rotor core at the center of the circle S, $t_{omax}$ (the observed time gap between the signal at $E_1$ and $E_2$) can be considered a portion of this circle. The angle $\phi$ is the angle formed as the wave front passes from $E_1$ to $E_2$ as described by the circle with radius h. The distance from the center of the catheter area C to the rotor core S along the radius CG will then be:

$$r(\cos(180°/n))-b\cot(\Phi/2)$$

in which
r is the radius of the circle
n is the number of electrodes on the perimeter
b is ½ of the length of the chord ($E_1E_2$) between the two electrodes (the largest observed time gap being between these two electrodes) and
$\Phi=(t_{omax}/CL_{Rt})360°$.

Figure 17:
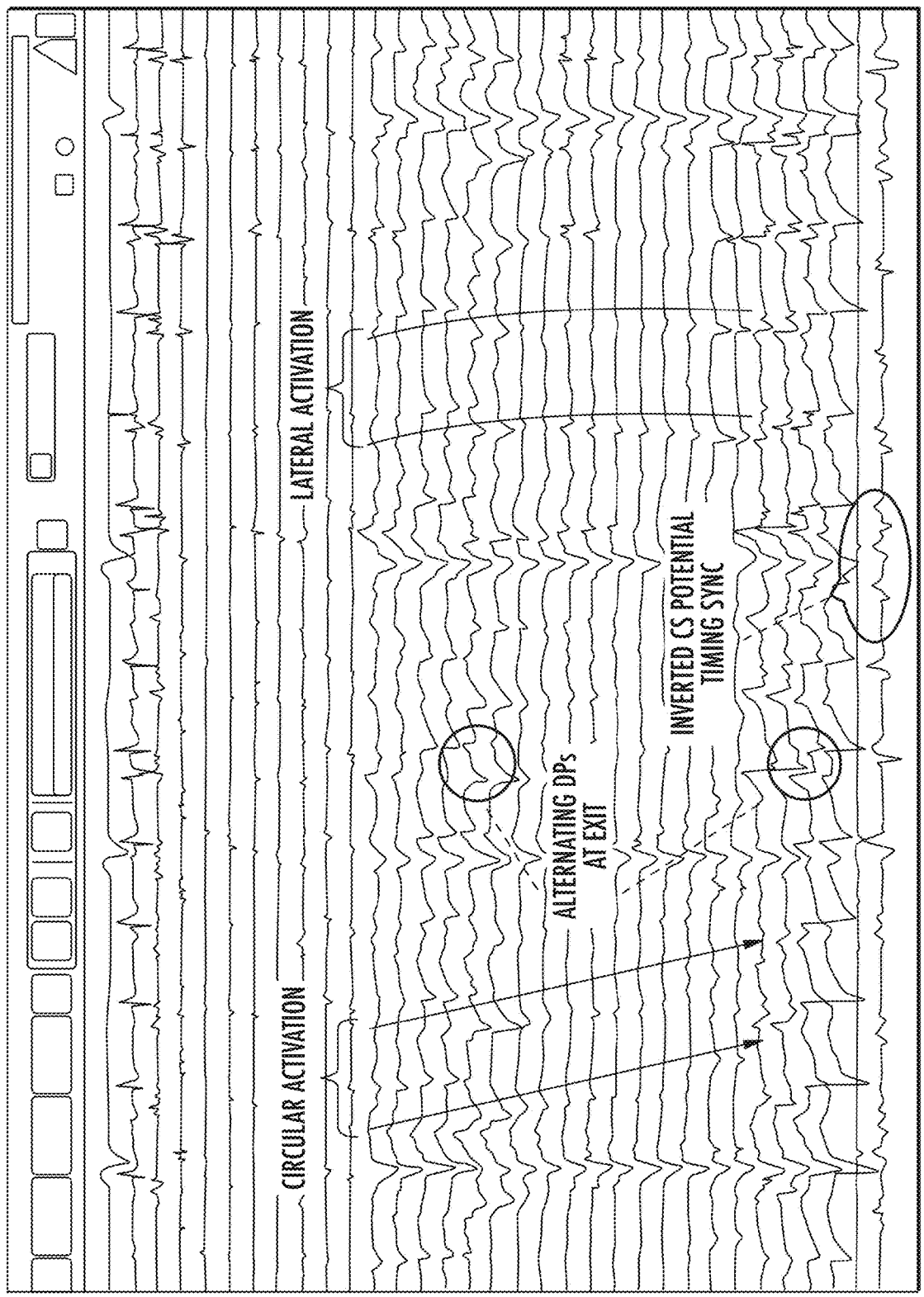
FIG. 17 illustrates recordings from electrocardiogram surface leads demonstrating unipolar electrode analysis of a rotor within the area defined by the cathode and precession out of the area.

FIG. 17 presents a set of electrogram recordings obtained from a circular catheter (similar to that illustrated in FIG. 1) that was overlying rotor activity during atrial fibrillation. This FIG. includes simultaneous recordings of a surface ECG, circular catheter and a coronary sinus vein catheter. The top recording in this FIG. 17 is a surface ECG recording of a patient in atrial fibrillation. The next 10 tracings are bipolar recordings of the closely paired electrograms. The next 20 tracings are the unipolar recordings of each specific electrode. The bottom 2 tracings are recordings from electrodes on a catheter that is placed in the coronary sinus vein. The left half of the FIG. shows rotor activity within the perimeter of the circle of electrodes 1-20. There is a cyclic pattern of sequential unipolar activation around the catheter electrodes (2 slanted arrows). The right half of FIG. 17 illustrates the rotor precessing out of the perimeter of the catheter. At the point of exit across the perimeter, the unipolar activation sequence can be seen to change to more simultaneous (2 vertical arrows).

Figure 18:
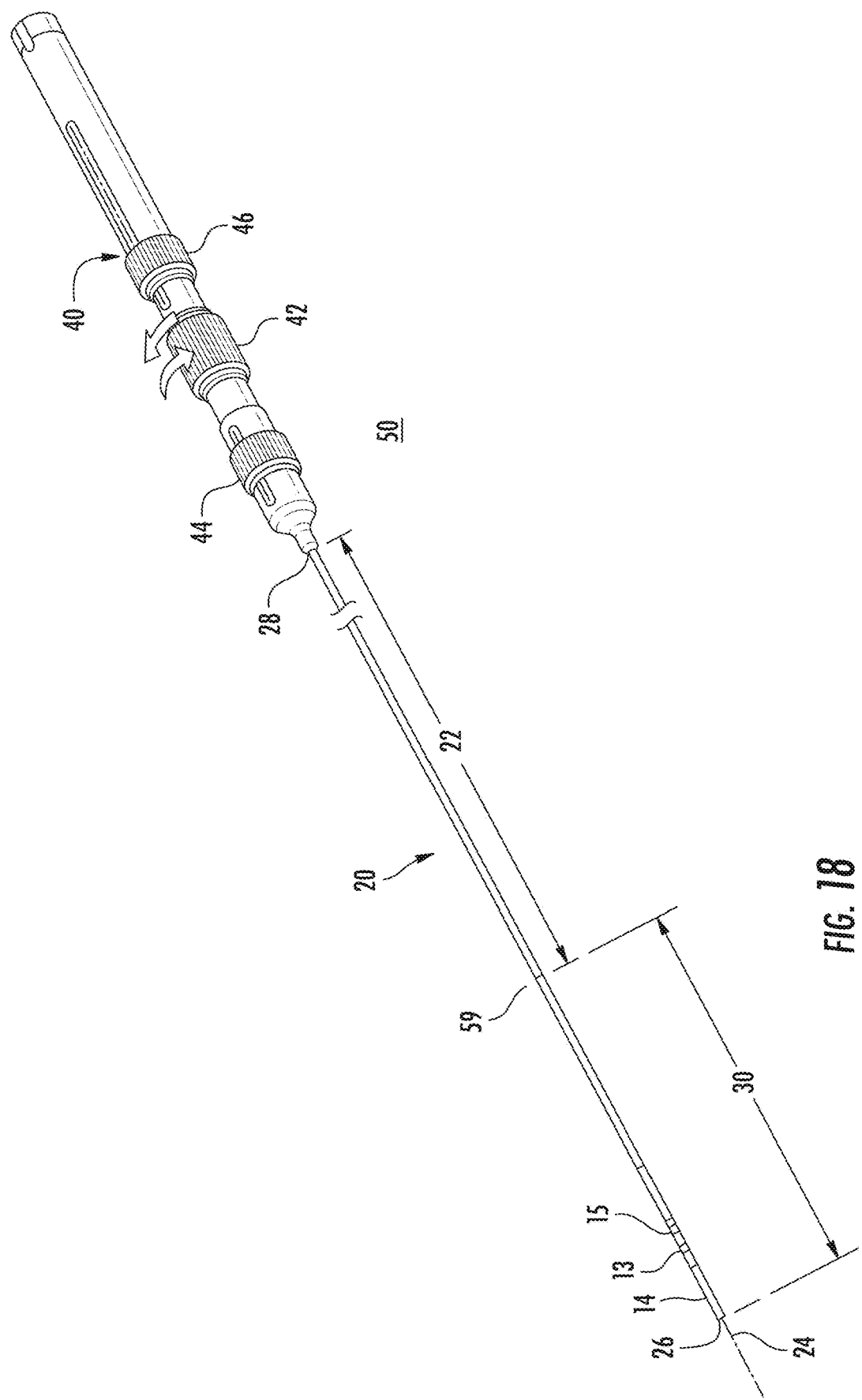
FIG. 18 illustrates one embodiment of a heart catheterization device incorporating a circular mapping catheter as disclosed herein.

An electrode array can be utilized with catheter components as are known in the art. For example, FIG. 18 schematically illustrates an anatomically conforming, flexible catheter 50 incorporating an array of electrodes 13, 14, 15 that can be located with respect to the heart wall for mapping and in one embodiment also for ablation. The distal segment 30 is simplified in FIG. 18 to show three of the electrodes 13, 14, 15, but it should be understood that the distal segment 30 will comprise the array of at least 8 electrodes on the flexible segment that, during use, will curve to define a pattern of bipolar electrode pairs. The catheter 50 can include a porous tip and catheter lumen for emitting irrigating fluid around the electrode array as is known, but those features are not illustrated in FIG. 18 to simplify illustration. It will be understood that the catheter 50 can also function as an ablation catheter and include necessary components for delivery of ablation energy, including without limitation, visible light, infrared energy, and/or electrical energy from or along the distal tip.

The catheter 50 can include a catheter shaft or body 20 and a handle 40. The catheter shaft or body 20 can have a shaft axis 24 that extends between a distal end 26 and a proximal end 28 and can be separated at a demarcation line 59 into a proximal section 22 and a distal section 30. Catheter body 20 may be of any suitable diameter and length and may be straight or pre-curved along its length, but, in one embodiment, is straight when unrestrained. The distal section 30 or the distal segment thereof can be tapered from the diameter of the proximal section 22.

The proximal section 22 can have sufficient column strength and can be capable of good torque transmission to permit controlled placement of the distal section 30 at a target site in the heart. The distal section 30 can be deflectable away from shaft axis 24 so as to form the desired pattern during use. Each electrode 13, 14, 15 is separately connected to insulated conductors extending proximally through the catheter body 20 to terminals of a cable connector in or on the handle 40 that is connected via a cable to the mapping signal amplifiers and optionally also to an ablation energy source. A thermocouple can also be included in the distal segment 30 and separately insulated thermocouple conductors can extend proximally through the catheter body 20 to terminals of the cable connector in or on the handle 40 that are coupled to a temperature display and optionally an ablation energy control apparatus known in the art.

The handle 40 can take any of the forms known in the art for making electrical connections with the conductors within the catheter body 20 and for delivering irrigation fluid to an irrigation lumen (if present) of the catheter body 20. The handle 40 also includes a mechanism for deflecting the distal tip section 30 into a circular pattern(s) and moving the catheter within the body. The mechanism can take any form for pulling, pushing and/or twisting the deflection or push/pull wires within the catheter body 20. In the illustrated embodiment, the handle 40 is attached to the catheter body proximal end 28 and supports axially slidable manipulators comprising push-pull rings 44 and 46 and a rotatable lateral deflection ring 42 that are coupled to the proximal ends of a curve deflection push-pull wire, a knuckle deflection push-pull wire, and a lateral deflection wire. For instance, the lateral deflection ring 42 can be rotated to impart a torque in a lateral deflection wire coupled thereto to laterally rotate the distal section 30 with respect to axis 24 within the proximal section 22.

As shown in FIG. 18, when the push-pull wires are relaxed, the distal segment 30 is aligned with the shaft axis 24 which can be referenced as 0°. The knuckle deflection push-pull wire can be retracted or pulled by sliding ring 46 proximally to impart a radius bend from substantially 0° to form a circular pattern of bipolar electrode pairs of the desired diameter. The knuckle deflection push-pull wire can be extended or pushed by sliding push-pull ring 46 distally to impart a bend that is in a bend direction opposite to the bend direction imparted when the knuckle deflection push-pull wire is retracted or pulled by sliding ring 46 proximally.

The manipulator push-pull ring 44 can be moved proximally or distally to move the curve deflection push-pull wire coupled thereto proximally or distally to further affect the orientation or size of the circular pattern.

For example, pushing the push-pull ring 44 forward toward the distal tip 24 of the catheter can deflect the catheter downward in the southern direction of a circular pattern (as shown for example in FIG. 2). During use in a body, for instance when the catheter is placed against the posterior atrium wall, this movement can be translated to a more inferior position within the heart chamber. Pulling the push-pull ring 44 back can deflect the distal segment 30 in a more northern direction. When the catheter distal segment 30 is placed against the posterior wall, then a counterclockwise rotation of the catheter stem via the lateral deflection ring 42 can slide the circular mapping electrode laterally, towards the east, while a clockwise rotation moves the catheter towards the west.

Figure 19B:
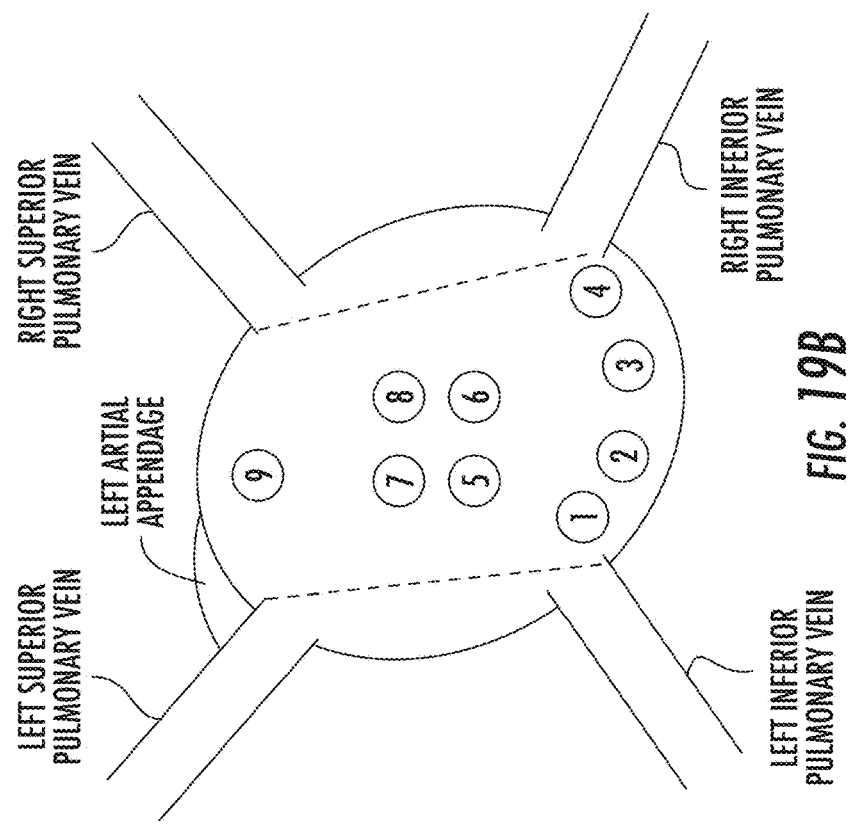
FIG. 19A and FIG. 19B schematically illustrate an atrium mapping positioning method as disclosed herein including an anterior view (FIG. 19A) and a posterior view (FIG. 19B)
Figure 19A:
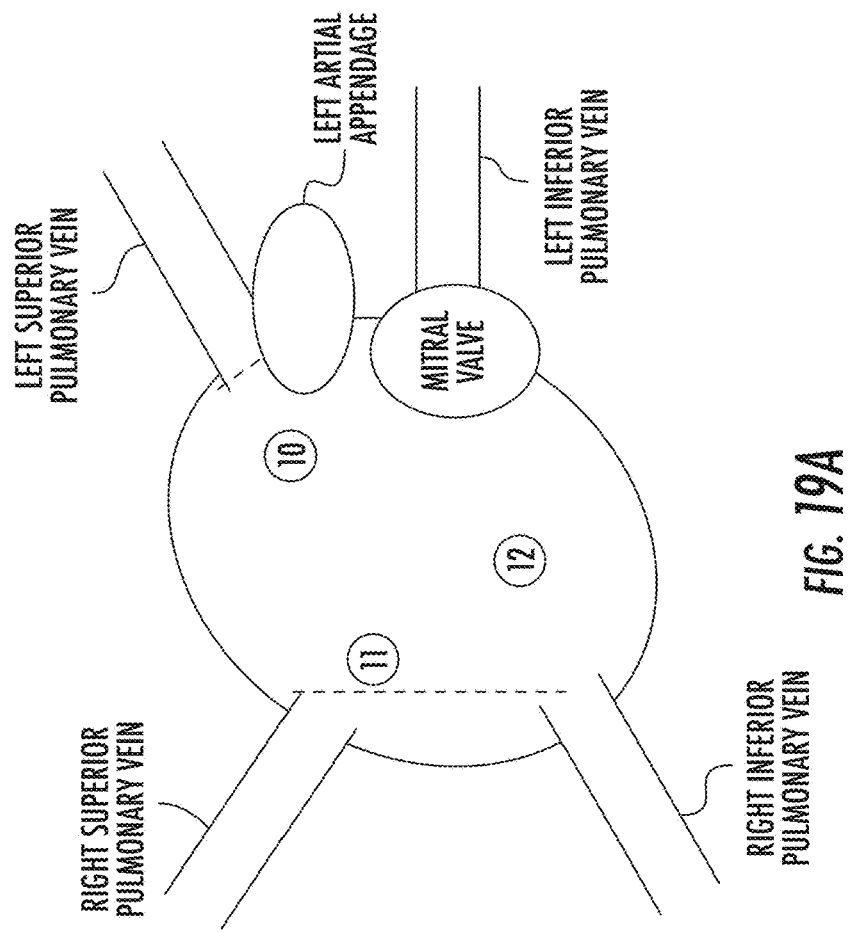
Figure 20:
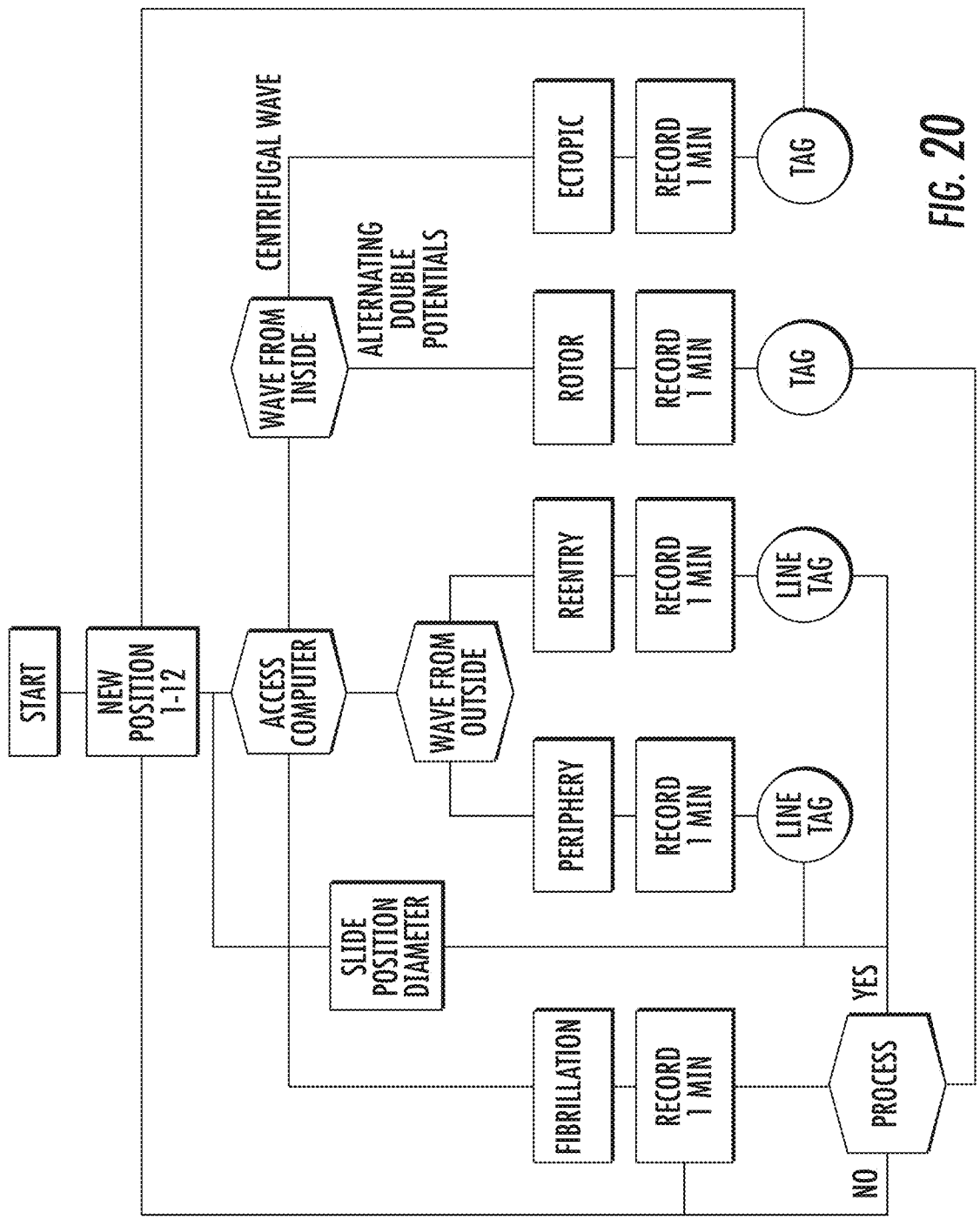
FIG. 20 presents a flow diagram for an atrium mapping positioning method as disclosed herein.
Figure 21:
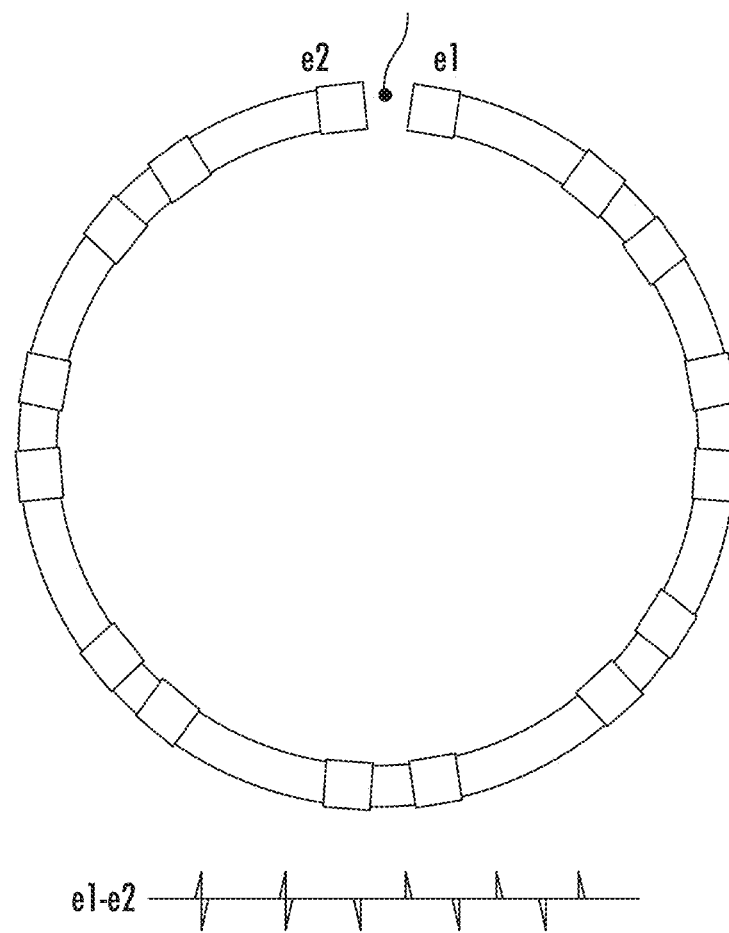
Figure 22:
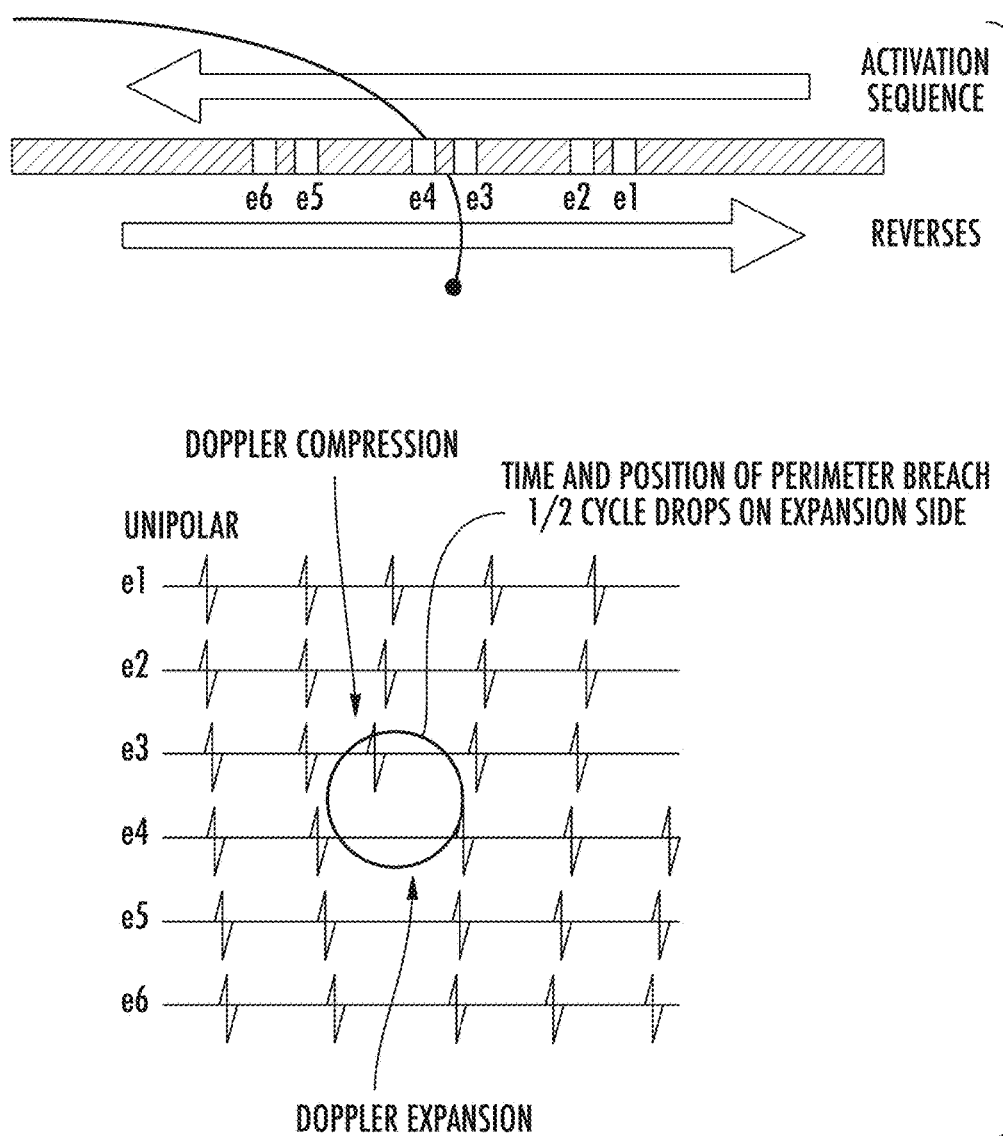
FIG. 22 presents a trace for a rotor precession through a straight line of electrodes and the ½ cycle drop off at the perimeter breach as the rotor passes the line per the schematic illustration.
Figure 23:
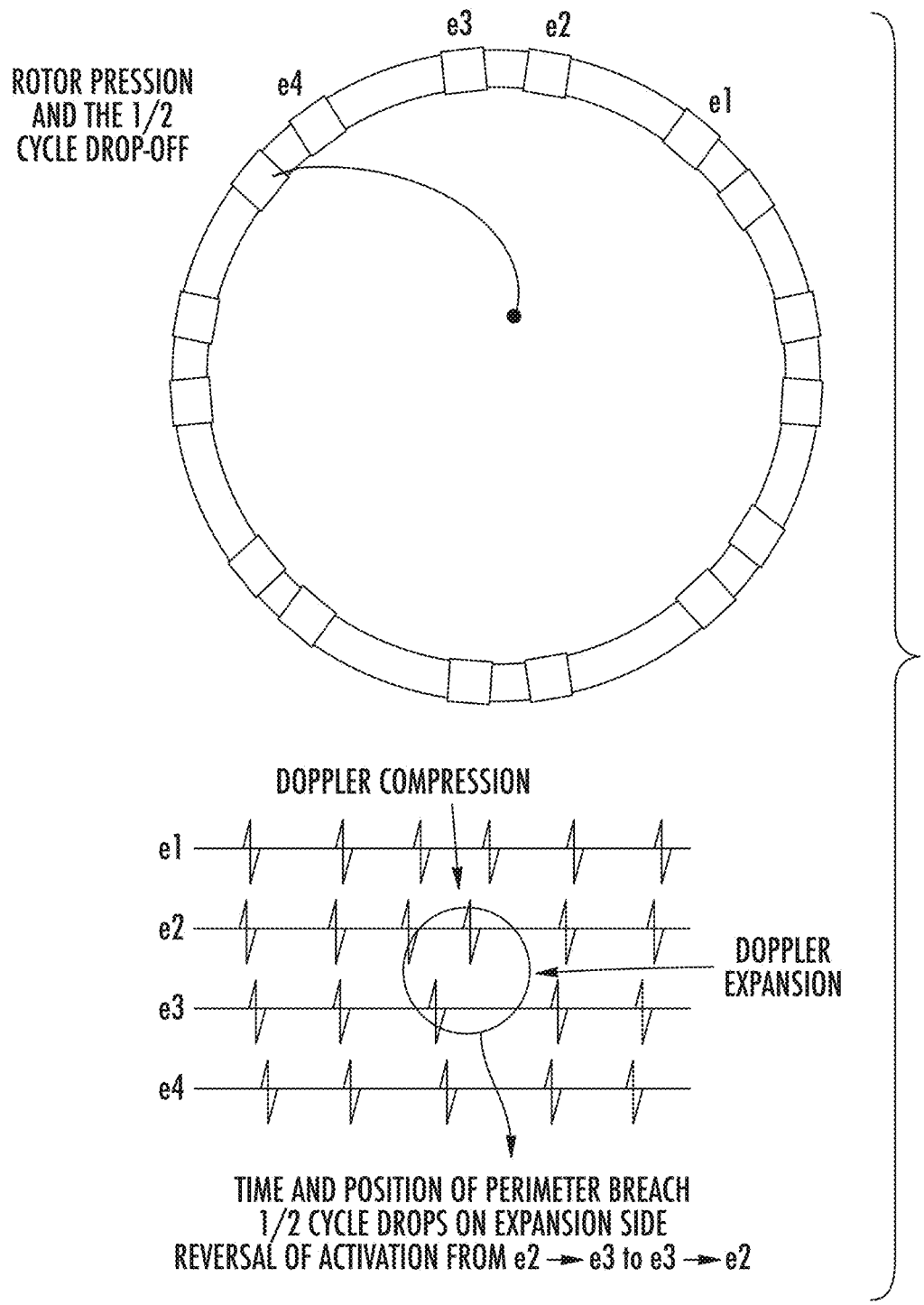
FIG. 23 presents a trace for a rotor precession through a circular presentation of electrodes and the ½ cycle drop off at the perimeter breach as the rotor passes across the circle perimeter.
Figure 24:
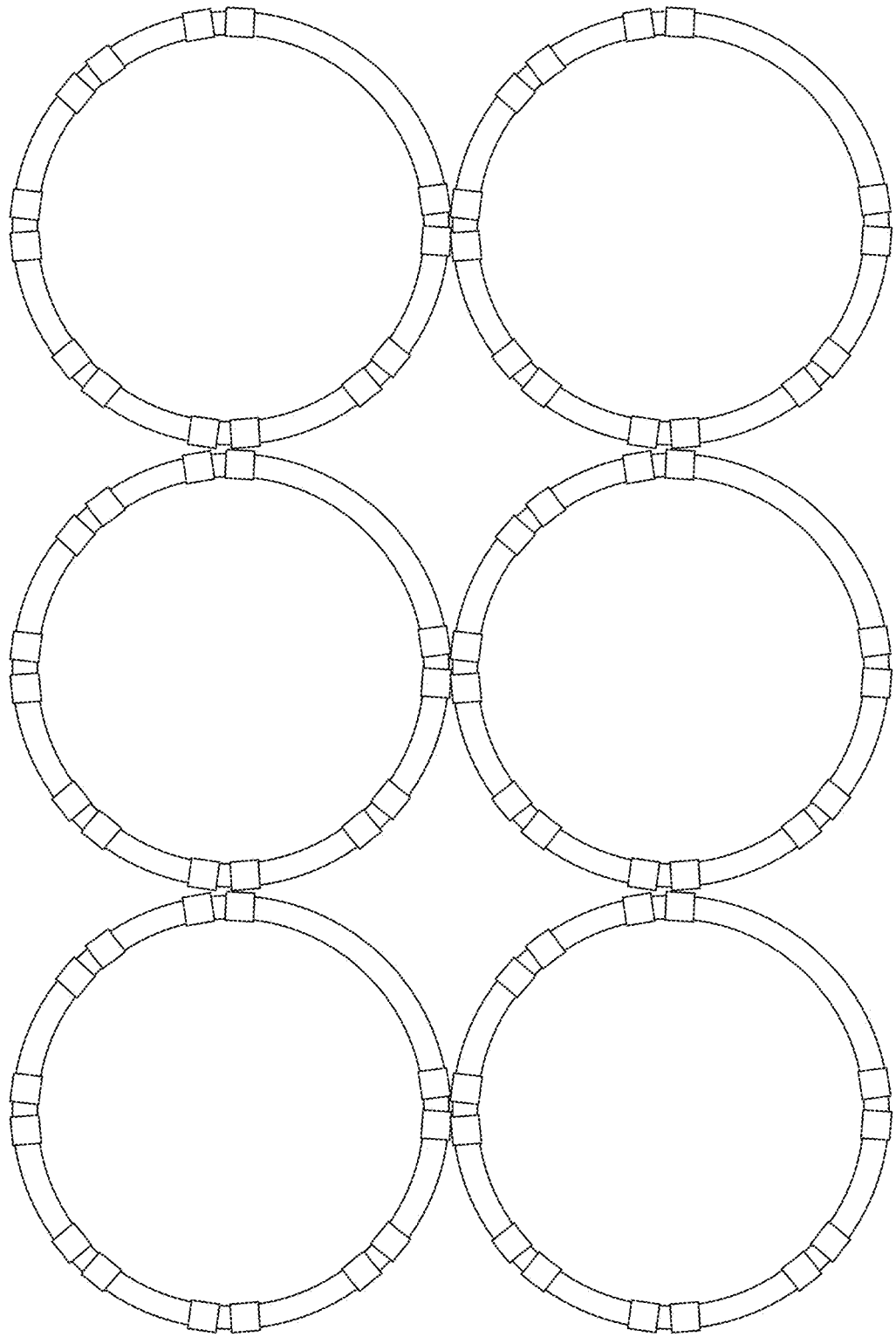
FIG. 24 illustrates one exemplary embodiment of a configuration of a plurality of juxtaposed catheters.
Figure 25:
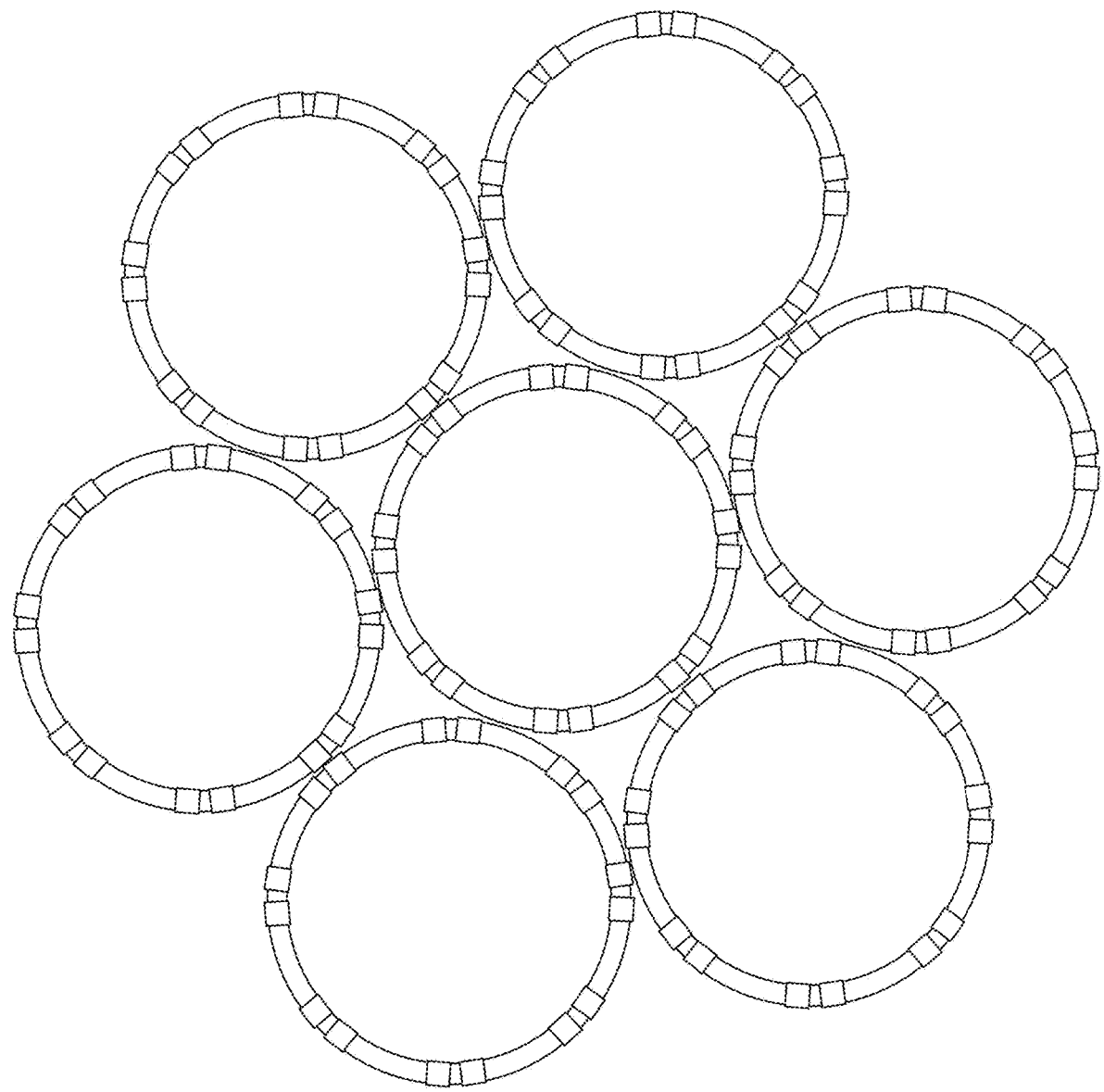
FIG. 25 illustrates another exemplary embodiment of a configuration of a plurality of juxtaposed catheters.
Figure 26:
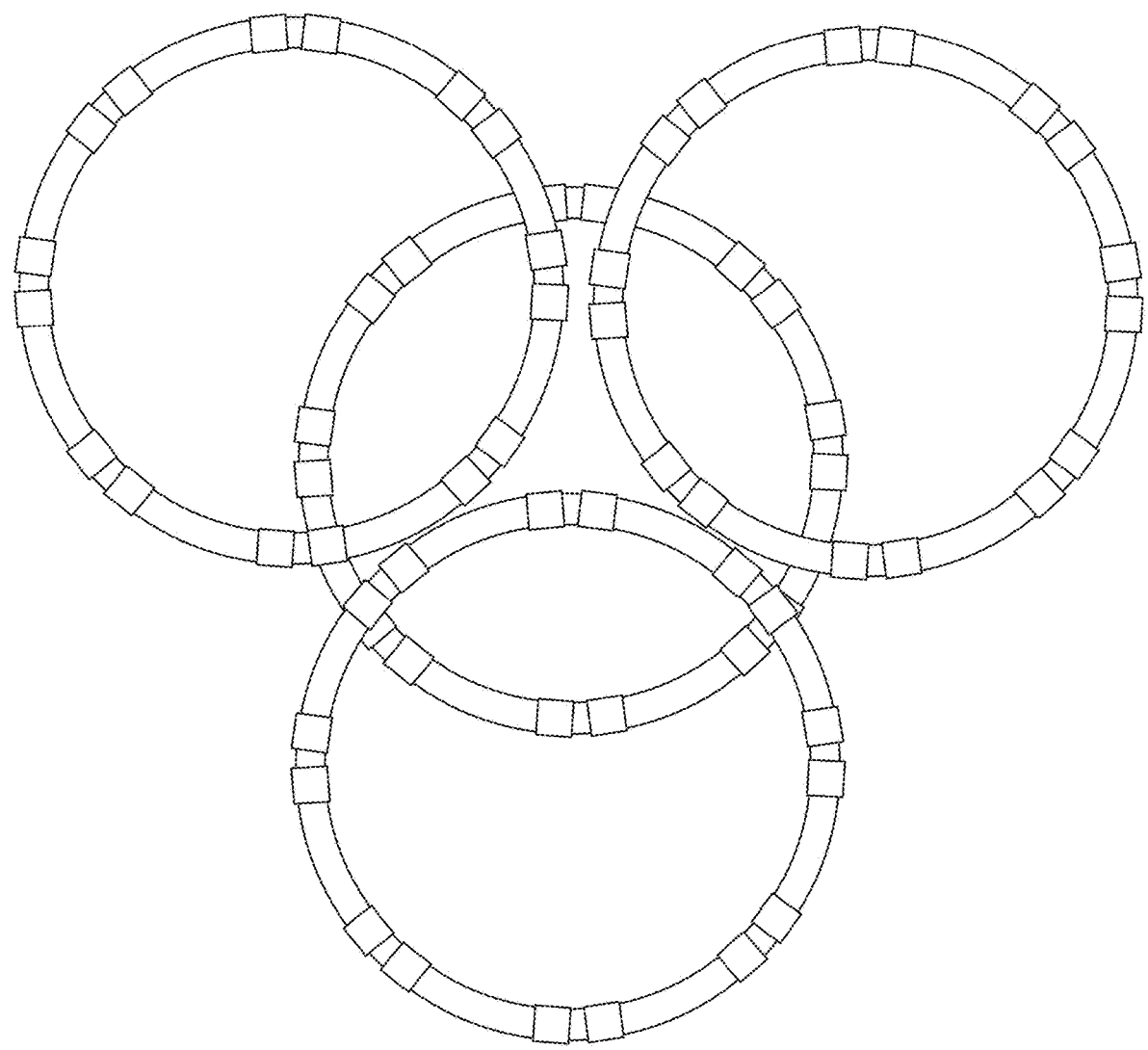
FIG. 26 illustrates an exemplary embodiment of a configuration of multiple adjacent and/or overlapping catheters.
Figure 27:
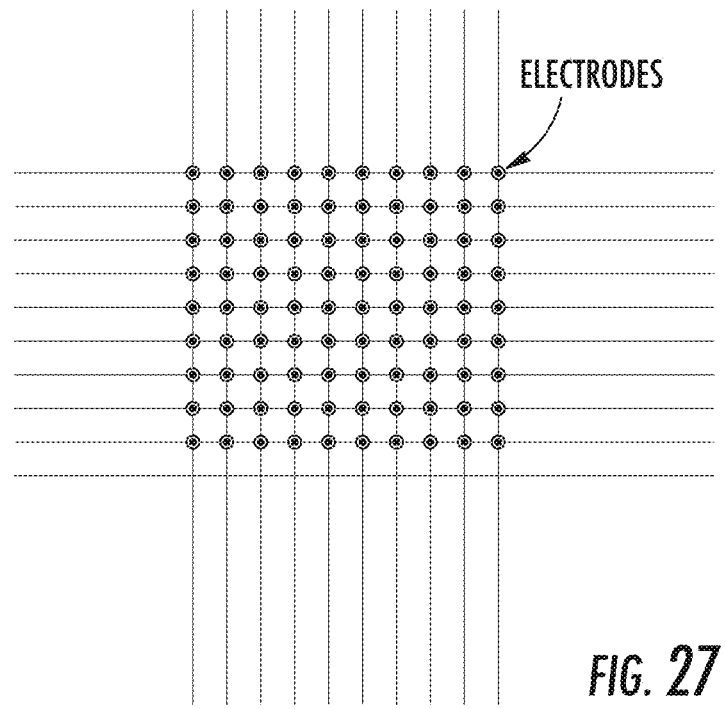
FIG. 27 illustrates an exemplary embodiment of an array of electrodes providing adjacent and/or overlapping perimeters.
Figure 28:
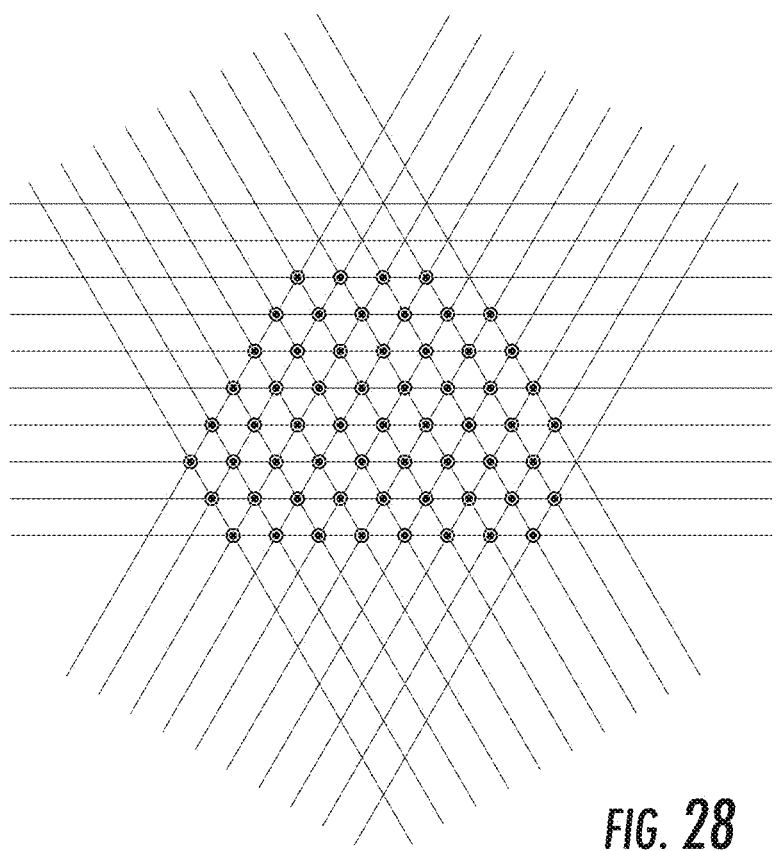
FIG. 28 illustrates another exemplary embodiment of an alternate geometric array of electrodes providing adjacent and/or overlapping perimeters.
Figure 29:
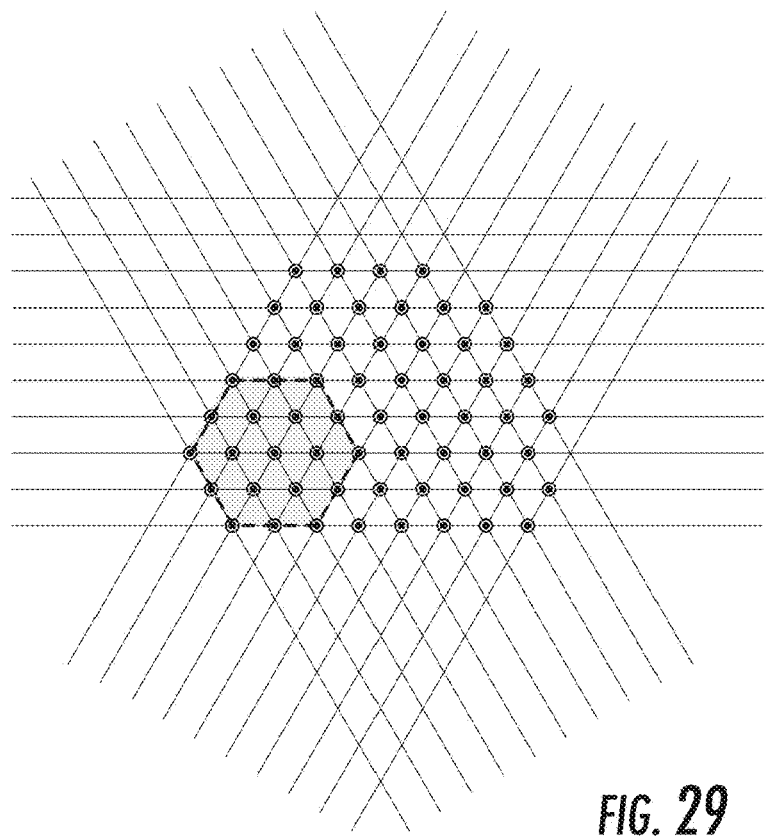
FIG. 29 is another illustration of the exemplary embodiment of an alternate geometric array of electrodes of present FIG. 28 providing adjacent and/or overlapping perimeters, and having an exemplary designated perimeter achieved with a selected grouping of electrodes.
Figure 30:
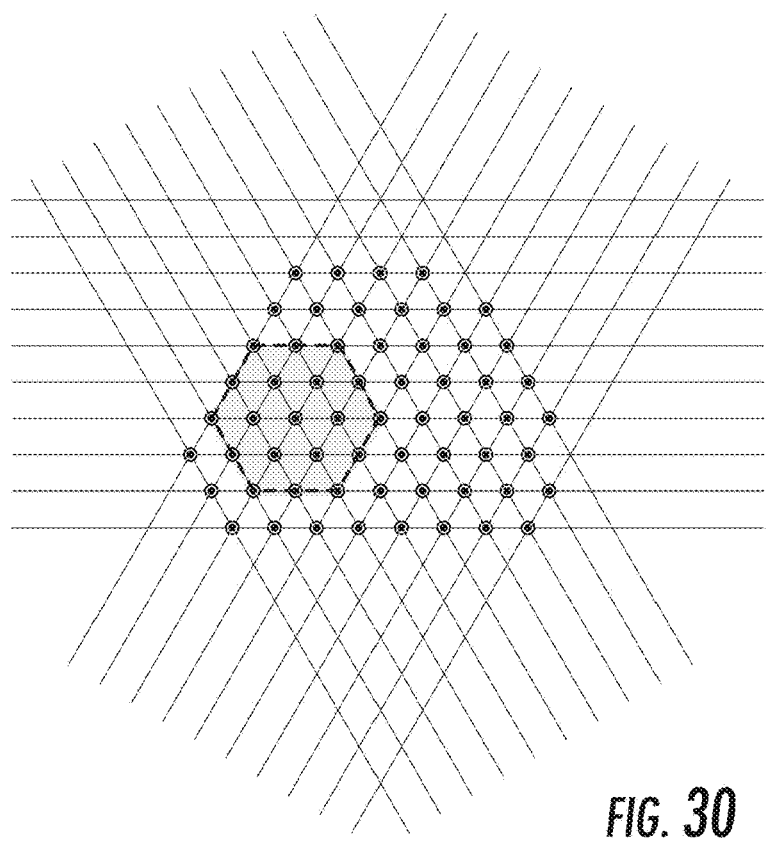
FIG. 30 is another illustration of the exemplary embodiment of an alternate geometric array of electrodes of present FIG. 28 providing adjacent and/or overlapping perimeters, and having another exemplary designated perimeter achieved with another selected grouping of electrodes.
Figure 31:
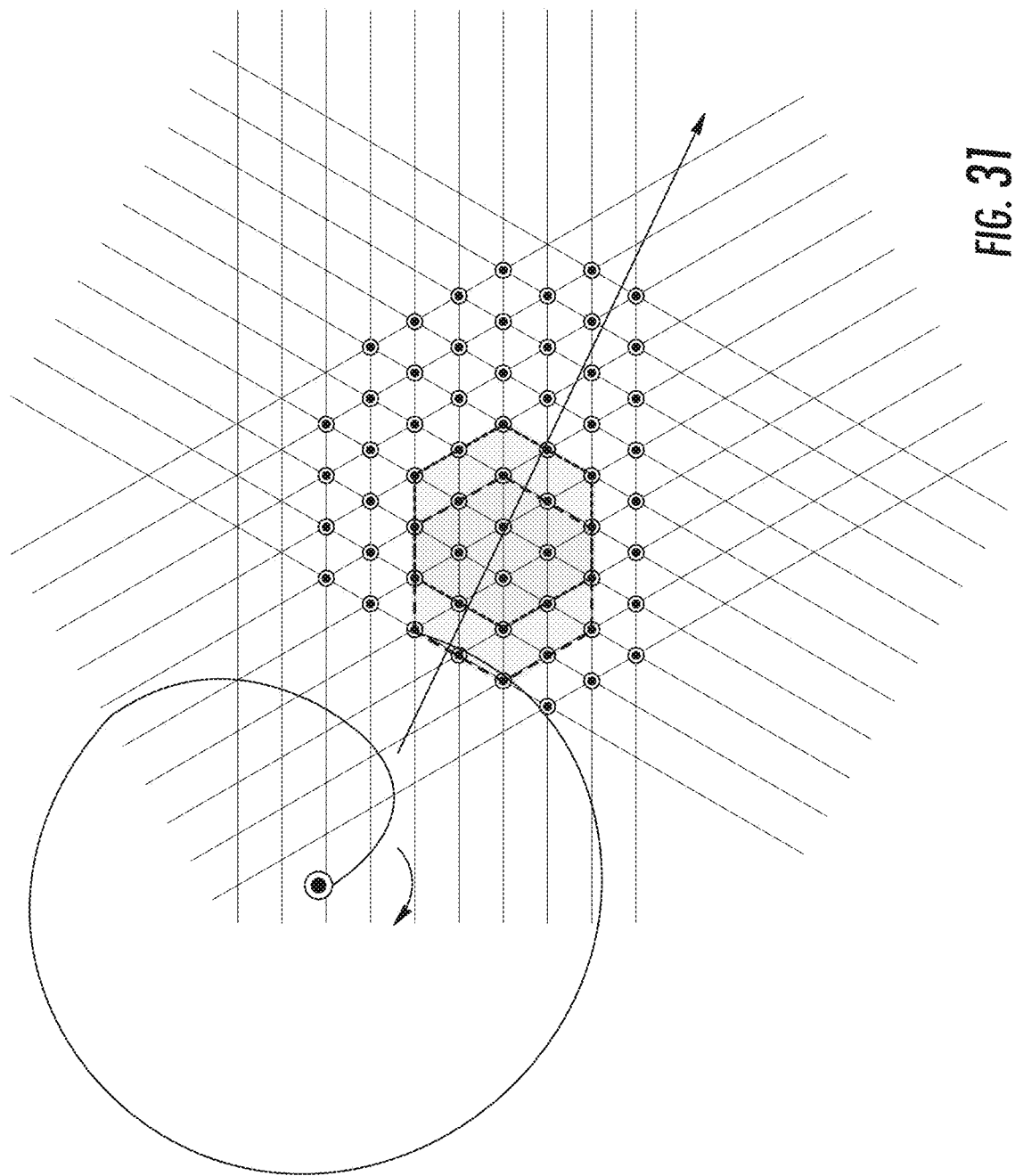
FIG. 31 is another illustration of the exemplary embodiment of an alternate geometric array of electrodes of present FIG. 28 providing adjacent and/or overlapping perimeters, and showing results of simultaneous recordings of a rotor precession past overlapping perimeters resulting from respective selected groupings of electrodes, and illustrating first and second of such perimeters and the direction of the rotor precession.
Figure 32:
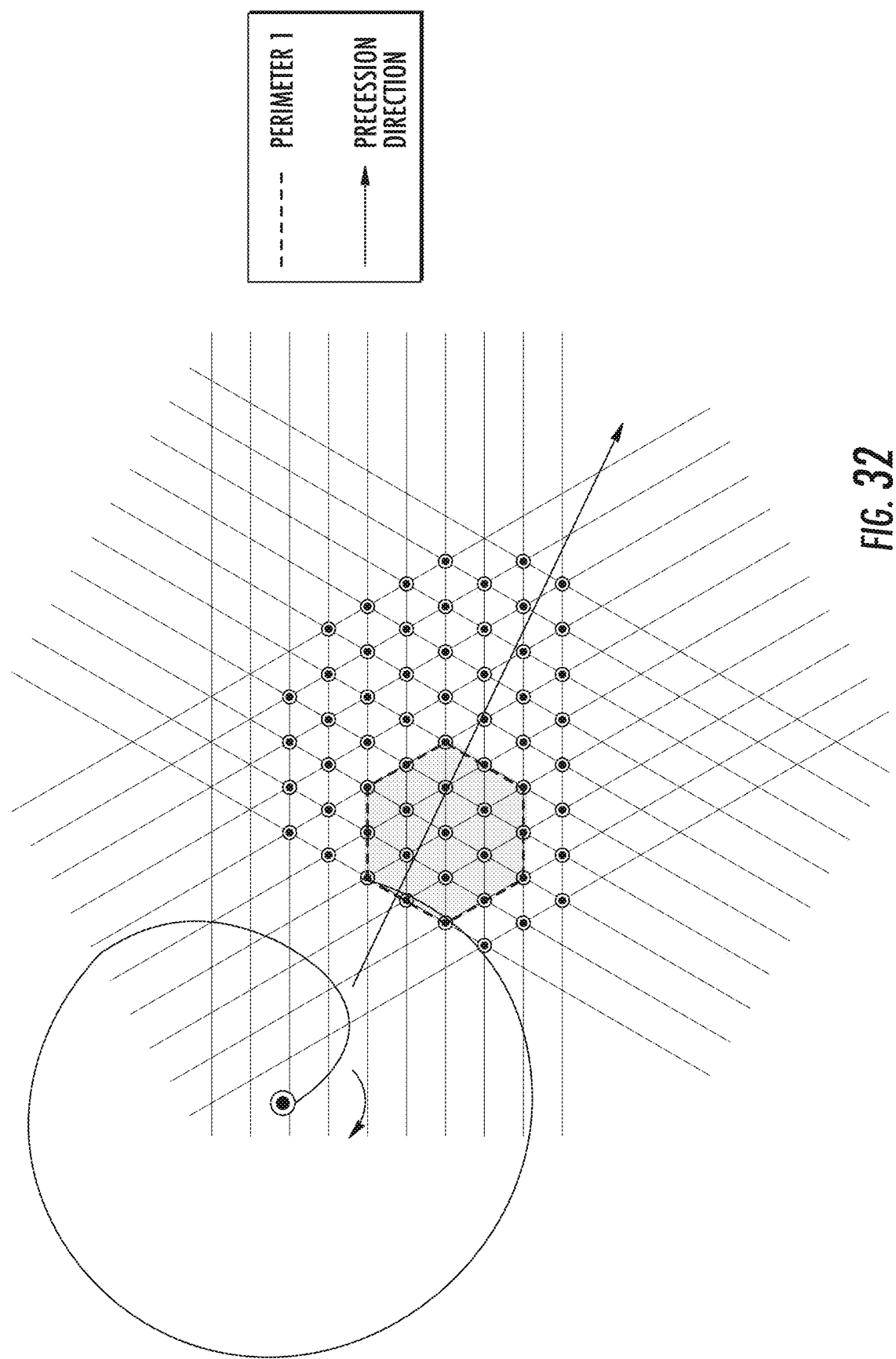
FIG. 32 is another illustration of the exemplary embodiment of an alternate perimeters, and showing results of the recording of a rotor precession outside of a perimeter resulting from a selected grouping of electrodes, and illustrating such perimeter and the direction of the rotor precession, based on all narrow pairs at such perimeter showing peripheral waves and with all cross perimeter electrode pairs showing peripheral waves.
Figure 35:
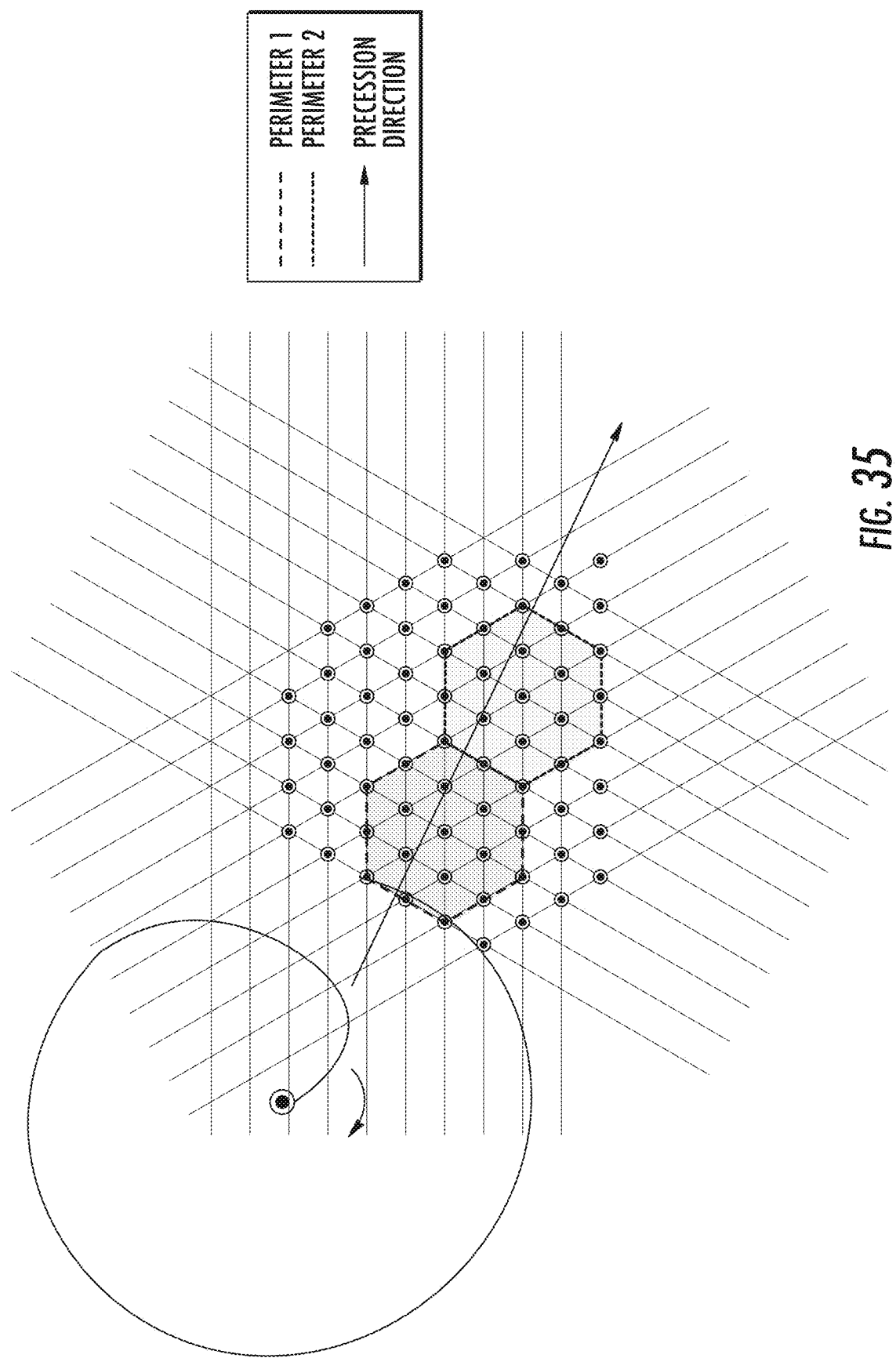
FIG. 35 is another illustration of the exemplary embodiment of an alternate geometric array of electrodes of present FIG. 28 providing adjacent and/or overlapping perimeters, and showing results of the recording of a rotor precession past adjacent perimeters resulting from respective selected groupings of electrodes, and illustrating first and second such perimeters and the direction of the rotor precession.
Figure 36:
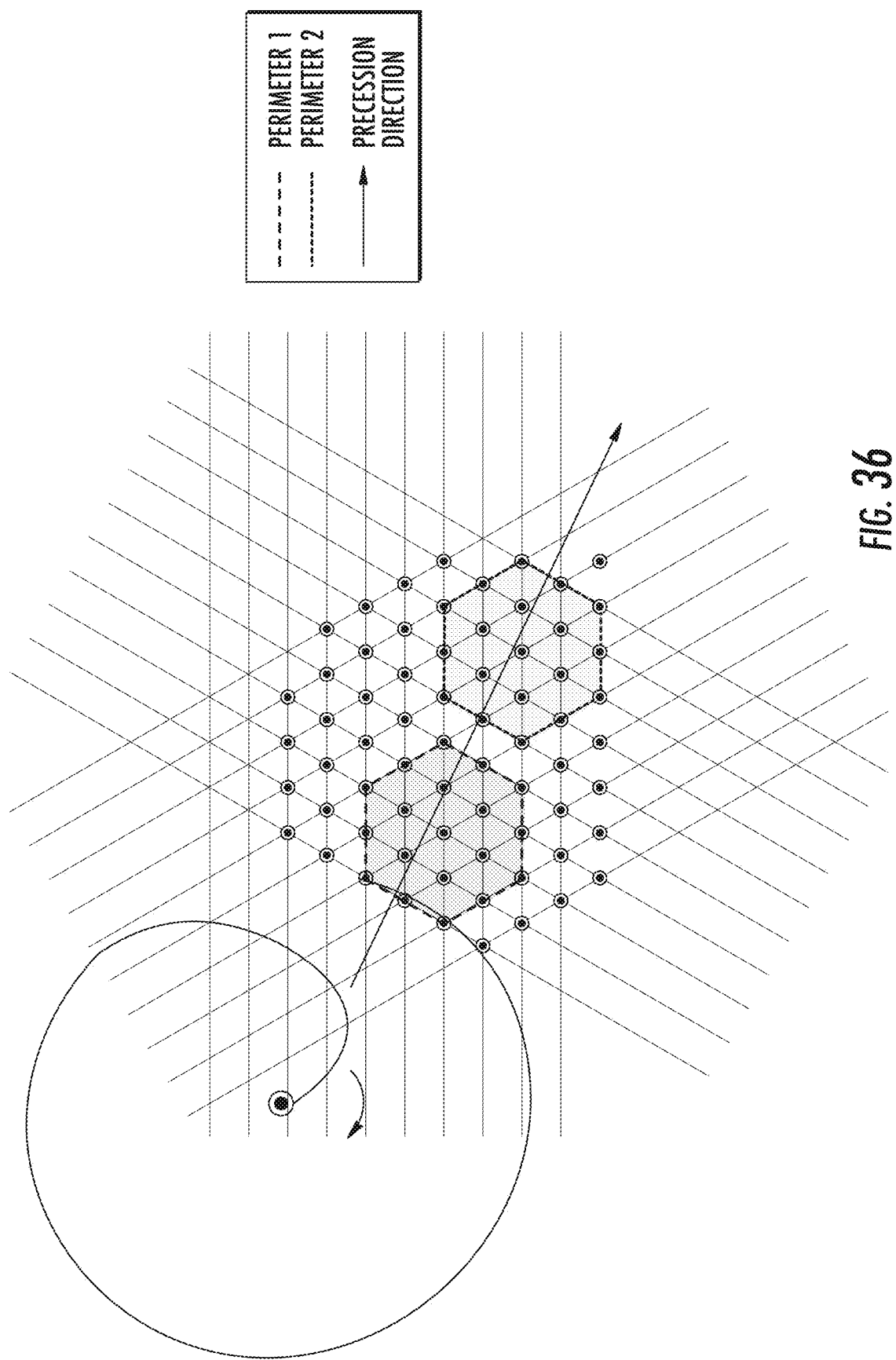
FIG. 36 is another illustration of the exemplary embodiment of an alternate geometric array of electrodes of present FIG. 28 providing adjacent and/or overlapping perimeters, and showing results of the recording of a rotor precession past another set of adjacent perimeters resulting from respective selected groupings of electrodes, and illustrating first and second such perimeters and the direction of the rotor precession.
Figure 37:
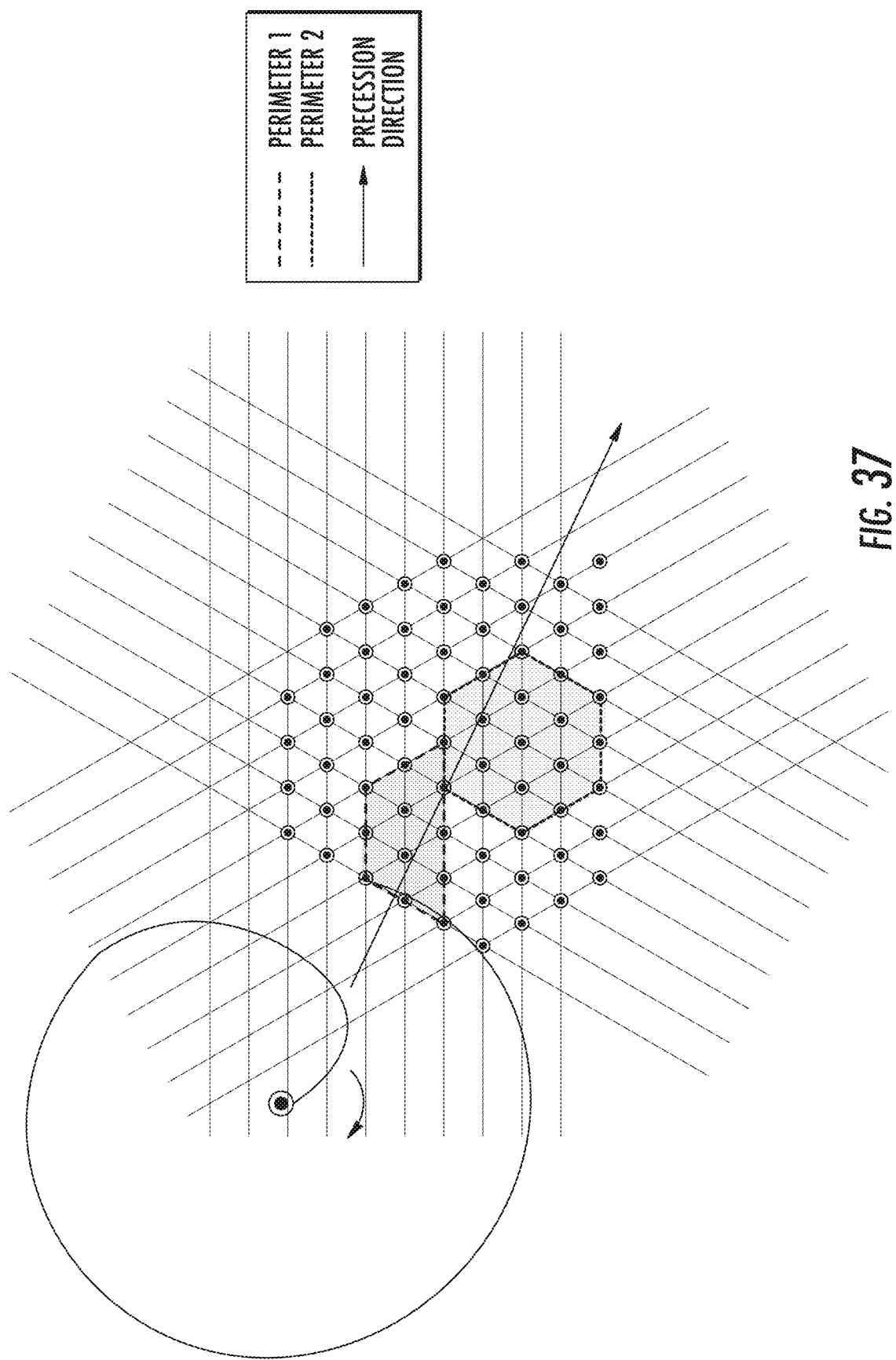
FIG. 37 is another illustration of the exemplary embodiment of an alternate geometric array of electrodes of present FIG. 28 providing adjacent and/or overlapping perimeters, and showing results of the recording of a rotor precession past adjacent perimeters resulting from respective selected groupings of electrodes having perimeters with different respective shapes, and illustrating first and second such perimeters and the direction of the rotor precession.
Figure 38:
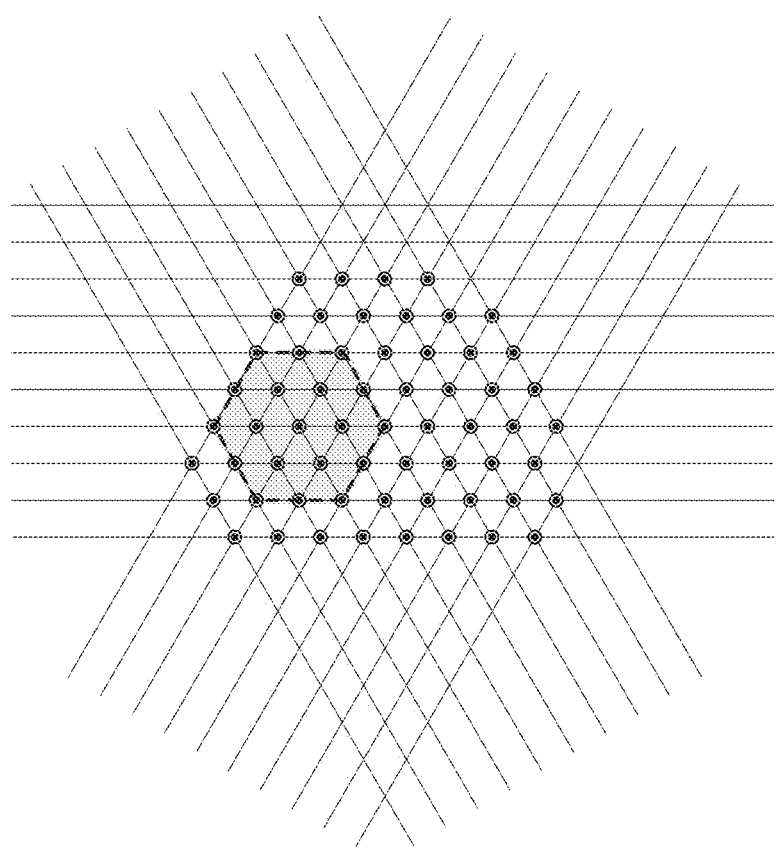
FIG. 38 is another illustration of the exemplary embodiment of an alternate geometric array of electrodes of present FIG. 28 providing adjacent and/or overlapping perimeters, and having another exemplary designated perimeter achieved with another selected grouping of electrodes.
Figure 39:
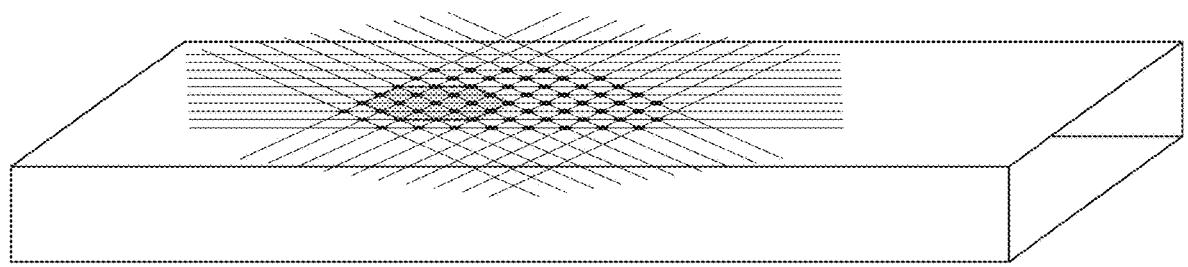
FIG. 39 is a three-dimensional representation of the array of electrodes and exemplary established perimeter per a selected grouping of electrodes as represented in present FIG. 38.
Figure 40:
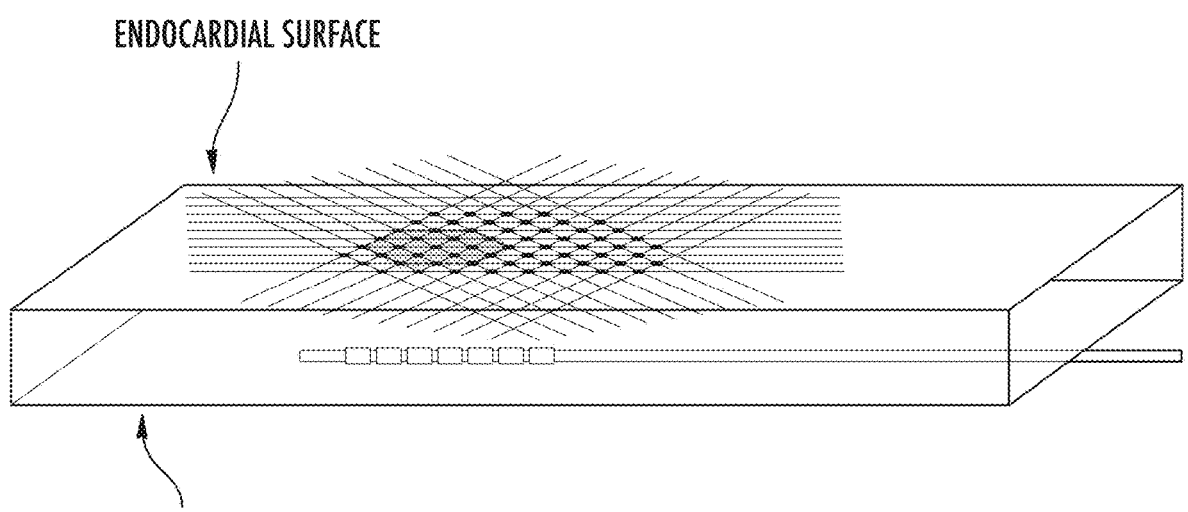
FIG. 40 is a three-dimensional representation of an array of electrodes similarly positioned as that in present FIG. 39, situated relative to a representative respective endocardial surface and respective epicardial surface associated with a patient.
Figure 41:
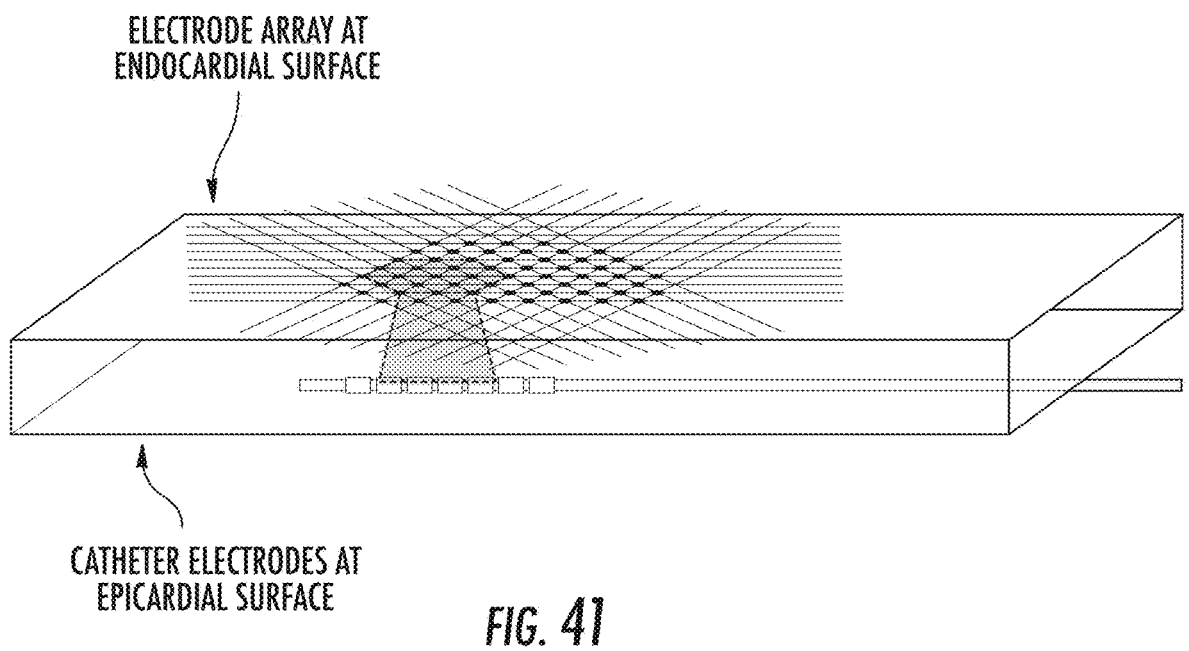
FIG. 41 is a three-dimensional representation of an array of electrodes similar to that as in present FIG. 40 and situated for creating perimeters at different planes through cardiac tissue of a patient, with a representative electrode array at the endocardial surface and with catheter electrodes at the epicardial surface.

FIG. 19A and FIG. 19B schematically illustrate one mapping process for collecting data across a left atrium. FIG. 20 presents a flow chart of an algorithm approach to collect the data. By way of example, after obtaining merged 3-dimensional left atrial structure according to standard methodology, the catheter including bipolar electrode pairs can be utilized to map the atrium. In general, the catheter can be in communication with a processor and related devices that can include software as is known for processing the electrical signals and providing the information concerning the electrical mapping of the cardiac tissue as output. For instance, a processor in communication with the catheter, e.g., a GE CardioLab™ EP Recording Station, can be loaded with suitable recognition and vector analysis software and can receive and analyze the data from the catheter. The processor can also include standard output software as is generally known in the art to provide the resulting data in a preferred fashion, e.g., an electrocardiogram.

According to one mapping scheme, a catheter can be initially placed at Position 1 (FIG. 19B) within a heart chamber (e.g., the left atrium as illustrated) and electrical signals recorded and saved for a period of time, e.g., about 1 minute. If fibrillation only is identified, then the catheter can be moved to Position 2, and recording completed for another period of time. The catheter can be moved sequentially through the positions as indicated on FIG. 19A and FIG. 19B with the information gained at each site stored to form a map of the entire heart chamber. Alternatively, the mapping can be carried out until a trigger or driver is located, upon which the identified site can be ablated, either with or without further mapping of the chamber.

At any position, if a wave front is recorded that, by the signal, can be recognized as coming from an area outside of the perimeter defined by the electrodes, the earliest and largest amplitude impulses of the electrode pair recordings can provide information with regard to directional deflection of the catheter so as to move the catheter (or redefine the selected electrodes of a larger array) in the direction of incoming propagated waves and thus closer to the fibrillation trigger or driver site. The site can then be tagged as a peripheral site and the tag can include a label of the wave front direction.

According to one embodiment, following tagging of a peripheral site, the perimeter defined by the electrodes can be relocated, e.g., by no more than 1 full diameter of a circular pattern of the bipolar electrodes in the direction toward the source of the wave front and another period of recording can be obtained. The refinement can continue until a rotor core source is found, tagged and recorded for the desired period. Precess direction can be noted and recorded as well.

During a mapping process, an atypical reentrant circuit may be recorded. In this embodiment, the source of a wave front can be a complete discreet circle within the chamber. In this case, the catheter peripheral site tags can result in a circle of tag points. The circuit can be labeled as a circuit site and the next position can be examined.

Ectopic foci can also be identified by use of the disclosed catheters. For example, when refining the catheter position by moving into the direction of an incoming peripheral site wave front, an ectopic focus might be found. In this case, rather than an immediate change to alternating sloped double potentials as is the case for a rotor core identification as described above, a centrifugal activation can be seen in which each pole of all of the electrode pairs can present with similar sloping potentials. This site can also be recorded for a period of time, tagged as an ectopic site, and the next site can be examined. After all sites in the left atrium have been examined (e.g., all 12 sites in the illustrated example), atrial fibrillation ablation can be carried out.

As shown in FIG. 20, based upon the assessed catheter recording, one of four recording results can be expected (fibrillation, periphery site, rotor core, ectopic focus). Since rotors can precess during the period of recording, three different recording results may be obtained from a single site. First, and most commonly, it can be expected to find fibrillatory activity. This activity can be recognized by irregular timing of all impulses across most, if not all, electrode pairs. Second, the catheter can record in regions of the peripheral spiral wave. These areas can vary in diameter. In a peripheral site region, fairly regular timing and somewhat stable directional information can be immediately available from the processor. However, since rotors can precess, gradual shifts in cycle lengths and wave front directions can be expected and observed. More rarely, an actual rotor core can be recorded. Rotor core recordings by the disclosed mapping catheters can have an immediate recognizable pattern, including a sudden alternating sloped double potential in all electrode pairs and a doubling of cycle frequency. Using the wave front directional information at a periphery site can also allow the user to locate a perimeter defined by a plurality of bipolar electrodes over a rotor core. The rotor core site can then be tagged and the information saved; for instance, in a 3-dimensional map for further assessment.

While certain representative embodiments and details have been shown for the purpose of illustrating the presently disclosed subject matter, it will be apparent to those skilled in this art that various changes and modifications may be made therein without departing from the scope of the presently disclosed subject matter. These and other modifications and variations to the presently disclosed subject matter may be practiced by those of ordinary skill in the art, without departing from the spirit and scope of the presently disclosed subject matter, which is more particularly set forth in the appended claims. In addition, it should be understood the aspects of the various embodiments may be interchanged both in-whole or in part. Furthermore, those of ordinary skill in the art will appreciate that the foregoing description is by way of example only, and is not intended to limit the presently disclosed subject matter so further described in the appended claims.

What is claimed is:

1. A method for mapping cardiac tissue for a patient experiencing atrial fibrillation, comprising:
    placing a mapping catheter comprising an array of electrodes in contact with cardiac tissue, the array of electrodes comprising an electrode configuration of the mapping catheter forming a perimeter of said array of electrodes and wired to enable concurrent wide cross-perimeter electrode pairings configured for compass mapping recordings across non-adjacent electrodes on opposing sides of said array of electrodes, and wired for narrow-adjacent bipolar recordings from said array of electrodes and wired for unipolar recordings from said array of electrodes, wherein the array of electrodes includes a plurality of bipolar electrode pairs with said plurality of bipolar electrode pairs defining the perimeter, wherein the array of electrodes further includes at least one pair of electrodes exterior to the perimeter for narrow-adjacent bipolar recordings;
    simultaneously and continuously measuring electrical signals from said array of electrodes and concurrently generating and simultaneously recording respective compass map readings, narrow-adjacent bipolar readings, and unipolar readings therefrom in real time; and
    analyzing the concurrently generated and simultaneously recorded respective compass, bipolar, and unipolar electrical signal readings to identify localized waveforms therein to determine at least one characteristic of a wave front of depolarization passing through the cardiac tissue.

2. The method as in claim 1, wherein said at least one characteristic comprises at least one of:
    the presence, direction, or source of the wave front of depolarization passing through the cardiac tissue;
    general location, core size, core location, rotational speed, rotational direction, precess direction, or precess velocity of a rotor; and
    life-cycle characteristics of a rotor including spawning of vortex shedding, migration, anchoring, or final demise.

3. The method as in claim 1, wherein said mapping catheter perimeter comprises a shape which is at least one of circular, elliptical, ovoid, or polygonal, or a perimeter with no clearly defined shape.

4. The method as in claim 3, wherein:
    said mapping catheter comprises a perimeter defining an enclosed area having a circular perimeter;
    said mapping catheter perimeter enclosed area includes a center that is equidistant from opposing points on said perimeter.

5. The method as in claim 3, further including analyzing the simultaneously measured and simultaneously recorded electrical signal readings to identify precession of a rotational waveform in and out of said catheter perimeter to determine direction and location of said rotational waveform.

6. The method as in claim 3, further including placing a plurality of the mapping catheters each respectively forming a perimeter, and analyzing simultaneously measured and simultaneously recorded electrical signal readings therefrom to identify precession of a rotational waveform in and out of said catheter perimeters, to determine direction and location of said rotational waveform.

7. The method as in claim 3, further including placing said mapping catheter to cover a plurality of respective locations in contact with the cardiac tissue of the patient, and analyzing electrical signal readings simultaneously measured and simultaneously recorded therefrom to identify precession of a rotational waveform in and out of said catheter perimeter at said respective locations thereof, to determine direction and location of said rotational waveform.

8. The method as in claim 7, further including placing a plurality of said mapping catheters in at least two adjacent planes to identify three-dimensionally precession of a rotational waveform moving from one perimeter to an adjacent perimeter.

9. The method as in claim 3, further including identifying a location of a rotational waveform crossing said catheter perimeter by identifying electrodes of said array of electrodes experiencing electrical signals having a Doppler compression and expansion with a ½ cycle drop off.

10. The method as in claim 1, further including:
    determining catheter perimeter breaches of identified double potential (DP) waveforms to determine the location and path of a rotational mechanism of such waveform based on identifying the location of breach around the catheter perimeter;
    identifying Doppler compression and expansion of cycle lengths of identified double potential (DP) waveforms at adjacent electrodes of said array of electrodes.

11. The method as in claim 1, wherein:
said mapping catheter comprises a generally circular structure of electrodes;
said simultaneously measured electrical signals are analyzed to determine activation patterns from said array of electrodes;
said activation patterns are characterized as at least one of double potential (DP) waveforms, peripheral wave (PW) waveforms, distal peripheral wave (DSPW) waveforms, and fibrillatory conduction (Fib).

12. The method as in claim 11, further comprising least one of:
moving the array of electrodes to a one or more successive sites and analyzing electrical signal readings from each successive site to determine the presence, direction, or source of a wave front of depolarization passing through the cardiac tissue; and
placing a plurality of the mapping catheters each respectively forming a perimeter a respective plurality of sites and analyzing electrical signal readings from each catheter at each respective site to determine the presence, direction, or source of a wave front of depolarization passing through the cardiac tissue.

13. The method as in claim 12, including measuring and recording electrical signal readings from said array of electrodes for a period of at least about 0.5 seconds for each of said successive sites.

14. The method as in claim 12, wherein said analyzing of said electrical signals includes identifying the presence or direction of a rotor core within the cardiac tissue.

15. The method as in claim 1, further including:
using said analysis of simultaneously measured and simultaneously recorded electrical signal readings to identify wave fronts of depolarization passing through the cardiac tissue as targets for ablation therapy;
providing at least one ablation electrode; and
selectively operating said ablation electrode to treat said targets for ablation therapy.

16. The method as in claim 1, further including synchronizing an image of the patient's cardiac tissue to be mapped with the simultaneously recorded electrical signal readings.

* * * * *